United States Patent
Brant et al.

(10) Patent No.: US 7,456,021 B2
(45) Date of Patent: Nov. 25, 2008

(54) ANALYSIS METHOD

(75) Inventors: Patrick Brant, Seabrook, TX (US);
Burkhard Endeward, Frankfurt (DE);
Hans Thomann, Bedminster, NJ (US);
Yuan-Ju Chen, Houston, TX (US);
Terry John Burkhardt, Huntley, IL (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 996 days.

(21) Appl. No.: 10/758,900

(22) Filed: Jan. 16, 2004

(65) Prior Publication Data

US 2005/0158864 A1 Jul. 21, 2005

(51) Int. Cl.
*G01N 31/10* (2006.01)
(52) U.S. Cl. .......................... 436/37; 502/522
(58) Field of Classification Search ............... 436/37; 502/522
See application file for complete search history.

(56) References Cited

U.S. PATENT DOCUMENTS

| | | | | |
|---|---|---|---|---|
| 4,202,938 | A * | 5/1980 | Haeckel et al. | 435/10 |
| 4,808,561 | A | 2/1989 | Welborn, Jr. | 502/104 |
| 5,324,698 | A | 6/1994 | Ala-Huikku et al. | 502/126 |
| 5,496,960 | A | 3/1996 | Piers et al. | 556/8 |
| 5,643,847 | A | 7/1997 | Walzer, Jr. | 502/117 |
| 5,972,823 | A | 10/1999 | Walzer, Jr. | 502/152 |
| 6,262,202 | B1 | 7/2001 | Walzer, Jr. et al. | 526/133 |
| 6,265,505 | B1 | 7/2001 | McConville et al. | 526/161 |
| 6,329,313 | B1 | 12/2001 | Fritze et al. | 502/202 |
| 6,355,594 | B1 | 3/2002 | McDaniel et al. | 502/152 |
| 6,368,999 | B1 | 4/2002 | Speca | 502/402 |
| 6,388,017 | B1 | 5/2002 | McDaniel et al. | 525/240 |
| 6,395,666 | B1 | 5/2002 | McDaniel et al. | 502/87 |
| 6,403,732 | B2 | 6/2002 | Marks et al. | 526/134 |
| 6,426,313 | B2 | 7/2002 | Walzer, Jr. et al. | 502/103 |
| 6,441,901 | B2 * | 8/2002 | McFarland et al. | 506/12 |
| 6,525,988 | B2 | 2/2003 | Ryu et al. | 365/223 |
| 6,552,137 | B1 | 4/2003 | Kao et al. | 526/133 |
| 6,555,495 | B2 | 4/2003 | Peterson et al. | 502/104 |
| 6,738,529 | B1 * | 5/2004 | Crevier et al. | 382/282 |
| 2001/0031695 | A1 | 10/2001 | Loveday et al. | 502/117 |
| 2002/0082367 | A1 | 6/2002 | McConville et al. | 526/119 |
| 2003/0008980 | A1 | 1/2003 | Mawson et al. | 526/61 |

FOREIGN PATENT DOCUMENTS

| | | |
|---|---|---|
| WO | WO 00/13792 | 3/2000 |
| WO | WO 00/40623 | 7/2000 |
| WO | WO 01/41920 | 6/2001 |
| WO | WO 01/44308 | 6/2001 |
| WO | WO 01/44309 | 6/2001 |
| WO | WO 01/58587 | 8/2001 |
| WO | WO 02/16455 | 2/2002 |

OTHER PUBLICATIONS

Diehl, S. C. et al., "*Polystyrene-supported 2-arylindenyl zirconocene catalysts for propylene polymerization*", Israel Journal of Chemistry, vol. 42, pp. 393-401 (2002).
Raimondi, M. E. et al., "*A Spectroscopic Study of Group IV Transition Metal Incorporated Direct Templated Mesoporous Catalysts Part 1: A Comparison between Materials Synthesized Using Hydrophobic and Hydrophilic Ti Precursors*", J. Phys. Chem. B, vol. 104, pp. 7102-7109 (2000).
Stork, M. et al., "*Combinatorial testing of supported catalysts for the heterogeneous polymerization of olefins*", Angewandte Chemie, International Edition, 39 (23), pp. 4367-4369 (2000).
Coevoet et al., "U.V./Visible Spectroscopic Study of the rac-Et(Ind)2ZrCl2/MAO Olefin Polymerization Catalytic System, 1 Investigation in Toluene" Macromol. Chem. Phys. vol. 199, pp. 1451-1457 (1998).
Coevoet et al., "U.V./Visible Spectroscopic Study of the rac-Et(Ind)2ZrCl2/MAO Olefin Polymerization Catalytic System, 2a Investigation in CH2CL2", Macromol. Chem. Phys. vol. 199, pp. 1459-1464 (1998).
Pedeutour et al., "Activation of iPr(CpFluo)ZrCl2 by Methylaluminoxane, 4a UV/visible Spectroscopic Study in Hydrocarbon and Chlorinated Media", Macromol. Chem. Phys. vol. 200, pp. 1215-1221 (1999).
U. Wieser and H.-H. Brintzinger, "UV-VIS Studies on the Activation of Zirconocene-Based Olefin-Polymerization Catalysts", in Organometallica Catalysts and Olefin Polymerization.
Landis et al., "Catalytic Propene Polymerization: Determination of Propagation, Termination, and Epimerization Kinetics by Direct NMR Observation of the (EBI)Zr(MeB($C_6F_5$)$_3$)propenyl Catalyst Species," Journal of the American Chemical Society, Vol. 125, pp. 9894-9895, 2003.
Blom et al., "UV/VIS Studies on the Activation of Zirconocene-Based Olefin-Polymerization Catalysts," Organometallic Catalysts & Olefin Polymerization-Catalysts for a New Millennium, pp. 3-13, 2001.

* cited by examiner

*Primary Examiner*—Jill Warden
*Assistant Examiner*—Natalia Levkovich

(57) ABSTRACT

Disclosed herein is a method for determining the presence of an activated catalyst site in a catalyst system comprising a catalyst precursor and an activator, wherein the catalyst system is capable of providing a luminescence, the method comprising: performing a time resolved luminescence analysis on a reference analyte comprising the catalyst precursor that is not in combination with the activator, and performing a time resolved luminescence analysis on a sample analyte comprising the catalyst precursor in combination with the activator, determining a reference emission energy and a reference lifetime each associated with a maximum emission intensity in the reference output values; determining a sample emission energy and a sample lifetime each associated with a maximum emission intensity in the sample output values; and comparing the values to determine if the sample comprises an activated catalyst site. Use of the above method in relation to an activation index is also disclosed.

12 Claims, 8 Drawing Sheets

(I)/MAO (1:200, 1mM) in Cyclohexane

(I) *in Cyclohexane at 80K*

(I)/FAB Ratio 1:1 in Cyclohexane at 80K

*FAB in Cyclohexane at 80K*

(I) /DMAHD4 (1:1.1,5mM) in Cyclohexane

(I)/MAO (1:100, 5mM) in Toluene

(I)/MAO (1:200, 5mM) in Toluene

# ANALYSIS METHOD

CROSS REFERENCE TO RELATED APPLICATIONS

This invention is related to concurrently filed U.S. Ser. No. 10/758,726, filed Jan. 16, 2004, which is incorporated by reference herein.

FIELD OF THE INVENTION

The present invention relates to a method utilizing time resolved luminescence to determine if a catalyst precursor in combination with an activator becomes activated. Also disclosed is an apparatus for making the determinations.

BACKGROUND

Polymerization catalysts offer opportunities for providing new processes and products to the markets. In particular, olefin polymerization catalyst systems are of great interest in making new products available.

One method of evaluating polymerization catalysts is to collect polymerization data in a laboratory and/or pilot plant setting using the polymerization catalyst under polymerization conditions in actual reactors. Polymerization activity measurements and analysis of polymers produced may then be used to determine catalyst activation, activity profile, and the like. Information obtained from actual polymerization may also be used to guide development of new catalysts and/or to guide in the scale up of catalysts systems in manufacturing processes.

Spectroscopic methods of analysis may also provide information about catalysts, for example: elemental analysis and imaging methods such as secondary ion mass spectroscopy (SIMS) and X-ray phosphorescence (XPS) may be used to determine various spatial distributions within a catalyst system, including metal loading on a catalyst support.

Ultraviolet/Visible absorption spectra (UV/Vis) is reported as being useful in determining the activation of a homogeneous catalysts system. It has been reported that the activation process can be followed by changes in the absorption bands in the UV/Vis spectra. (see for example D. Coevoet, H. Cramail, and A. Deffieux, Macromol. Chem. Phys. 199, 1451-1457, 1998; J. N. Pedeutour, D. Coevoet, H. Cramail, and A. Deffieux, Macromol. Chem. Phys. 1215-1221, 1999; A. Deffieux, Macromol. Chem. Phys. 199, 1459-1464, 1998;

It has been reported that MAO activation of zirconocene proceeds in more than one step, and that distinct absorption bands may be observed for each chemical species using UV/Vis (see for example U. Wieser and H.-H. Brintzinger, "UV-VIS Studies on the Activation of Zirconocene-Based Olefin-Polymerization Catalysts", in Organometallic Catalysts and Olefin Polymerization. Catalysts for a New Millenium R. Blum, A. Follestad, E. Rytter, M. Tilset, and M. Ystenes, eds. Springer, 2001.)

It has also been reported that $^1H$ and $^{13}C$ NMR can be used to probe the chemistry of activation for homogeneous catalysts. These reports are directed to studies used in a research mode to infer the structure of the activated metallocene and to investigate the kinetics of the activation. See for example, Landis et al., JA036393u.

However, such analysis does not provide detailed information of the chemical state of the catalyst, in particular the activation of the catalyst for metallocene containing catalyst systems. Nor do the methods provide information as to activation of supported catalyst systems. Accordingly, the need remains for a method of determining the chemical state of the catalyst, and in particular the activation of supported metallocene catalyst systems. Furthermore, the need exists for a method to determine the activation of a catalyst system, which can be practiced in either the manufacture of catalysts or for quality control in on-going commercial polymerization activities including manufacturing of various polymers.

SUMMARY OF THE INVENTION

Disclosed herein is a method for determining the presence of an activated catalyst site in a catalyst system comprising a catalyst precursor and an activator, wherein the catalyst system is capable of providing a luminescence, the method comprising:

a) performing a time resolved luminescence analysis on a reference analyte comprising the catalyst precursor that is not in combination with the activator, to produce a plurality of reference output values, each being associated with a time resolved emission intensity at an emission energy;

b) performing a time resolved luminescence analysis on a sample analyte comprising the catalyst precursor in combination with the activator, to produce a plurality of sample output values, each being associated with a time resolved emission intensity at an emission energy;

c) determining a reference emission energy and a reference lifetime each associated with a maximum emission intensity in the reference output values;

d) determining a sample emission energy and a sample lifetime each associated with a maximum emission intensity in the sample output values;

e) subtracting the sample emission energy from the reference emission energy to produce an energy difference value;

f) subtracting the sample lifetime from the reference lifetime to produce a lifetime difference value;

g) determining if the energy difference value, the lifetime difference value, or both, are an essentially non-zero value to determine if the sample comprises an activated catalyst site.

Also disclosed is a method for determining the presence of an activated catalyst site in a catalyst system comprising a catalyst precursor and an activator, wherein the catalyst system is capable of providing a luminescence, the method comprising:

a) performing a time resolved luminescence analysis on a reference analyte comprising the catalyst precursor that is not in combination with the activator, to produce a plurality of reference output values, each being associated with a time resolved emission intensity at an emission energy;

b) performing a time resolved luminescence analysis on a sample analyte comprising the catalyst precursor in combination with the activator, to produce a plurality of sample output values, each being associated with a time resolved emission intensity at an emission energy;

c) determining a reference emission energy and a corresponding reference lifetime associated with a maximum emission intensity in the reference output values;

d) determining a sample emission energy and a corresponding sample lifetime associated with a maximum emission intensity in the sample output values;

e) determining the activation index $\Omega$ for the sample emission energy and the corresponding sample lifetime, wherein the activation index is determined according to the equation:

$$\Omega = \left( \frac{\log(T_{max}^{unactivated}) - \log(T_{max}^{activated})}{\log(T_{max}^{unactivated})} \right)^2 + \left( \frac{E_{max}^{unactivated} - E_{max}^{activated}}{E_{max}^{unactivated}} \right)^2$$

wherein $T_{max}^{unactivated}$ represents the reference lifetime;

$T_{max}^{activated}$ represents the sample lifetime;

$E_{max}^{unactivated}$ represents the reference emission energy;

$E_{max}^{activated}$ represents the sample emission energy; and f) determining if the activation index for the sample energy and the corresponding sample lifetime is an essentially non-zero value to determine if the sample comprises an activated catalyst site.

DETAILED DESCRIPTION

Figure 1:
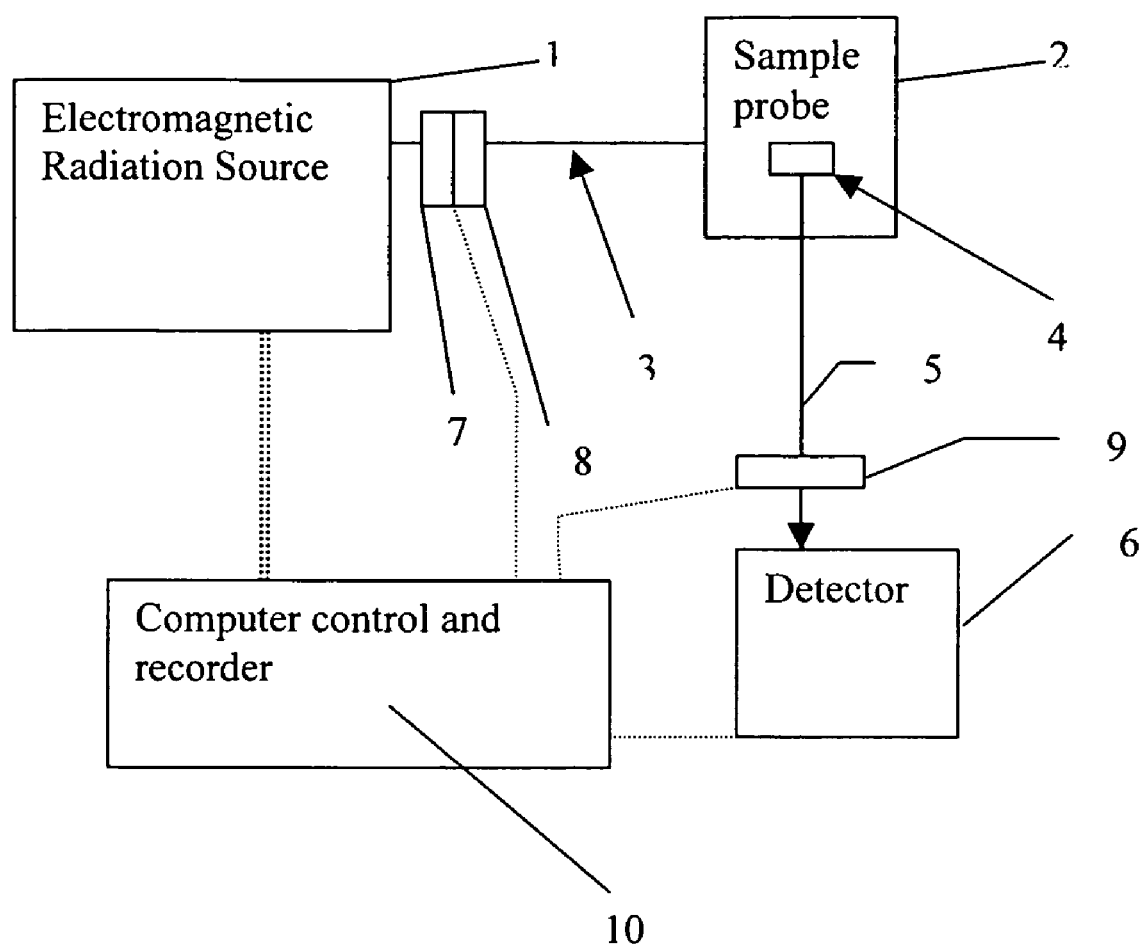
FIG. 1 depicts a spectrophotometer suitable for use herein.

Disclosed herein is a relatively quick and inexpensive method for determining the chemical environment of a catalyst and/or a catalyst system, preferably, an optical luminescence method of determining the activation of an olefin polymerization catalyst. A catalyst may be considered activated when an active catalyst site is present in the catalyst system. An activated catalyst site may be the combination of a catalyst precursor with an activator. The method comprises measuring a luminescence emission of electromagnetic radiation, preferably in the UV-Visible region of the electromagnetic spectrum, of both a reference material and a sample material, and then comparing the results. In a preferred method, a time-resolved luminescence spectrum of both a reference material and a sample material is measured, and the luminescence emission and the lifetime of the sample and the reference are compared to determine the chemical environment of the catalyst system under consideration.

For the purposes of this invention and the claims thereto, when a polymer is referred to as comprising an olefin, the olefin present in the polymer is the polymerized form of the olefin. The new numbering scheme for the Periodic Table Groups are used as described in CHEMICAL AND ENGINEERING NEWS, 63(5), 27 (1985).

A catalyst system, as used herein, refers to a combination of a catalyst and/or a catalyst precursor, an activator, and optionally a support. A catalyst precursor, also referred to herein as a pre-catalyst, refers to material that becomes catalytically active (forms an active catalyst site) when put in combination with an activator.

An activator is defined for use herein as any combination of reagents, process, conditions, or the like, which transforms a catalyst precursor into an active form capable of catalytic activity, and/or which increases the rate at which a catalyst functions, for example, oligomerizes an/or polymerizes an unsaturated monomer. An activator may also affect various properties of the reaction products produced by the catalyst, for example the molecular weight, degree of branching, comonomer content or other properties of an oligomer or polymer produced. As referred to herein, an activator may interchangeably be referred to a cocatalyst.

A support composition may include one or more base materials capable of providing physical support to another material. A support composition may also include various other materials in combination with the base material that provide various physical and chemical properties to the base material. Accordingly, a support composition may be interchangeably referred to herein as a support material or simply as a support. The combination of a support and an activator may be described as a catalyst support.

For purposes of this invention, Me is methyl, Ph is phenyl, Et is ethyl, Pr is propyl, iPr is isopropyl, n-Pr is normal propyl, Bu is butyl, iBu is isobutyl, tBu is tertiary butyl, p-tBu is para-tertiary butyl, TMS is trimethylsilyl, and a perfluoro radical is an organic radical having one or more available hydrogen atoms substituted with fluorine atoms.

The term luminescence, as used herein, includes the emission of electromagnetic radiation that does not derive energy from the temperature of the emitting body. Examples of luminescence include photoluminescence, phosphorescence, fluorescence, bioluminescence, Raman, and the like. Luminescence may result from chemical, biochemical, or crystallographic changes, the motions of subatomic particles, and/or preferably by radiation-induced excitation of an atomic system. Luminescence may also refer to the energy so emitted.

In a preferred embodiment, luminescence is derived from radiation-induced excitation of a catalyst system's atomic system. In a preferred embodiment, the method includes irradiating the analyte with one or more wavelengths of electromagnetic energy; and then measuring the time dependence and intensity of an emitted radiation at one or more emission energies.

Preferred wavelengths of both the electromagnetic radiation used to induce luminescence, and the emitted energy therefrom, have wavelengths ranging from the so-called Radio region i.e., wavelengths greater than or equal to about $10^9$ Angstroms (Å), to electromagnetic radiation having wavelengths in the Gamma Ray region, i.e., wavelengths less than or equal to about 0.1 Å. Most preferred luminescence wavelengths include those in the so-called Ultra Violet (UV) and Visible (Vis) regions, i.e., the UV-Vis region, having wavelengths of about 7000 Å to about 4000 Å for visible and about 4000 Å to about 10 Å for UV radiation such that the analyte is irradiated with electromagnetic energy having a wavelength of about 7000 Å to about 10 Å.

In one embodiment, the chemical environment (e.g., activity profile) of a catalyst system may be determined by comparing the wavelength of the maximum intensity of a spectrum of luminescence wavelengths of a catalyst system, to the wavelength of the maximum intensity of a spectrum of luminescence wavelengths of a reference. In this embodiment, a preferred reference includes, but is not limited to, the luminescence emission from a neutral or non-activated catalyst precursor, preferably a catalyst precursor in the absence of an activator, wherein the catalyst precursor is similar or identical to the activated catalyst system being analyzed.

In another embodiment, the chemical environment (e.g., activity profile) of a catalyst system may be determined by comparing the time resolved wavelength of the maximum intensity of a spectrum of luminescence wavelengths of a catalyst system, to the time resolved wavelength of the maximum intensity of a spectrum of luminescence wavelengths of a reference. In this embodiment, both the wavelength maxima, and the lifetime of the luminescence may be used in the determination. As before, a preferred reference includes, but is not limited to, the time resolved luminescence emission from a neutral or non-activated catalyst precursor, preferably a catalyst precursor in the absence of an activator, wherein the catalyst precursor is similar or identical to the activated catalyst system being analyzed.

In a preferred embodiment, the method comprises analysis utilizing time resolved luminescence (TRL), in which the time dependence of the amplitude of the luminescence, also referred to herein as intensity, is measured at one or more wavelengths. Utilizing TRL, the specific chemical state of the catalyst may be determined by comparing any shift in the luminescence emission wavelength (also referred to herein as the emission energy) between the standard and the reference, and/or by comparing any shift in the time dependence or lifetime of the luminescence emission observed for both the sample and the reference.

Accordingly, the method disclosed herein can be used to facilitate the discovery of new catalyst systems, the discovery of new catalysts, and optimization of activators and supports with catalyst systems. Examples include determination of activity wherein one or more essentially identical samples are prepared using different procedures. The method disclosed herein may be useful in determining effect(s) of support chemistry on catalyst, in determining interactions between catalyst sites in mixed catalyst systems, as a screening tool for quality control in on-going commercial polymerizations, and as a screening tool in high throughput experiments. The method disclosed herein may also be used in a manufacturing plant environment, for example to identify potential reactor operability problems such as poor activity or fouling. Accordingly, the method disclosed herein may save time and reduce costs in the development and scale up of a catalyst for commercial applications.

Spectrometer Useful in Analysis of Samples

In an embodiment, a spectrometer suitable for use herein is shown in block diagram in FIG. 1. Continuous wave (CW) luminescence spectra and/or time-resolved luminescence spectra may be recorded on a spectrometer comprising an electromagnetic radiation source (e.g., a light source) (1) for creating continuous wave illumination and/or pulses of light (e.g., using a continuous wave laser and/or a pulsed laser, respectively), a sample probe (2) for directing the incident light (3) to the sample (4) and directing the emitted luminescence response (5) to an optical detector (6), and an optical detector for detecting the luminescence signal, preferably in the presence of the much stronger fluorescence signal.

When luminescence in the UV-Visible range may be observed, the radiation source may include a variety of lasers, either continuous wave laser or a pulsed laser for optical excitation. When a continuous wave (CW) laser is used, the laser beam may be attenuated, preferably to approximately 1 milli Watt at the sample using, for example, a plurality of irises and/or a laser intensity stabilizer (such as LS-PRO CRI Laser Intensity Stabilizer available from Cambridge Research & Instrumentation, Inc. Woburn, Mass.) (7). In a preferred embodiment, pulses of light are created from the CW laser beam using an electro-optical "Q"-switch (8).

In this embodiment, the Q-switch (8) is preferably trigged on for a pulse length of about 1 to about 50 times the phosphorescence lifetime of the sample being analyzed. Switching times of about 0.5 to about 10 microseconds are preferred. It is also preferred that the light passing through the Q-switch (8) have an on-off intensity contrast of about 10 to about 40 compared to the on stage. In another embodiment, a pulsed laser may be used to induce the luminescence in the sample, as is well described in the art.

The sample probe is preferably dimensioned and arranged within the apparatus to accept a sample holder, for example a flame sealed 5-mm NMR tube, containing the sample of interest. Preferably, the sample tube is mounted and/or otherwise disposed within the instrument to allow for sample analysis at or below ambient temperature. For example, the sample may be disposed inside a liquid helium cryostat (e.g., Janis Model 7CNDT.) The cryostat allows the sample to be maintained below ambient temperature of about 25° C., which has been found to provide for an improved signal to noise ratio.

In some instances it may be desirable to record spectra at or above 298° K. In other instances, analysis may be obtained below ambient temperature of 25° C. while performing the time resolved luminescence analysis. A sample temperature of less than or equal to about 100° K is preferred, with a temperature of less than or equal to about 90° K more preferred. In one embodiment, analysis may be preferably conducted slightly above the boiling point of nitrogen, e.g., in a range of about 78° K to about 90° K, so as not to have interference from the boiling liquid. Within this temperature range, most analysis may be completed on the order of minutes.

A recording device, for example a digital oscilloscope, (e.g., Tektronix Model TDS724D) may be used for recording the time-resolved luminescence spectra. The wavelength dependent luminescence emission is preferably detected using a monochromators (9) (for example, PTI Model 101) at a wavelength resolution of about 0.5 to about 16 nanometers (nm). Also preferably included is a photomultiplier tube (PMT) detector (for example PTI Model 8 14, PMT Hamamatsu R928). In addition, one or more low pass optical filters may be used to filter out the excitation wavelength. In a fluorescence modality, the optical emission from the sample is preferably detected at 90 degrees away from the direction of the incident light beam to reduce the intensity of the incident light that reaches the detector.

Preferably, the excitation and recording of output values associated with a time resolved emission intensity at a particular emission energy of an analyte are computer controlled (10) with software designed for that purpose.

In a preferred embodiment, data algorithms may be utilized to associate various data output values with particular decay or lifetimes, wavelengths, and intensities. In so doing, data algorithms may be used in fitting a time dependent signal to a time dependant function useful to correlate time dependence, wavelength, and intensities. For example, in an embodiment, an inversion program useful in fitting a time dependant signal to a sum of exponentials by numerically solving the Fredholm integral equation:

$$f(x) = \int_a^b K(x, t)\phi(t)dt.$$

may be used to analyze time dependent luminescence.

Determination of Catalyst System Activity

A catalyst system may comprise a number of various components. Each in turn may affect the activity of the catalyst system, in both a positive and negative fashion. In addition, impurities, process concerns and the like may affect the activity of a catalysts system.

Activity of a catalyst system may be determined by actually producing an intended material, for example, in a reactor under controlled conditions. However, such testing is time and resource intensive, and fraught with a variety of other variables which may affect the overall outcome of the system, but which are essentially unrelated to a proposed end use of the particular catalyst system being evaluated. Such obstacles may impede discovery of new catalyst systems, may limit optimization of known catalyst systems, may pose quality control issues during production of catalyst systems, and may impede production of products with existing catalyst systems.

However, the method disclosed herein can be used to facilitate the discovery of new catalyst systems, the discovery of new catalysts, the optimization of known catalyst systems, provide quality assurance/quality control during production of catalyst systems, and provide for quality assurance/quality control functions during production of intended products.

In a preferred embodiment, the method disclosed herein may facilitate new discovery of new catalyst systems by providing a quick and inexpensive method of determining if a catalyst precursor becomes activated (i.e., the activation profile of a particular catalyst precursor) in combination with a particular activator under various conditions. Such methods are amenable to so-called high throughput screening techniques utilizing, for example, a plurality of catalyst precursors and/or a plurality of potential activators. In this case, reference materials may be the catalyst precursor or precursors, whose spectral response, time resolved spectral response, or both, may then be compared to that of the combination of the catalyst precursor(s) with one or more potential activators. Comparison of analysis results, as described in detail herein, which yields an essentially non-zero value, may indicate an activated catalyst system.

Optimization of known or unknown systems may also be provided for using the presently claimed invention. The character and/or intensity of a response of a sample analyzed as described herein, which can be correlated to a change in a particular parameter within the catalyst system, may prove beneficial in improving the activity or other parameters of a catalyst system. For example, comparison of analysis results, either positive or negative, with respect to the concentration of an activator within the catalyst system may provide an indication of the optimum level of activator under a particular set of conditions.

Optimization schemes useful with the method disclosed herein also extend to various parameters associated with a particular component of a catalyst system. For example, the comparison of analysis results obtained with respect to a particular conditioning temperature, pressure or the like (e.g., calcination temperature and conditions of a support), which can be correlated to an activity profile utilizing the method described herein, may provide an indication of an optimum value for a parameter under a particular set of conditions.

Various combinations of known and/or as of yet unknown materials in a particular system may also allow the method disclosed herein to be useful in a combination of new discovery, and optimization of a catalyst system. In this modality, the method disclosed herein may be useful in determining the effect of various impurities, cocatalysts, solvents, temperatures, and other components and conditions utilized with a particular catalyst system and/or systems. Accordingly, the activity of a plurality of catalyst systems, alone or in combination, may also be determined utilizing the method disclosed in the presently claimed invention herein.

The presently claimed invention may also be useful in a quality control function. For example, the method may be used for quality control during catalyst production, and/or quality control during production of an intended product. For example, as a catalyst system, or a component of a catalyst system is being produced, the method may be utilized to quickly and accurately determine if the analyte of interest demonstrates an acceptable level of performance in a given system, as opposed to conducting a polymerization using the material of interest. In an on-going commercial polymerization process, such as in a manufacturing plant environment, analysis of a catalyst system and/or on of the systems various components may be utilized to identify potential issues which may affect production such as reactor operability problems, poor activity, fouling, and the like. Accordingly, the method disclosed herein may be useful to save time and to reduce costs in the development, scale up, and production of a catalyst system for commercial applications, and/or in monitoring commercial or other catalytic processes, without having to resort to actually producing a product to gauge performance of a catalyst system.

Determination of Activity Profile of a Catalyst System

Preferably, an activated catalyst comprises an active catalyst site, which may be a pre-catalyst, also referred to herein as a catalyst precursor, in combination with an activator. Determination of activation of the pre-catalyst with the activator to produce an activated catalyst site within the catalyst system using luminescence and/or time resolved luminescence spectra requires determination of the correlation between a sample and a reference, preferably comparison between a time resolved luminescence emission energy of a sample, and a time resolved luminescence emission energy of a reference compound.

In one embodiment, and in no particular order, a time resolved luminescence spectrum of a catalyst precursor in the absence of an activator is obtained. This analysis may then be used as the reference against which the a time resolved luminescence spectrum of the catalyst precursor in combination with an activator is compared to. Preferably, these spectra are obtained in similar solvents, at similar temperatures, at similar concentrations, with similar impurities present, and under similar external conditions. More preferably, the spectra are obtained under essentially identical conditions, save the presence of an activator or activators.

Once the time resolved luminescence spectra are obtained, a reference luminescence emission intensity associated with a maximum reference output value in the reference spectrum is determined. This reference luminescence emission intensity is also referred to herein as a reference emission energy value. Also, a reference luminescence lifetime value associated with the reference emission energy value is preferably determined. This reference luminescence lifetime value is referred to herein as a reference lifetime.

Accordingly, a sample luminescence emission intensity associated with a maximum sample output value in the sample luminescence spectrum is determined. This sample luminescence emission intensity is also referred to herein as a sample emission energy value. A sample luminescence lifetime value associated with the sample emission energy value is also preferably determined. This sample luminescence lifetime value is referred to herein as a sample lifetime.

In one embodiment, activation of a catalyst with an activator in a sample is determined by subtracting the sample emission energy value from the reference emission energy value to produce an energy difference value. Likewise, the sample lifetime is subtracted from the reference lifetime to produce a lifetime difference value. A determination can then be made as to whether or not the energy difference value, the lifetime difference value, or both, are essentially non-zero numbers. Each of the values may independently be positive numbers or negative numbers, depending of the catalyst system and conditions, which are determined consistent with activation of the analyte.

Preferably, a catalyst may be considered activated when the lifetime difference value is a positive number (i.e., the lifetime value is less than the corresponding reference lifetime value), and/or the energy difference value is a positive number (i.e., the sample emission energy is less than the reference emission energy) and/or when the energy difference value is a negative number (i.e., the sample emission energy is greater than the reference emission energy).

As used herein, a lifetime value, an energy difference value, and/or the like is essentially non-zero when the value is greater than or less than zero by an amount exceeding the experimental and inherent errors associated with the analysis, which is readily determined by one of skill in the art. In a preferred embodiment, an essentially non-zero value is obtained when a lifetime value, an energy difference value, and/or the like, is greater then 1 times the signal to noise ratio of the measurement. Preferably, an essentially non-zero value is obtained when a lifetime value, an energy difference value, and/or the like, is greater then or equal to about 2.5 times the signal to noise ratio of the analysis, with greater than or equal to about 5 times the signal to noise value more preferred, and greater than or equal to about 10 times the signal to noise value especially preferred.

As used herein, signal refers to the portion of the measurement which results from the analyte of interest, and noise refers to the portion of the system originating from background, error, and/or anything else not related to the analyte of interest. Noise may be determined utilizing a mathematically fitted average and/or a weighted average, transform, or the like of a particular measurement utilizing one or more methods known to one of reasonable skill in the art. Preferably, the level of background noise for an analysis is determined in a portion of a measurement comprising essentially no signal from the analyte of interest.

In another embodiment, activation of the catalyst occurs when the energy difference value, the lifetime difference value, or both, exceed a predetermined emission energy difference value and/or a predetermined lifetime difference value, respectively. These predetermined reference values may be obtained from measurements made on similar systems under similar environments. Accordingly, these values may be determined using empirical methods. Such predetermined values may also be arrived at using theoretical calculations, depending on the type of luminescence, sample, reference, and measurement employed.

In a more preferred embodiment, a sample adjudged to exceed a predetermined emission energy difference value and a predetermined lifetime difference value (either positive or negative) is considered to comprise an activated catalyst (i.e., a catalyst precursor which has been activated by an activator to produce a catalytically activated site). In this preferred embodiment, a sample adjudged not to exceed a predetermined emission energy difference value and a predetermined lifetime difference value may not be considered to comprise a catalyst precursor activated by an activator.

The predetermined difference value may be determined relative to empirical measurements, preferably measurements confirmed using polymerization and/or other methods to confirm conditions under which a particular catalyst system is activated.

In one embodiment, the sample emission energy difference value is preferably greater than or equal to about 500 cm$^{-1}$, more preferably greater than or equal to about 1000 cm$^{-1}$, still more preferably greater than or equal to about 1500 cm$^{-1}$.

The sample lifetime difference value is preferably greater than or equal to about 0.05 milliseconds (msec.), more preferably greater than or equal to about 0.1 msec., still more preferably greater than or equal to about 0.15 msec.

Preferably, the sample emission energy difference value is preferably greater than or equal to about 500 cm$^{-1}$ and the sample lifetime difference value is preferably greater than or equal to about 0.05 msec., more preferably greater than or equal to about 1000 cm$^{-1}$, and 0.1 msec. respectively, with greater than or equal to about 1500 cm$^{-1}$, and 0.15 msec. being especially preferred.

Figure 2:
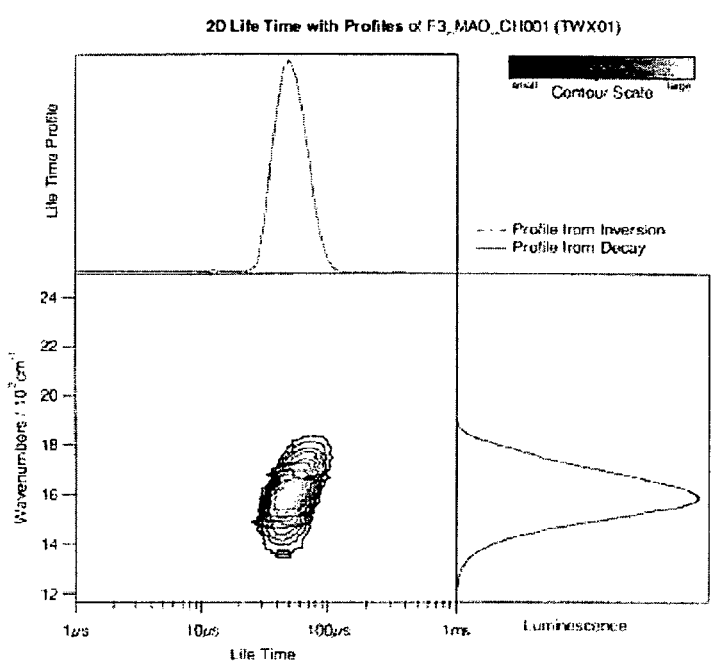
FIG. 2 depicts a time resolved luminescence spectrum of Metallocene (I) activated with MAO (1:200) in cyclohexane at 80° K.

In a preferred embodiment, determination of an analyte emission energy and the corresponding lifetime associated with a maximum output value in the spectrum of the analyte may be made using a combination of 2-D Luminescence spectra plotted in the various plots as shown in FIG. 2. Preferably, in the 2D-luminescence contour-plot (11), the bottom left horizontal direction is the luminescence lifetime axis (12), while the vertical direction is the luminescence emission energy axis (13) (in wavenumbers, $10^3$ cm$^{-1}$). In this format, the intensity of the luminescence emission energy is perpendicular to the page; the relation between luminescence emission energy and the intensity may be shown in a legend code of the plot (14) located at the top right of this preferred layout.

Preferably, these contour data are inversion data calculated from the experimental transient data according to the equation:

$$L(t) = \Sigma_i A_i \exp(-t/\tau_i),$$

wherein L(t) is the sum (area under the curve) of the intensity at time t for the time dependent luminescence signal measured at a particular emission energy;
$A_i$ the $i^{th}$ amplitude component for the decay lifetime $\tau_i$;
t is time; and
$\tau_i$ is the decay lifetime.

In FIG. 2, the top left portion, the Lifetime profile (15), as well as the bottom right portion the Luminescence profile

(16) show spectral profiles (also referred to herein as plots) of the 2D-Luminescence. The Lifetime profile (15) preferably represents integration along the wavenumbers (energy) with summation of intensities in the vertical direction of 2D-Luminescence data. In other words, the vertical is the integrated intensity, versus the luminescence emission lifetimes in the horizontal direction.

The Luminescence profile (16) shown in the bottom right graph of FIG. 2 preferably contains several profiles or spectra. These include the integration along the lifetimes of the 2D-Luminescence data with summation of intensities in the horizontal direction of the 2D-Luminescence data. Thus, the horizontal axis is the integrated intensity versus the wavenumbers (energies) on the vertical axis. The amplitude of the luminescence at the end of the excitation laser pulse taken directly from the experimental transient date may also be shown. These two profiles are identical when the inversion algorithm worked properly in that a deviation between the profiles would indicate that the transient data could not be simulated by the predefined range of lifetimes used in the inversion.

Possible reasons for inaccurate inversion include intense fluorescence at larger energy (wavenumbers) with shorter lifetimes than the switching time of the Q-switch (e.g., <1 microsecond); it may be necessary to cut the part out of the inversion, or the recorded time range of the transient are to short. In addition, the signal to noise ratio (S/N ratio) may be to low, resulting in a slight deviation observed in the plot.

The maxima in the data plots (17) are preferably the values of the intensity plots where the corresponding peaks are observed at a maximum above the signal to noise ratio, preferably the maxima is the base peak (representing 100% intensity) in the spectrum. In a preferred embodiment, the value of the base peak of the plot found at $x_o$ satisfies the extremum test, wherein the plot may be represented by a function $f(x)$ in one dimension. If $f(x)$ has a relative and/or global extremum at $x_0$, then either the first derivative of $f(x)$ is zero, represented herein as $f'(x_o)=0$, or f is not differentiable at $x_o$. Either the first or second derivative tests may also be used to locate relative extreme of the first kind. Accordingly, a necessary condition for $f(x)$ to have a maximum at $x_o$ is $f'(x_o)=0$, and the second derivative of $f(x_o)$ is less than or equal to 0, represented herein as $f''(x_o) \leqq 0$. More than one maximum may be present in the data plots, which may indicate a plurality of species and/or partial activation of a catalyst precursor.

The method disclosed herein may also be used to determine the number of active sites for a catalyst system comprising a plurality of activated sites. In this modality, the method comprises performing a time resolved luminescence analysis on a reference analyte comprising the catalyst precursor that is not in combination with the activator, to produce a plurality of reference output values, each being associated with a time resolved emission intensity at an emission energy; performing a time resolved luminescence analysis on a sample analyte comprising the catalyst precursor in combination with the activator, to produce a plurality of sample output values, each being associated with a time resolved emission intensity at an emission energy; determining a reference emission energy and a reference lifetime associated with a maximum reference output value in the time resolved luminescence analysis of the reference; determining a sample emission energy and a sample lifetime associated with a maximum sample output value in the time resolved luminescence analysis of the sample; subtracting the sample emission energy value from the reference emission energy value to produce an energy difference value; subtracting the sample lifetime from the reference lifetime to produce a lifetime difference value; and determining if an energy difference value, a lifetime difference value, or both, are essentially non-zero values to determine the activation state of the catalyst system.

However, when a plurality of sample emission energy maxima and a plurality of sample lifetimes each individually associated with a particular sample emission energy maxima are determined to exist in the time resolved luminescence analysis of the sample, and wherein a plurality of the energy difference values, a plurality of the lifetime difference values, or a plurality of both, each comprise an essentially non-zero value relative to a reference, then each essentially non-zero sample emission energy difference value, each sample lifetime difference value, and/or both may represent an active site in a catalyst system comprising one or more activated sites.

Accordingly, a method for determining the number of activated catalytic sites in a catalyst system comprises determining a plurality of sample emission energies and a plurality of sample lifetimes each individually associated with a particular maximum emission intensity in the sample output values as described above;

subtracting each sample emission energy from the reference emission energy to produce a plurality of energy difference values;

subtracting each sample lifetime from the reference lifetime to produce a plurality of lifetime difference values; and determining if one or more of the plurality of energy difference values, the plurality of lifetime difference values, or a plurality of both, comprise an essentially non-zero value, wherein each essentially non-zero energy difference value, each essentially non-zero sample lifetime difference values, or both represent an active catalyst site in the catalyst system, to determine the number of active catalyst sites in the catalyst system.

The method disclosed herein may also be used to determine weather or not a partially activated catalyst system is present in a sample. For example, when an essentially zero sample emission energy value, sample lifetime value, or both is determined, along with one or more essentially non-zero sample emission energy values, sample lifetime values, or both, then a partially activated catalyst system may be present in the sample.

Accordingly, a method for determining the presence of a partially activated catalyst site in a catalyst system comprises determining a plurality of sample emission energies and a plurality of sample lifetimes each individually associated with a particular maximum emission intensity in the sample output values;

subtracting each sample emission energy from the reference emission energy to produce a plurality of energy difference values;

subtracting each sample lifetime from the reference lifetime to produce a plurality of lifetime difference values; and determining if the plurality of energy difference values, the plurality of lifetime values, or both comprise an essentially zero value, determining if the plurality of energy difference values, the plurality of lifetime values, or both comprise an essentially non-zero value, to determine the presence of a partially activated catalyst site in the catalyst system.

In addition to the qualitative determination of the existence of an activated site either being present, partially present, or not present within a given catalyst system, the method disclosed herein may also be used to determine relative and/or absolute concentrations of the active catalyst species present in a particular sample. For example, in a situation where a maximum is determined to exist in the time resolved sample analysis, and wherein a sample lifetime corresponding to that maximum is determined to exist, and wherein the energy difference value, the lifetime difference value, or both relative to a reference are essentially non-zero numbers, then the relative response of the luminescence analysis corresponding to the activated catalyst present in the sample may be proportional to the concentration of an activated catalyst in the sample. Accordingly, the measure of the absorbency which represents the active catalyst (e.g., the area under the determined peak in the sample luminescence data plot) may be correlated to the concentration of active catalyst per unit of catalyst system present in the sample by using, for example, Beer's Law:

A=abc, wherein A=Absorbance (area under the curve of a peak in the luminescence data); a is equal to the extinction coefficient of the activated catalyst, b is equal to the optical path length of the sample, and c is equal to the concentration of the sample. Accordingly, a quantitative determination of the concentration of active sites per unit of the catalyst system present in a sample may be made according to the equation:

c=(a*b)/A

As such, a method for quantitatively determining the concentration of an activated catalyst site in a sample comprising a catalyst system comprises determining a total emission intensity value "I" from the sum of a plurality of sample output values which correlate to an essentially non-zero energy value with respect to time (i.e., the area under the emission peak in the luminescence spectrum analysis); determining the concentration of an active catalyst site in the catalyst system present in the sample according to the equation c=(a*b)/I, wherein I is the total emission intensity value, a is the extinction coefficient of the activated catalyst site in the catalyst system, b is a measure of the optical path length of the sample, and c is equal to a concentration of the active catalyst site in the sample comprising the catalyst system.

Accordingly, the presence of an essentially non-zero sample emission energy difference value, sample lifetime value, or both, relative to a reference, when measured according to the method disclosed herein, may provide information as to presence of an activated site in a given catalyst system, the number of active sites for a given catalyst preparation, the presence of a partially activated catalyst site in a particular catalyst system, the number of active sites for a given catalyst preparation within a given catalyst family, the relative activities for two related, similar, and/or identical catalyst compounds prepared using the same and/or different procedures, as well as quantitative data relating to, for example, lot to lot variations of catalysts during a manufacturing process or processes.

Activation Index

Activation of a catalyst or pre-catalyst by an activator may also be determined based on determination utilizing an activation index of the analytes, represented herein by the symbol "$\Omega$". The activation index includes a method to compare the activation state for catalyst systems made using different preparation procedures.

Preferably, the activation state used in this context refers to the molecular structure of a coordination site within the catalyst system, in other words, the presence or not of an activated catalyst site in a catalyst system. For a given catalyst family, such as a specific metallocene and activator, similar activation index values are expected if the same active site is formed under different catalyst preparation procedures. If multiple peaks exist in the time resolved luminescence contour plots for a given catalyst system preparation, more multiple values of the activation index will be calculated. The existence of more than a single activation index calculated from a time resolved luminescence contour plot may also indicate the presence of more than one activation site. In addition, the presence of a peak in the spectrum having an essentially zero activation index along with a peak having an essentially non-zero activation index may indicate a partially activated catalyst system.

In a preferred embodiment, the time dependent luminescence signal, $I_j(t)$, measured at an emission energy, $E_j$, may be fit to the expression:

$$I_j(t) = \sum_i A_{ij} \exp(-t/T_{ij})$$

where $A_{ij}$ is the $i^{th}$ amplitude component for the decay lifetime $T_{ij}$. The two dimensional (2D) time resolved luminescence contour may be a plot of the $A_{ij}$ values with decay lifetimes plotted in ascending order along one axis and emission energy in ascending order plotted along the other axis. A peak in the 2D contour plot can be defined by an $A_{ij}$ which is greater than the next neighbouring $A_{nm}$ where n=i±1, m=j±1. This peak will occur at a given emission energy, $E_{max}$, and a given emission decay lifetime, $T_{max}$. The activation index, $\Omega$, may then be defined by:

$$\Omega = \left(\frac{\log(T_{max}^{unactivated}) - \log(T_{max}^{activated})}{\log(T_{max}^{unactivated})}\right)^2 + \left(\frac{E_{max}^{unactivated} - E_{max}^{activated}}{E_{max}^{unactivated}}\right)^2$$

where $T_{max}$ and $E_{max}$ are respectively the decay lifetime and energy of the peaks for the activated and reference (i.e., unactivated) catalyst system. An activated catalyst is preferably described by an essentially non-zero value of $\Omega$, as described herein, and as demonstrated in the Examples herein. In a preferred embodiment, the activation index, $\Omega$, may be greater than or equal to about 0.001, with and activation index greater than or equal to about 0.01 being more preferred and greater than or equal to about 0.1 being especially preferred.

As discussed above, the time resolved luminescence analysis on an analyte comprises irradiating the analyte with one or more wavelengths of electromagnetic energy; and measuring the time dependence and intensity of an emitted radiation at one or more emission energies. In a preferred embodiment, the analyte is irradiated with electromagnetic energy having a wavelength of about 7000 Å to about 10 Å. Also, the time resolved luminescence analysis on the reference analyte and the time resolved luminescence analysis on the sample analyte are preferably obtained in similar solvents, at similar temperatures, at similar analyte concentrations, at similar impurity concentrations, under similar external conditions, and/or a combination thereof.

As discussed above, the sample emission energy, the sample lifetime, the reference emission energy, the reference lifetime, or a combination thereof are each determined from one or more output values which are greater than or equal to about 2.5 times the signal to noise ratio of the analysis. Furthermore, the activation index may be used as part of a method for determining the number of activated catalytic sites in a catalyst system comprising the above described method, wherein a determination of a plurality of sample emission energies and a plurality of sample lifetimes each individually associated with a particular maximum emission intensity in the sample output values is made, followed by determining the activation index Ω for each of the sample emission energies and their corresponding sample lifetimes wherein each essentially non-zero activation index Ω represent an active catalyst site in the catalyst system, such that a determination of the number of active catalyst sites in the catalyst system (i.e., those having an essentially non-zero activation index) can be made.

The presence of a partially activated catalyst site in a catalyst system may also be made using the activation index. As provided for above a plurality of sample emission energies and a plurality of sample lifetimes each individually associated with a particular maximum emission intensity in the sample output values are determined, followed by determining the activation index Ω for each of the sample emission energies and their corresponding sample lifetimes wherein each essentially non-zero activation index Ω represent an active catalyst site in the catalyst system. Each essentially zero activation index value may represent a partially activated catalyst site in the catalyst system, such that the presence of a partially activated catalyst site in the catalyst system may be determined.

The concentration of an active catalyst site in a catalyst system may also be determined, wherein the sum of a plurality of sample output values which correlate to an essentially non-zero activation index are utilized as described above.

Catalyst Systems

Catalyst systems suitable for use herein include a catalyst compound and/or combination of a catalyst precursor and an activator. A catalyst system may also comprise one or more supports. The activator may also be combined with a support forming a support bound activator, preferably wherein the catalyst is combined with the activator forming a supported catalyst system.

Catalyst and Pre-Catalyst Compounds

Any pre-catalyst compound (also referred to as a catalyst precursor), which emits a luminescent spectrum, may be used in the practice of this invention. Catalysts and/or catalyst precursors suitable for use herein include anionic catalysts, anionic catalyst precursors, cationic catalysts, cationic catalyst precursors, free radical catalysts, free radical catalyst precursors, coordination catalysts coordination catalyst precursors, condensation catalysts, condensation catalyst precursors, zeolites comprising one or more heteroatoms, SHOP catalysts, a SHOP catalyst precursor, an oligomerization catalyst, an oligomerization catalyst precursor, and/or a combination thereof, or the like. Preferred catalyst and catalyst precursors which may be utilized in the process of the invention include metallocene transition metal compounds (containing one, two, or three cyclopentadienyl ligands per metal atom), non-metallocene early transition metal compounds (including those with amide and/or phenoxide type ligands), non-metallocene late transition metal compounds (including those with diimine or diiminepyridyl ligands), and other transition metal compounds.

Metallocene Catalysts and Pre-Catalysts

Metallocene compounds (metallocene catalysts and metallocene catalyst precursors) useful in this invention include half and full sandwich compounds having one or more ligands, also referred to herein as bulky ligands, bonded to at least one metal atom. Typical bulky ligand metallocene compounds may be described as containing one or more bulky ligand(s) and one or more leaving group(s) bonded to at least one metal atom. The bulky ligands may be represented by one or more open, acyclic, or fused ring(s) or ring system(s) or a combination thereof. These bulky ligands, preferably the ring(s) or ring system(s), may be composed of atoms selected from Groups 13 to 16 atoms of the Periodic Table of Elements, preferably the atoms are selected from the group consisting of carbon, nitrogen, oxygen, silicon, sulphur, phosphorous, germanium, boron, aluminum, or a combination thereof. Most preferably, the ring(s) or ring system(s) are composed of carbon atoms such as but not limited to those cyclopentadienyl ligands or cyclopentadienyl-type ligand structures or other similar functioning ligand structure such as a pentadienyl, a cyclooctatetraendiyl, a cyclobutadienyl, or a substituted allyl ligand. Other ligands that can function similarly to a cyclopentadienyl-type ligand include amides, phosphides, imines, phosphinimines, amidinates, and ortho-substituted phenoxides. The metal atom is preferably selected from Groups 3 through 15 and the lanthanide or actinide series of the Periodic Table of Elements. Preferably the metal is a transition metal from Groups 3 through 12, more preferably Groups 4, 5 and 6, and most preferably the transition metal is from Group 4.

In one embodiment, the catalyst composition of the invention includes one or more bulky ligand metallocene catalyst compounds represented by formula (1):

$$L^A L^B M Q^*_n \qquad (1)$$

where M is a metal atom from the Periodic Table of the Elements and may be a Group 3 to 12 metal or from the lanthanide or actinide series of the Periodic Table of Elements, preferably M is a Group 4, 5 or 6 transition metal, more preferably M is a Group 4 transition metal, even more preferably M is zirconium, hafnium or titanium. The bulky ligands, $L^A$ and $L^B$, are open, acyclic or fused ring(s) or ring system(s) and are any ancillary ligand system, including unsubstituted or substituted, cyclopentadienyl ligands or cyclopentadienyl-type ligands, heteroatom substituted and/or heteroatom containing cyclopentadienyl-type ligands. Non-limiting examples of bulky ligands include cyclopentadienyl ligands, cyclopentaphenanthreneyl ligands, indenyl ligands, benzindenyl ligands, fluorenyl ligands, dibenzo[b,h]fluorenyl ligands, benzo[b]fluorenyl ligands, cyclooctatetraendiyl ligands, cyclopentacyclododecene ligands, azenyl ligands, azulene ligands, pentalene ligands, phosphoyl ligands, phosphinimine (WO 99/40125), pyrrolyl ligands, pyrozolyl ligands, carbazolyl ligands, boratobenzene ligands and the like, including hydrogenated versions thereof, for example tetrahydroindenyl ligands. In one embodiment, $L^A$ and $L^B$ may be any other ligand structure capable of π-bonding to M. In yet another embodiment, the atomic molecular weight (MW) of $L^A$ or $L^B$ exceeds 60 a.m.u., preferably greater than 65 a.m.u. In another embodiment, $L^A$ and $L^B$ may comprise one or more heteroatoms, for example, nitrogen, silicon, boron, germanium, sulfur and phosphorous, in combination with carbon atoms to form an open, acyclic, or preferably a fused, ring or ring system, for example, a hetero-cyclopentadienyl ancillary ligand. Other $L^A$ and $L^B$ bulky ligands include but are not limited to bulky amides, phosphides, alkoxides, aryloxides, imides, carbolides, borollides, porphyrins, phthalocyanines, corrins and other polyazomacrocycles. Independently, each $L^A$ and $L^B$ may be the same or different type of bulky ligand that is bonded to M. In one embodiment of Formula 1 only one of either $L^A$ or $L^B$ is present.

Independently, each $L^A$ and $L^B$ may be unsubstituted or substituted with a combination of substituent groups R*. Non-limiting examples of substituent groups R* preferably include one or more from the group selected from hydrogen, or linear or branched alkyl radicals, alkenyl radicals, alkynyl radicals, cycloalkyl radicals, aryl radicals, acyl radicals, aroyl radicals, alkoxy radicals, aryloxy radicals, alkylthio radicals, dialkylamino radicals, alkoxycarbonyl radicals, aryloxycarbonyl radicals, carbomoyl radicals, alkyl- or dialkyl-carbamoyl radicals, acyloxy radicals, acylamino radicals, aroylamino radicals or combination thereof. In a preferred embodiment, substituent groups R* have up to 50 non-hydrogen atoms, preferably from 1 to 30 carbon, that can also be substituted with halogens or heteroatoms or the like. Non-limiting examples of alkyl substituents R* include methyl, ethyl, propyl, butyl, pentyl, hexyl, cyclopentyl, cyclohexyl, benzyl or phenyl groups and the like, including all their isomers, for example tertiary butyl, isopropyl, and the like. Other hydrocarbyl radicals include fluoromethyl, fluoroethyl, difluoroethyl, iodopropyl, bromohexyl, chlorobenzyl and hydrocarbyl substituted organometalloid radicals including trimethylsilyl, trimethylgermyl, methyldiethylsilyl and the like; and halocarbyl-substituted organometalloid radicals including tris(trifluoromethyl)silyl, methyl-bis(difluoromethyl)silyl, bromomethyldimethylgermyl and the like; and disubstituted boron radicals including dimethylboron for example; and disubstituted pnictogen radicals including dimethylamine, dimethylphosphine, diphenylamine, methylphenylphosphine, chalcogen radicals including methoxy, ethoxy, propoxy, phenoxy, methylsulfide and ethylsulfide. Non-hydrogen substituents R* include the atoms carbon, silicon, boron, aluminum, nitrogen, phosphorous, oxygen, tin, sulfur, germanium and the like, including olefins such as but not limited to olefinically unsaturated substituents including vinyl-terminated ligands, for example but-3-enyl, prop-2-enyl, hex-5-enyl and the like. Also, at least two R* groups, preferably two adjacent R groups, are joined to form a ring structure having from 3 to 30 atoms selected from carbon, nitrogen, oxygen, phosphorous, silicon, germanium, aluminum, boron or a combination thereof. Also, a substituent group, R*, may also be a diradical bonded to L at one end and forming a carbon sigma bond to the metal M. Other ligands may be bonded to the metal M, such as at least one leaving group Q*.

In one embodiment, Q* is a monoanionic labile ligand having a sigma-bond to M. Depending on the oxidation state of the metal, the value for n is 0, 1 or 2 such that Formula 1 above represents a neutral bulky ligand metallocene catalyst compound. Non-limiting examples of Q* ligands include weak bases such as amines, phosphines, ethers, carboxylates, dienes, hydrocarbyl radicals having from 1 to 20 carbon atoms, hydrides or halogens and the like or a combination thereof. In another embodiment, two or more Q*'s form a part of a fused ring or ring system. Other examples of Q* ligands include those substituents for R* as described above and including cyclobutyl, cyclohexyl, heptyl, tolyl, trifluoromethyl, tetramethylene (both Q*), pentamethylene (both Q*), methylidene (both Q*), methoxy, ethoxy, propoxy, phenoxy, bis(N-methylanilide), dimethylamide, dimethylphosphide radicals and the like.

In another embodiment, the catalyst composition of the invention may include one or more bulky ligand metallocene catalyst compounds where $L^A$ and $L^B$ of Formula 1 are bridged to each other by at least one bridging group, A*, as represented by Formula 2.

$$L^A A^* L^B M Q^*_n \qquad (2)$$

The compounds of Formula 2 may be referred to as bridged, bulky ligand metallocene catalyst compounds. $L^A$, $L^B$, M, Q* and n are as defined above. Non-limiting examples of bridging group A* include bridging groups containing at least one Group 13 to 16 atom, often referred to as a divalent moiety such as but not limited to at least one of a carbon, oxygen, nitrogen, silicon, aluminum, boron, germanium and tin atom or a combination thereof. Preferably bridging group A* contains a carbon, silicon or germanium atom, most preferably A* contains at least one silicon atom or at least one carbon atom. The bridging group A* may also contain substituent groups R* as defined above including halogens and iron. Non-limiting examples of bridging group A* may be represented by R'$_2$C, R'$_2$CCR'$_2$, R'$_2$Si, R'$_2$SiCR'$_2$, R'$_2$SiSiR'$_2$ R'$_2$Ge, R'P, R'N, R'B where R' is independently, a radical group which is hydride, hydrocarbyl, substituted hydrocarbyl, halocarbyl, substituted halocarbyl, hydrocarbyl-substituted organometalloid, halocarbyl-substituted organometalloid, disubstituted boron, disubstituted pnictogen, substituted chalcogen, or halogen or two or more R' may be joined to form a ring or ring system. In one embodiment, the bridged, bulky ligand metallocene catalyst compounds of Formula 2 have two or more bridging groups A* (EP 664 301 B1). In another embodiment, the bulky ligand metallocene catalyst compounds are those where the R* substituents on the bulky ligands $L^A$ and $L^B$ of Formulas 1 and 2 are substituted with the same or different number of substituents on each of the bulky ligands. In another embodiment, the bulky ligands $L^A$ and $L^B$ of Formulas 1 and 2 are different from each other.

Other bulky ligand metallocene catalyst compounds and catalyst systems useful in the invention may include those described in U.S. Pat. Nos. 5,064,802, 5,145,819, 5,149,819, 5,243,001, 5,239,022, 5,276,208, 5,296,434, 5,321,106, 5,329,031, 5,304,614, 5,677,401, 5,723,398, 5,753,578, 5,854,363, 5,856,547 5,858,903, 5,859,158, 5,900,517 and 5,939,503 and PCT publications WO 93/08221, WO 93/08199, WO 95/07140, WO 98/11144, WO 98/41530, WO 98/41529, WO 98/46650, WO 99/02540 and WO 99/14221 and European publications EP-A-0 578 838, EP-A-0 638 595, EP-B-0 513 380, EP-A1-0 816 372, EP-A2-0 839 834, EP-B1-0 632 819, EP-B1-0 748 821 and EP-B1-0 757 996, all of which are herein fully incorporated by reference.

In another embodiment, the catalyst compositions of the invention may include bridged heteroatom, mono-bulky ligand metallocene compounds. These types of catalysts and catalyst systems are described in, for example, PCT publication WO 92/00333, WO 94/07928, WO 91/04257, WO 94/03506, WO96/00244, WO 97/15602 and WO 99/20637 and U.S. Pat. Nos. 5,057,475, 5,096,867, 5,055,438, 5,198, 401, 5,227,440 and 5,264,405 and European publication EP-A-0 420 436, all of which are herein fully incorporated by reference.

In another embodiment, the catalyst composition of the invention includes one or more bulky ligand metallocene catalyst compounds represented by Formula 3:

$$L^C A^* J^* M Q^*_n \qquad (3)$$

where M is a Group 3 to 16 metal atom or a metal selected from the Group of actinides and lanthanides of the Periodic Table of Elements, preferably M is a Group 3 to 12 transition metal, and more preferably M is a Group 4, 5 or 6 transition metal, and most preferably M is a Group 4 transition metal in any oxidation state, and is especially titanium; $L^C$ is a substituted or unsubstituted bulky ligand bonded to M; J* is bonded to M; A* is bonded to J* and LC; J* is a heteroatom ancillary ligand; and A* is a bridging group; Q* is a univalent anionic ligand; and n is the integer 0, 1 or 2. In Formula 3 above, $L^C$, A* and J* form a fused ring system. In an embodiment, $L^C$ of Formula 3 is as defined above for $L^A$. A*, M and Q* of Formula 3 are as defined above in Formula 1. In Formula 3, J* is a heteroatom containing ligand in which J* is an element with a coordination number of three from Group 15 or an element with a coordination number of two from Group 16 of the Periodic Table of Elements. Preferably J* contains a nitrogen, phosphorus, oxygen or sulfur atom with nitrogen being most preferred. In an embodiment of the invention, the bulky ligand metallocene catalyst compounds are heterocyclic ligand complexes where the bulky ligands, the ring(s) or ring system(s), include one or more heteroatoms or a combination thereof. Non-limiting examples of heteroatoms include a Group 13 to 16 element, preferably nitrogen, boron, sulfur, oxygen, aluminum, silicon, phosphorous and tin. Examples of these bulky ligand metallocene catalyst compounds are described in WO 96/33202, WO 96/34021, WO 97/17379 and WO 98/22486 and EP-A1-0 874 005 and U.S. Pat. Nos. 5,637,660, 5,539,124, 5,554,775, 5,756,611, 5,233,049, 5,744,417, and 5,856,258 all of which are herein incorporated by reference.

In one embodiment, the bulky ligand metallocene compounds (pre-catalysts) are those complexes based on bidentate ligands containing pyridine or quinoline moieties, such as those described in U.S. application Ser. No. 09/103,620 filed Jun. 23, 1998, which is herein incorporated by reference. In another embodiment, the bulky ligand metallocene catalyst compounds are those described in PCT publications WO 99/01481 and WO 98/42664, which are fully incorporated herein by reference.

In another embodiment, the bulky ligand metallocene catalyst compound is a complex of a metal, preferably a transition metal, a bulky ligand, preferably a substituted or unsubstituted pi-bonded ligand, and one or more heteroallyl moieties, such as those described in U.S. Pat. Nos. 5,527,752 and 5,747,406 and EP-B1-0 735 057, all of which are herein fully incorporated by reference.

In another embodiment, the bulky ligand metallocene catalyst compounds are those described in PCT publications WO 99/01481 and WO 98/42664, which are fully incorporated herein by reference. Useful Group 6 bulky ligand metallocene catalyst systems are described in U.S. Pat. No. 5,942,462, which is incorporated herein by reference.

Still other useful catalysts include those multinuclear metallocene catalysts as described in WO 99/20665 and Pat. No. 6,010,794, and transition metal metaaracyle structures described in EP 0 969 101 A2, which are herein incorporated herein by reference. Other metallocene catalysts include those described in EP 0 950 667 A1, double cross-linked metallocene catalysts (EP 0 970 074 A1), tethered metallocenes (EP 970 963 A2) and those sulfonyl catalysts described in U.S. Pat. No. 6,008,394, which are incorporated herein by reference.

It is also contemplated that in one embodiment, the bulky ligand metallocene catalysts as described above, include their structural or optical or enantiomeric isomers (meso and racemic isomers, for example see U.S. Pat. No. 5,852,143, incorporated herein by reference) and mixtures thereof.

It is further contemplated that any one of the bulky ligand metallocene catalyst compounds, described above, have at least one fluoride or fluorine containing leaving group as described in U.S. application Ser. No. 09/191,916 filed Nov. 13, 1998.

Preferred metallocene catalysts for use herein may also be represented by one of the following general formulae:

$$\{[(A-Cp)MX_1]^+\}_d\{[B']^{d-}\} \quad (4)$$

$$\{[(A-Cp)MX_1L]^+\}_d\{[B']^{d-}\} \quad (5)$$

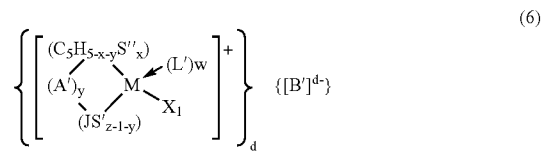

(6)

wherein:
(A-Cp) is preferably (Cp), (Cp*) or Cp-A'-Cp*; Cp and Cp* are the same or different cyclopentadienyl rings substituted with from zero to five substituent groups S", each substituent group S" being, independently, a radical group which is a hydrocarbyl, substituted-hydrocarbyl, halocarbyl, substituted-halocarbyl, hydrocarbyl-substituted organometalloid, halocarbyl-substituted organometalloid, disubstituted boron, disubstituted pnictogen, substituted chalcogen or halogen radicals, or Cp and Cp* are cyclopentadienyl rings in which any two adjacent S" groups are joined forming a $C_4$ to $C_{20}$ ring to give a saturated or unsaturated polycyclic cyclopentadienyl ligand; Cp and Cp* may also have one or two carbon atoms within the ring replaced by a Group 15 or 16 element especially, S, O, N or P;
A' is a bridging group;
$(C_5H_{5-y-x}S''_x)$ is a cyclopentadienyl ring substituted with from zero to five S" radicals as defined above;
x is from 0 to 5 denoting the degree of substitution;
M is titanium, zirconium or hafnium;
$X_1$ is a hydride radical, hydrocarbyl radical, substituted-hydrocarbyl radical, hydrocarbyl-substituted organometalloid radical or halocarbyl-substituted organometalloid radical which radical may optionally be covalently bonded to both or either M and L or L' or all or any M, S" or S', and provided that $X_1$ is not a substituted or unsubstituted cyclopentadienyl ring;
$(JS'_{z-1-y})$ is a heteroatom ligand in which J is an element from Group 15 of the Periodic Table of Elements with a coordination number of 3 or an element from Group 16 with a coordination number of 2; S' is a radical group which is a hydrocarbyl, substituted hydrocarbyl, halocarbyl, substituted halocarbyl, hydrocarbyl-substituted organometalloid, or halocarbyl-substituted organometalloid; and z is the coordination number of the element J;
y is 0 or 1;
L is an olefin, diolefin or aryne ligand. L' is the same as L, and can additionally be an amine, phosphine, ether, or sulfide ligand, or any other neutral Lewis base; L' can also be a second transition metal compound of the same type such that the two metal center M and M* are bridged by $X_1$ and $X'_1$, wherein M* has the same meaning as M, $X'_1$, $X_2$ and $X'_2$ have the same meaning as $X_1$, where such dimeric compounds which are precursors to the cationic portion of the catalyst are represented by the formula:

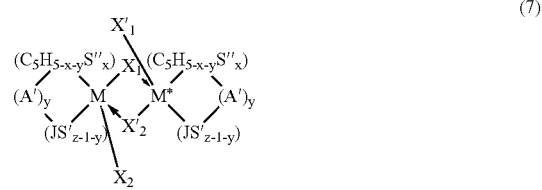

(7)

wherein w is an integer from 0 to 3;

B' is a chemically stable, non-nucleophilic anionic complex having a molecular diameter about or greater than 4 angstroms or an anionic Lewis-acid activator resulting from the reaction of a Lewis-acid activator with the precursor to the cationic portion of the catalyst system described in formulae 1-4. When B' is a Lewis-acid activator, $X_1$ can also be an alkyl group donated by the Lewis-acid activator; and d is an integer representing the charge of B'.

Group 4 metal compounds; i.e., titanium, zirconium and hafnium metallocene compounds, useful in the preparation of preferred metallocene catalysts include cyclopentadienyl derivatives of titanium, zirconium and hafnium. Useful titanocenes, zirconocenes and hafnocenes may be represented by the following general formulae:

$$(A\text{-}Cp)MX_1X_2 \quad (8)$$

$$(A\text{-}Cp)ML \quad (9)$$

$$(10)$$

wherein:

(A-Cp) is either (Cp)(Cp*) or Cp-A'-Cp*; Cp and Cp* are the same or different cyclopentadienyl rings substituted with from zero to five substituent groups S", each substituent group S" being, independently, a radical group which is a hydrocarbyl, substituted-hydrocarbyl, halocarbyl, substituted-halocarbyl, hydrocarbyl-substituted organometalloid, halocarbyl-substituted organometalloid, disubstituted boron, disubstituted pnictogen, substituted chalcogen or halogen radicals, or Cp and Cp* are cyclopentadienyl rings in which any two adjacent S" groups are joined forming a $C_4$ to $C_{20}$ ring to give a saturated or unsaturated polycyclic cyclopentadienyl ligand;

A' is a bridging group;

y is 0 or 1;

$(C_5H_{5-y-x}S''_x)$ is a cyclopentadienyl ring substituted with from zero to five S" radicals as defined above;

x is from 0 to 5 denoting the degree of substitution;

$(JS'_{z-1-y})$ is a heteroatom ligand in which J is an element from Group 15 of the Periodic Table of Elements with a coordination number of 3 or an element from Group 16 with a coordination number of 2, S' is a radical group which is a hydrocarbyl, substituted hydrocarbyl, halocarbyl, substituted halocarbyl, hydrocarbyl-substituted organometalloid, or halocarbyl-substituted organometalloid; and z is the coordination number of the element J;

L is an olefin, diolefin or aryne ligand. L' is the same as L and can additionally be an amine, phosphine, ether, or sulfide ligand, or any other neutral Lewis base; L' can also be a second transition metal compound of the same type such that the two metal centers M and M* are bridged by $X_1$ and $X'_1$, wherein M* has the same meaning as M, $X'_1$ has the same meaning as $X_1$ and $X'_2$ has the same meaning as $X_2$ where such dimeric compounds which are precursors to the cationic portion of the catalyst are represented by formula 7 above;

w is an integer from 0 to 3; and $X_1$ and $X_2$ are, independently, hydride radicals, hydrocarbyl radicals, substituted hydrocarbyl radicals, halocarbyl radicals, substituted halocarbyl radicals, and hydrocarbyl- and halocarbyl-substituted organometalloid radicals, substituted pnictogen radicals, or substituted chalcogen radicals; or $X_1$ and $X_2$ are joined and bound to the metal atom to form a metallacycle ring containing from about 3 to about 20 carbon atoms; or $X_1$ and $X_2$ together can be an olefin, diolefin or aryne ligand; or when Lewis-acid activators, such as methylalumoxane, which are capable of donating an $X_1$ ligand as described above to the transition metal component are used, $X_1$ and $X_2$ may independently be a halogen, alkoxide, aryloxide, amide, phosphide or other univalent anionic ligand or both $X_1$ and $X_2$ can also be joined to form a anionic chelating ligand and with the proviso that $X_1$ and $X_2$ are not a substituted or unsubstituted cyclopentadienyl ring.

Preferred metallocene precatalysts include:

dimethylsiladiyl(2-methyl-4-phenylindenyl)$_2$metal dichloride;

dimethylsiladiyl(2-methyl-4-phenylindenyl)$_2$metal dimethyl;

dimethylsiladiyl(2-methyl indenyl)$_2$metal dichloride;

dimethylsiladiyl(2-methyl indenyl)$_2$metal dimethyl;

dimethylsiladiyl(indenyl)$_2$metal dichloride;

dimethylsiladiyl(indenyl)$_2$metal dimethyl;

dimethylsiladiyl(tetrahydroindenyl)$_2$metal dichloride;

dimethylsiladiyl(tetrahydroindenyl)$_2$metal dimethyl;

dimethylsiladiyl(indenyl)$_2$metal diethyl;

diphenylsiladiyl(indenyl)$_2$metal dimethyl;

dimethylsiladiyl(2-methyl, 4-[3',5'-di-tbutylphenyl]indenyl)$_2$metal dichloride;

dimethylsiladiyl(2-methyl, 4-[3',5'-di-tbutylphenyl]indenyl)$_2$metal dimethyl;

dimethylsiladiyl(2-ethyl, 4-[3',5'-di-tbutylphenyl]indenyl)$_2$metal dichloride;

dimethylsiladiyl(2-ethyl, 4-[3',5'-di-tbutylphenyl]indenyl)$_2$metal dimethyl;

dimethylsiladiyl(2-n-propyl, 4-[3',5'-di-tbutylphenyl]indenyl)$_2$metal dichloride;

dimethylsiladiyl(2-n-propyl, 4-[3',5'-di-tbutylphenyl]indenyl)$_2$metal dimethyl;

dimethylsiladiyl(2-iso-propyl, 4-[3',5'-di-tbutylphenyl]indenyl)$_2$metal dichloride;

dimethylsiladiyl(2-iso-propyl, 4-[3',5'-di-tbutylphenyl]indenyl)$_2$metal dimethyl;

dimethylsiladiyl(2-n-butyl, 4-[3',5'-di-tbutylphenyl]indenyl)$_2$metal dichloride;

dimethylsiladiyl(2-n-butyl, 4-[3',5'-di-tbutylphenyl]indenyl)$_2$metal dimethyl;

dimethylsiladiyl(2-iso-butyl, 4-[3',5'-di-tbutylphenyl]indenyl)$_2$metal dichloride;

dimethylsiladiyl(2-iso-butyl, 4-[3',5'-di-tbutylphenyl]indenyl)$_2$metal dimethyl;

dimethylsiladiyl(2-sec-butyl, 4-[3',5'-di-tbutylphenyl]indenyl)$_2$metal dichloride;

dimethylsiladiyl(2-sec-butyl, 4-[3',5'-di-tbutylphenyl]indenyl)$_2$metal dimethyl;

dimethylsiladiyl(2-methyl, 4-[3',5'-di-phenylphenyl]indenyl)$_2$metal dichloride;

dimethylsiladiyl(2-methyl, 4-[3',5'-di-phenylphenyl]indenyl)$_2$metal dimethyl;

dimethylsiladiyl(2-ethyl, 4-[3',5'-di-phenylphenyl]indenyl)$_2$metal dichloride;

dimethylsiladiyl(2-ethyl, 4-[3',5'-di-phenylphenyl]indenyl)$_2$metal dimethyl;

dimethylsiladiyl(2-n-propyl, 4-[3',5'-di-phenylphenyl]indenyl)₂metal dichloride;
dimethylsiladiyl(2-n-propyl, 4-[3',5'-di-phenylphenyl]indenyl)₂metal dimethyl;
dimethylsiladiyl(2-iso-propyl, 4-[3',5'-di-phenylphenyl]indenyl)₂metal dichloride;
dimethylsiladiyl(2-iso-propyl, 4-[3',5'-di-phenylphenyl]indenyl)₂metal dimethyl;
dimethylsiladiyl(2-n-butyl, 4-[3',5'-di-phenylphenyl]indenyl)₂metal dichloride;
dimethylsiladiyl(2-n-butyl, 4-[3',5'-di-phenylphenyl]indenyl)₂metal dimethyl;
dimethylsiladiyl(2-iso-butyl, 4-[3',5'-di-phenylphenyl]indenyl)₂metal dichloride;
dimethylsiladiyl(2-iso-butyl, 4-[3',5'-di-phenylphenyl]indenyl)₂metal dimethyl;
dimethylsiladiyl(2-sec-butyl, 4-[3',5'-di-phenylphenyl]indenyl)₂metal dichloride;
dimethylsiladiyl(2-sec-butyl, 4-[3',5'-di-phenylphenyl]indenyl)₂metal dimethyl;
dimethylsiladiyl(2-tert-butyl, 4-[3',5'-di-phenylphenyl]indenyl)₂metal dichloride;
dimethylsiladiyl(2-tert-butyl, 4-[3',5'-di-phenylphenyl]indenyl)₂metal dimethyl;
9-silafluorendiyl(2-methyl, 4-[3',5'-di-tbutylphenyl]indenyl)₂metal dichloride;
9-silafluorendiyl(2-methyl, 4-[3',5'-di-tbutylphenyl]indenyl)₂metal dimethyl;
9-silafluorendiyl(2-ethyl, 4-[3',5'-di-tbutylphenyl]indenyl)₂metal dichloride;
9-silafluorendiyl(2-ethyl, 4-[3',5'-di-tbutylphenyl]indenyl)₂metal dimethyl;
9-silafluorendiyl(2-n-propyl, 4-[3',5'-di-tbutylphenyl]indenyl)₂metal dichloride;
9-silafluorendiyl(2-n-propyl, 4-[3',5'-di-tbutylphenyl]indenyl)₂metal dimethyl;
9-silafluorendiyl(2-iso-propyl, 4-[3¹,5'-di-tbutylphenyl]indenyl)₂metal dichloride;
9-silafluorendiyl(2-iso-propyl, 4-[3¹,5'-di-tbutylphenyl]indenyl)₂metal dimethyl;
9-silafluorendiyl(2-n-butyl, 4-[3',5'-di-tbutylphenyl]indenyl)₂metal dichloride;
9-silafluorendiyl(2-n-butyl, 4-[3',5'-di-tbutylphenyl]indenyl)₂metal dimethyl;
9-silafluorendiyl(2-iso-butyl, 4-[3',5'-di-tbutylphenyl]indenyl)₂metal dichloride;
9-silafluorendiyl(2-iso-butyl, 4-[3',5'-di-tbutylphenyl]indenyl)₂metal dimethyl;
9-silafluorendiyl(2-sec-butyl, 4-[3',5'-di-tbutylphenyl]indenyl)₂metal dichloride;
9-silafluorendiyl(2-sec-butyl, 4-[3',5'-di-tbutylphenyl]indenyl)₂metal dimethyl;
9-silafluorendiyl(2-tert-butyl, 4-[3',5'-di-tbutylphenyl]indenyl)₂metal dichloride;
9-silafluorendiyl(2-tert-butyl, 4-[3',5'-di-tbutylphenyl]indenyl)₂metal dimethyl;

wherein the metal can be chosen from Zr, Hf, or Ti, preferably Zr.

Illustrative, but not limiting examples of preferred non-stereospecific metallocene catalysts are:
[dimethylsilanediyl(tetramethylcyclopentadienyl)(cyclododecylamido)]metal dihalide;
[dimethylsilanediyl(tetramethylcyclopentadienyl)(t-butylamido)]metal dihalide; and
[dimethylsilanediyl(tetramethylcyclopentadienyl)(exo-2-norbornyl)]metal dichalide;

wherein the metal can chosen from Zr, Hf, or Ti, preferably Ti and the halide is preferably chlorine.

Particularly preferred compounds include:
dimethylsiladiyl(tetramethylcyclopentadienyl)(cyclododecylamido) titanium dichloride;
dimethylsiladiyl(tetramethylcyclopentadienyl)(cyclohexylamido) titanium dichloride,
dimethylsiladiyl(tetramethylcyclopentadienyl)(1-adamantylamido) titanium dichloride,
dimethylsiladiyl(tetramethylcyclopentadienyl)(t-butylamido) titanium dichloride,
dimethylsiladiyl(tetramethylcyclopentadienyl)(s-butylamido) titanium dichloride,
dimethylsiladiyl(tetramethylcyclopentadienyl)(n-butylamido) titanium dichloride,
dimethylsiladiyl(tetramethylcyclopentadienyl)(exo-2-norbornylamido) titanium dichloride,
diethylsilyl(tetramethylcyclopentadienyl)(cyclododecylamido) titanium dichloride,
diethylsilyl(tetramethylcyclopentadienyl)(exo-2-norbornylamido) titanium dichloride,
diethylsilyl(tetramethylcyclopentadienyl)(cyclohexylamido) titanium dichloride,
diethylsilyl(tetramethylcyclopentadienyl)(1-adamantylamido) titanium dichloride,
methylene(tetramethylcyclopentadienyl)(cyclododecylamido) titanium dichloride,
methylene(tetramethylcyclopentadienyl)(exo-2-norbornylamido) titanium dichloride, methylene(tetramethylcyclopentadienyl)(cyclohexylamido) titanium dichloride,
methylene(tetramethylcyclopentadienyl)(1-adamantylamido) titanium dichloride,
dimethylsiladiyl(tetramethylcyclopentadienyl)(cyclododecylamido) titanium dimethyl,
dimethylsiladiyl(tetramethylcyclopentadienyl)(exo-2-norbornylamido) titanium dimethyl,
dimethylsiladiyl(tetramethylcyclopentadienyl)(cyclohexylamido) titanium dimethyl,
dimethylsiladiyl(tetramethylcyclopentadienyl)(1-adamantylamido) titanium dimethyl,
dimethylsiladiyl(2,5-dimethylcyclopentadienyl)(cyclododecylamido) titanium dichloride,
dimethylsiladiyl(2,5-dimethylcyclopentadienyl)(exo-2-norbornylamido) titanium dichloride,
dimethylsiladiyl(2,5-dimethylcyclopentadienyl)(cyclohexylamido) titanium dichloride,
dimethylsiladiyl(2,5-dimethylcyclopentadienyl)(1-adamantylamido) titanium dichloride,
dimethylsiladiyl(3,4-dimethylcyclopentadienyl)(cyclododecylamido) titanium dichloride,
dimethylsiladiyl(3,4-dimethylcyclopentadienyl)(exo-2-norbornylamido) titanium dichloride,
dimethylsiladiyl(3,4-dimethylcyclopentadienyl)(cyclohexylamido) titanium dichloride,
dimethylsiladiyl(3,4-dimethylcyclopentadienyl)(1-adamantylamido) titanium dichloride,
dimethylsiladiyl(2-ethyl-5-methylcyclopentadienyl)(cyclododecylamido)titanium dichloride,
dimethylsiladiyl(2-ethyl-5-methylcyclopentadienyl)(exo-2-norbornylamido) titanium dichloride, dimethylsiladiyl(2-ethyl-5-methylcyclopentadienyl)(cyclohexylamido) titanium dichloride,
dimethylsiladiyl(2-ethyl-5-methylcyclopentadienyl)(1-adamantylamido) titanium dichloride,
dimethylsiladiyl(3-ethyl-4-methylcyclopentadienyl)(cyclododecylamido)titanium dichloride, dimethylsiladiyl(3-ethyl-4-methylcyclopentadienyl)(exo-2-norbornylamido) titanium dichloride,
dimethylsiladiyl(3-ethyl-4-methylcyclopentadienyl)(cyclohexylamido) titanium dichloride,
dimethylsiladiyl(3-ethyl-4-methylcyclopentadienyl)(1-adamantylamido) titanium dichloride,
dimethylsiladiyl(2-ethyl-3-hexyl-5-methyl-4-octylcyclopentadienyl)(cyclododecylamido) titanium dichloride,
dimethylsiladiyl(2-ethyl-3-hexyl-5-methyl-4-octylcyclopentadienyl)(exo-2-norbornylamido) titanium dichloride,
dimethylsiladiyl(2-ethyl-3-hexyl-5-methyl-4-octylcyclopentadienyl)(cyclohexylamido) titanium dichloride,
dimethylsiladiyl(2-ethyl-3-hexyl-5-methyl-4-octylcyclopentadienyl)(1-adamantylamido) titanium dichloride,
dimethylsiladiyl(2-tetrahydroindenyl)(cyclododecylamido) titanium dichloride,
dimethylsiladiyl(2-tetrahydroindenyl)(cyclohexylamido) titanium dichloride,
dimethylsiladiyl(2-tetrahydroindenyl)(1-adamantylamido) titanium dichloride, and
dimethylsiladiyl(2-tetrahydroindenyl)(exo-2-norbornylamido) titanium dichloride.

In addition preferred species include the dialkyl versions (such as dimethylated versions) of the above compounds, i.e. titanium dimethyl instead of titanium dichloride.

Additional preferred compounds include:
dimethylsiladiyl(2-methyl, 4-[3',5'-di-tbutylphenyl]indenyl)$_2$zirconium dichloride;
dimethylsiladiyl(2-ethyl, 4-[3',5'-di-tbutylphenyl]indenyl)$_2$zirconium dichloride;
dimethylsiladiyl(2-n-propyl, 4-[3',5'-di-tbutylphenyl]indenyl)$_2$zirconium dichloride;
dimethylsiladiyl(2-iso-propyl, 4-[3',5'-di-tbutylphenyl]indenyl)$_2$zirconium dichloride;
dimethylsiladiyl(2-n-butyl, 4-[3',5'-di-tbutylphenyl]indenyl)$_2$zirconium dichloride;
dimethylsiladiyl(2-iso-butyl, 4-[3',5'-di-tbutylphenyl]indenyl)$_2$zirconium dichloride;
dimethylsiladiyl(2-sec-butyl, 4-[3',5'-di-tbutylphenyl]indenyl)$_2$zirconium dichloride;
dimethylsiladiyl(2-tert-butyl, 4-[3',5'-di-tbutylphenyl]indenyl)$_2$zirconium dichloride;
dimethylsiladiyl(2-methyl, 4-[3',5'-di-tbutylphenyl]indenyl)$_2$hafnium dichloride;
dimethylsiladiyl(2-ethyl, 4-[3',5'-di-tbutylphenyl]indenyl)$_2$hafnium dichloride;
dimethylsiladiyl(2-n-propyl, 4-[3',5'-di-tbutylphenyl]indenyl)$_2$hafnium dimethylsiladiyl(2-iso-propyl, 4-[3',5'-di-tbutylphenyl]indenyl)$_2$hafnium dichloride;
dimethylsiladiyl(2-butyl, 4-[3',5'-di-tbutylphenyl]indenyl)$_2$hafnium dichloride;
9-silafluorendiyl(2-methyl, 4-[3',5'-di-tbutylphenyl]indenyl)$_2$zirconium dichloride;
9-silafluorendiyl(2-ethyl, 4-[3',5'-di-tbutylphenyl]indenyl)$_2$zirconium dichloride;
9-silafluorendiyl(2-n-propyl, 4-[3',5'-di-tbutylphenyl]indenyl)$_2$zirconium dichloride;
9-silafluorendiyl(2-iso-propyl, 4-[3',5'-di-tbutylphenyl]indenyl)$_2$zirconium dichloride;
9-silafluorendiyl(2-n-butyl, 4-[3',5'-di-tbutylphenyl]indenyl)$_2$zirconium dichloride;
9-silafluorendiyl(2-iso-butyl, 4-[3',5'-di-tbutylphenyl]indenyl)$_2$zirconium dichloride;
9-silafluorendiyl(2-sec-butyl, 4-[3',5'-di-tbutylphenyl]indenyl)$_2$zirconium dichloride;
9-silafluorendiyl(2-tert-butyl, 4-[3',5'-di-tbutylphenyl]indenyl)$_2$zirconium dichloride;
9-silafluorendiyl(2-methyl, 4-[3',5'-di-tbutylphenyl]indenyl)$_2$hafnium dichloride;
9-silafluorendiyl(2-ethyl, 4-[3',5'-di-tbutylphenyl]indenyl)$_2$hafnium dichloride;
9-silafluorendiyl(2-n-propyl, 4-[3',5'-di-tbutylphenyl]indenyl)$_2$hafnium dichloride;
9-silafluorendiyl(2-iso-propyl, 4-[3',5'-di-tbutylphenyl]indenyl)$_2$hafnium dichloride;
9-silafluorendiyl(2-n-butyl, 4-[3',5'-di-tbutylphenyl]indenyl)$_2$hafnium dichloride;
9-silafluorendiyl(2-iso-butyl, 4-[3',5'-di-tbutylphenyl]indenyl)$_2$hafnium dichloride;
9-silafluorendiyl(2-sec-butyl, 4-[3',5'-di-tbutylphenyl]indenyl)$_2$hafnium dichloride;
9-silafluorendiyl(2-tert-butyl, 4-[3',5'-di-tbutylphenyl]indenyl)$_2$hafnium dichloride;
dimethylsiladiyl(2-methyl, 4-[3',5'-di-tbutylphenyl]indenyl)$_2$zirconium dimethyl;
dimethylsiladiyl(2-ethyl, 4-[3',5'-di-tbutylphenyl]indenyl)$_2$zirconium dimethyl;
dimethylsiladiyl(2-n-propyl, 4-[3',5'-di-tbutylphenyl]indenyl)$_2$zirconium dimethyl;
dimethylsiladiyl(2-iso-propyl, 4-[3',5'-di-tbutylphenyl]indenyl)$_2$zirconium dimethyl;
dimethylsiladiyl(2-n-butyl, 4-[3',5'-di-tbutylphenyl]indenyl)$_2$zirconium dimethyl;
dimethylsiladiyl(2-iso-butyl, 4-[3',5'-di-tbutylphenyl]indenyl)$_2$zirconium dimethyl;
dimethylsiladiyl(2-sec-butyl, 4-[3',5'-di-tbutylphenyl]indenyl)$_2$zirconium dimethyl;
dimethylsiladiyl(2-tert-butyl, 4-[3',5'-di-tbutylphenyl]indenyl)$_2$zirconium dimethyl;
dimethylsiladiyl(2-methyl, 4-[3',5'-di-tbutylphenyl]indenyl)$_2$hafnium dimethyl;
dimethylsiladiyl(2-ethyl, 4-[3',5'-di-tbutylphenyl]indenyl)$_2$hafnium dimethyl;
dimethylsiladiyl(2-n-propyl, 4-[3',5'-di-tbutylphenyl]indenyl)$_2$hafnium dimethyl dimethylsiladiyl(2-iso-propyl, 4-[3',5'-di-tbutylphenyl]indenyl)$_2$hafnium dimethyl;
dimethylsiladiyl(2-n-butyl, 4-[3',5'-di-tbutylphenyl]indenyl)$_2$hafnium dimethyl;
dimethylsiladiyl(2-iso-butyl, 4-[3',5'-di-tbutylphenyl]indenyl)$_2$hafnium dimethyl;
dimethylsiladiyl(2-sec-butyl, 4-[3',5'-di-tbutylphenyl]indenyl)$_2$hafnium dimethyl;
dimethylsiladiyl(2-tert-butyl, 4-[3',5'-di-tbutylphenyl]indenyl)$_2$hafnium dimethyl;
9-silafluorendiyl(2-methyl, 4-[3',5'-di-tbutylphenyl]indenyl)$_2$zirconium dimethyl;
9-silafluorendiyl(2-ethyl, 4-[3',5'-di-tbutylphenyl]indenyl)$_2$zirconium dimethyl;
9-silafluorendiyl(2-n-propyl, 4-[3',5'-di-tbutylphenyl]indenyl)$_2$zirconium dimethyl;
9-silafluorendiyl(2-iso-propyl, 4-[3',5'-di-tbutylphenyl]indenyl)$_2$zirconium dimethyl;
9-silafluorendiyl(2-n-butyl, 4-[3',5'-di-tbutylphenyl]indenyl)$_2$zirconium dimethyl;
9-silafluorendiyl(2-iso-butyl, 4-[3',5'-di-tbutylphenyl]indenyl)$_2$zirconium dimethyl;
9-silafluorendiyl(2-sec-butyl, 4-[3',5'-di-tbutylphenyl]indenyl)$_2$zirconium dimethyl;
9-silafluorendiyl(2-tert-butyl, 4-[3',5'-di-tbutylphenyl]indenyl)$_2$zirconium dimethyl;
9-silafluorendiyl(2-methyl, 4-[3',5'-di-tbutylphenyl]indenyl)$_2$hafnium dimethyl;

9-silafluorendiyl(2-ethyl, 4-[3',5'-di-tbutylphenyl]indenyl)₂hafnium dimethyl;
9-silafluorendiyl(2-n-propyl, 4-[3',5'-di-tbutylphenyl]indenyl)₂hafnium dimethyl;
9-silafluorendiyl(2-iso-propyl, 4-[3',5'-di-tbutylphenyl]indenyl)₂hafnium dimethyl;
9-silafluorendiyl(2-n-butyl, 4-[3',5'-di-tbutylphenyl]indenyl)₂hafnium dimethyl;
9-silafluorendiyl(2-iso-butyl, 4-[3',5'-di-tbutylphenyl]indenyl)₂hafnium dimethyl;
9-silafluorendiyl(2-sec-butyl, 4-[31,5'-di-tbutylphenyl]indenyl)₂hafnium dimethyl;
9-silafluorendiyl(2-tert-butyl, 4-[3',5'-di-tbutylphenyl]indenyl)₂hafnium dimethyl;
dimethylsiladiyl(2-methyl, 4-[3',5'-bis-trifluoromethylphenyl]indenyl)₂zirconium dichloride;
dimethylsiladiyl(2-ethyl, 4-[3',5'-bis-trifluoromethylphenyl]indenyl)₂zirconium dichloride;
dimethylsiladiyl(2-n-propyl, 4-[3',5'-bis-trifluoromethylphenyl]indenyl)₂zirconium dichloride;
dimethylsiladiyl(2-iso-propyl, 4-[3',5'-bis-trifluoromethylphenyl]indenyl)₂zirconium dichloride;
dimethylsiladiyl(2-n-butyl, 4-[3',5'-bis-trifluoromethylphenyl]indenyl)₂zirconium dichloride;
dimethylsiladiyl(2-iso-butyl, 4-[3',5'-bis-trifluoromethylphenyl]indenyl)₂zirconium dichloride;
dimethylsiladiyl(2-sec-butyl, 4-[3',5'-bis-trifluoromethylphenyl]indenyl)₂zirconium dichloride;
dimethylsiladiyl(2-tert-butyl, 4-[3',5'-bis-trifluoromethylphenyl]indenyl)₂zirconium dichloride;
dimethylsiladiyl(2-methyl, 4-[3',5'-bis-trifluoromethylphenyl]indenyl)₂hafnium dichloride;
dimethylsiladiyl(2-ethyl, 4-[3',5'-bis-trifluoromethylphenyl]indenyl)₂hafnium dichloride;
dimethylsiladiyl(2-n-propyl, 4-[3',5'-bis-trifluoromethylphenyl]indenyl)₂hafnium dichloride;
dimethylsiladiyl(2-iso-propyl, 4-[3',5'-bis-trifluoromethylphenyl]indenyl)₂hafnium dichloride;
dimethylsiladiyl(2-n-butyl, 4-[3',5'-bis-trifluoromethylphenyl]indenyl)₂hafnium dichloride;
dimethylsiladiyl(2-iso-butyl, 4-[3',5'-bis-trifluoromethylphenyl]indenyl)₂hafnium dichloride;
dimethylsiladiyl(2-sec-butyl, 4-[3',5'-bis-trifluoromethylphenyl]indenyl)₂hafnium dichloride;
dimethylsiladiyl(2-tert-butyl, 4-[3',5'-bis-trifluoromethylphenyl]indenyl)₂hafnium dichloride;
9-silafluorendiyl(2-methyl, 4-[3',5'-bis-trifluoromethylphenyl]indenyl)₂zirconium dichloride;
dimethylsiladiyl(2-ethyl, 4-[3',5'-bis-trifluoromethylphenyl]indenyl)₂hafnium dichloride;
9-silafluorendiyl(2-n-propyl, 4-[3',5'-bis-trifluoromethylphenyl]indenyl)₂zirconium dichloride;
9-silafluorendiyl(2-iso-propyl, 4-[3',5'-bis-trifluoromethylphenyl]indenyl)₂zirconium dichloride;
9-silafluorendiyl(2-n-butyl, 4-[3',5'-bis-trifluoromethylphenyl]indenyl)₂zirconium dichloride;
9-silafluorendiyl(2-iso-butyl, 4-[3',5'-bis-trifluoromethylphenyl]indenyl)₂zirconium dichloride;
9-silafluorendiyl(2-sec-butyl, 4-[3',5'-bis-trifluoromethylphenyl]indenyl)₂zirconium dichloride;
9-silafluorendiyl(2-tert-butyl, 4-[3',5'-bis-trifluoromethylphenyl]indenyl)₂zirconium dichloride;
9-silafluorendiyl(2-methyl, 4-[3',5'-bis-trifluoromethylphenyl]indenyl)₂hafnium dichloride;
9-silafluorendiyl(2-ethyl, 4-[3',5'-bis-trifluoromethylphenyl]indenyl)₂hafnium dichloride;
9-silafluorendiyl(2-n-propyl, 4-[3',5'-bis-trifluoromethylphenyl]indenyl)₂ hafnium dichloride;
9-silafluorendiyl(2-iso-propyl, 4-[3',5'-bis-trifluoromethylphenyl]indenyl)₂ hafnium dichloride;
9-silafluorendiyl(2-n-butyl, 4-[3',5'-bis-trifluoromethylphenyl]indenyl)₂hafnium dichloride;
9-silafluorendiyl(2-iso-butyl, 4-[3',5'-bis-trifluoromethylphenyl]indenyl)₂hafnium dichloride;
9-silafluorendiyl(2-sec-butyl, 4-[3',5'-bis-trifluoromethylphenyl]indenyl)₂hafnium dichloride;
9-silafluorendiyl(2-tert-butyl, 4-[3',5'-bis-trifluoromethylphenyl]indenyl)₂hafnium dichloride;
dimethylsiladiyl(2-methyl, 4-[3',5'-bis-trifluoromethylphenyl]indenyl)₂zirconium dimethyl;
dimethylsiladiyl(2-ethyl, 4-[3',5'-bis-trifluoromethylphenyl]indenyl)₂zirconium dimethyl;
dimethylsiladiyl(2-n-propyl, 4-[3',5'-bis-trifluoromethylphenyl]indenyl)₂zirconium dimethyl;
dimethylsiladiyl(2-iso-propyl, 4-[3',5'-bis-trifluoromethylphenyl]indenyl)₂zirconium dimethyl;
dimethylsiladiyl(2-n-butyl, 4-[3',5'-bis-trifluoromethylphenyl]indenyl)₂zirconium dimethyl;
dimethylsiladiyl(2-iso-butyl, 4-[3',5'-bis-trifluoromethylphenyl]indenyl)₂zirconium dimethyl;
dimethylsiladiyl(2-sec-butyl, 4-[3',5'-bis-trifluoromethylphenyl]indenyl)₂zirconium dimethyl;
dimethylsiladiyl(2-tert-butyl, 4-[3',5'-bis-trifluoromethylphenyl]indenyl)₂zirconium dimethyl;
dimethylsiladiyl(2-methyl, 4-[3',5'-bis-trifluoromethylphenyl]indenyl)₂hafnium dimethyl;
dimethylsiladiyl(2-ethyl, 4-[3',5'-bis-trifluoromethylphenyl]indenyl)₂hafnium dimethyl;
dimethylsiladiyl(2-n-propyl, 4-[3',5'-bis-trifluoromethylphenyl]indenyl)₂hafnium dimethyl;
dimethylsiladiyl(2-iso-propyl, 4-[3',5'-bis-trifluoromethylphenyl]indenyl)₂hafnium dimethyl;
dimethylsiladiyl(2-n-butyl, 4-[3',5'-bis-trifluoromethylphenyl]indenyl)₂hafnium dimethyl;
dimethylsiladiyl(2-iso-butyl, 4-[3',5'-bis-trifluoromethylphenyl]indenyl)₂hafnium dimethyl;
dimethylsiladiyl(2-sec-butyl, 4-[3',5'-bis-trifluoromethylphenyl]indenyl)₂hafnium dimethyl;
dimethylsiladiyl(2-tert-butyl, 4-[3',5'-bis-trifluoromethylphenyl]indenyl)₂hafnium dimethyl;
9-silafluorendiyl(2-methyl, 4-[3',5'-bis-trifluoromethylphenyl]indenyl)₂zirconium dimethyl;
dimethylsiladiyl(2-ethyl, 4-[3',5'-bis-trifluoromethylphenyl]indenyl)₂hafnium dimethyl;
9-silafluorendiyl(2-n-propyl, 4-[3',5'-bis-trifluoromethylphenyl]indenyl)₂zirconium dimethyl;
9-silafluorendiyl(2-iso-propyl, 4-[3',5'-bis-trifluoromethylphenyl]indenyl)₂zirconium dimethyl;
9-silafluorendiyl(2-n-butyl, 4-[3',5'-bis-trifluoromethylphenyl]indenyl)₂zirconium dimethyl;
9-silafluorendiyl(2-iso-butyl, 4-[3',5'-bis-trifluoromethylphenyl]indenyl)₂zirconium dimethyl;
9-silafluorendiyl(2-sec-butyl, 4-[3',5'-bis-trifluoromethylphenyl]indenyl)₂zirconium dimethyl;
9-silafluorendiyl(2-tert-butyl, 4-[3',5'-bis-trifluoromethylphenyl]indenyl)₂zirconium dimethyl;
9-silafluorendiyl(2-methyl, 4-[3',5'-bis-trifluoromethylphenyl]indenyl)₂hafnium dimethyl;
9-silafluorendiyl(2-ethyl, 4-[3',5'-bis-trifluoromethylphenyl]indenyl)₂hafnium dimethyl;
9-silafluorendiyl(2-n-propyl, 4-[3',5'-bis-trifluoromethylphenyl]indenyl)₂ hafnium dimethyl;

9-silafluorendiyl(2-iso-propyl, 4-[3',5'-bis-trifluoromethylphenyl]indenyl)$_2$ hafnium dimethyl;
9-silafluorendiyl(2-n-butyl, 4-[3',5'-bis-trifluoromethylphenyl]indenyl)$_2$hafnium dimethyl;
9-silafluorendiyl(2-iso-butyl, 4-[3',5'-bis-trifluoromethylphenyl]indenyl)$_2$hafnium dimethyl;
9-silafluorendiyl(2-sec-butyl, 4-[3',5'-bis-trifluoromethylphenyl]indenyl)$_2$hafnium dimethyl;
9-silafluorendiyl(2-tert-butyl, 4-[3',5'-bis-trifluoromethylphenyl]indenyl)$_2$hafnium dimethyl;
dimethylsiladiyl(2-ethyl, 4-[3',5'-di-iso-propylphenyl]indenyl)$_2$zirconium dichloride;
dimethylsiladiyl(2-n-propyl, 4-[3',5'-di-iso-propylphenyl]indenyl)$_2$zirconium dichloride dimethylsiladiyl(2-iso-propyl, 4-[3',5'-di-iso-propylphenyl]indenyl)$_2$zirconium dichloride;
dimethylsiladiyl(2-n-butyl, 4-[3',5'-di-iso-propylphenyl]indenyl)$_2$zirconium dichloride;
dimethylsiladiyl(2-iso-butyl, 4-[3',5'-di-iso-propylphenyl]indenyl)$_2$zirconium dichloride;
dimethylsiladiyl(2-sec-butyl, 4-[3',5'-di-iso-propylphenyl]indenyl)$_2$zirconium dichloride;
dimethylsiladiyl(2-tert-butyl, 4-[3',5'-di-iso-propylphenyl]indenyl)$_2$zirconium dichloride;
dimethylsiladiyl(2-ethyl, 4-[3',5'-di-iso-propylphenyl]indenyl)$_2$hafnium dichloride;
dimethylsiladiyl(2-n-propyl, 4-[3',5'-di-iso-propylphenyl]indenyl)$_2$hafnium dichloride;
dimethylsiladiyl(2-iso-propyl, 4-[3',5'-di-iso-propylphenyl]indenyl)$_2$hafnium dichloride;
dimethylsiladiyl(2-n-butyl, 4-[3',5'-di-iso-propylphenyl]indenyl)$_2$hafnium dichloride;
dimethylsiladiyl(2-iso-butyl, 4-[3',5'-di-iso-propylphenyl]indenyl)$_2$hafnium dichloride;
dimethylsiladiyl(2-sec-butyl, 4-[3',5'-di-iso-propylphenyl]indenyl)$_2$hafnium dichloride;
dimethylsiladiyl(2-tert-butyl, 4-[3',5'-di-iso-propylphenyl]indenyl)$_2$hafnium dichloride;
9-silafluorendiyl(2-ethyl, 4-[3',5'-di-iso-propylphenyl]indenyl)$_2$zirconium dichloride;
9-silafluorendiyl(2-n-propyl, 4-[3',5'-di-iso-propylphenyl]indenyl)$_2$zirconium dichloride;
9-silafluorendiyl(2-iso-propyl, 4-[3',5'-di-iso-propylphenyl]indenyl)$_2$zirconium dichloride;
9-silafluorendiyl(2-n-butyl, 4-[3',5'-di-iso-propylphenyl]indenyl)$_2$zirconium dichloride;
9-silafluorendiyl(2-iso-butyl, 4-[3',5'-di-iso-propylphenyl]indenyl)$_2$zirconium dichloride;
9-silafluorendiyl(2-sec-butyl, 4-[3',5'-di-iso-propylphenyl]indenyl)$_2$zirconium dichloride;
9-silafluorendiyl(2-tert-butyl, 4-[3',5'-di-iso-propylphenyl]indenyl)$_2$zirconium dichloride;
9-silafluorendiyl(2-ethyl, 4-[3',5'-di-iso-propylphenyl]indenyl)$_2$hafnium dichloride;
9-silafluorendiyl(2-n-propyl, 4-[3',5'-di-iso-propylphenyl]indenyl)$_2$hafnium dichloride;
9-silafluorendiyl(2-iso-propyl, 4-[3',5'-di-iso-propylphenyl]indenyl)$_2$hafnium dichloride;
9-silafluorendiyl(2-n-butyl, 4-[3',5'-di-iso-propylphenyl]indenyl)$_2$hafnium dichloride;
9-silafluorendiyl(2-iso-butyl, 4-[3',5'-di-iso-propylphenyl]indenyl)$_2$hafnium dichloride;
9-silafluorendiyl(2-sec-butyl, 4-[3',5'-di-iso-propylphenyl]indenyl)$_2$hafnium dichloride;
9-silafluorendiyl(2-tert-butyl, 4-[3',5'-di-iso-propylphenyl]indenyl)$_2$hafnium dichloride;
dimethylsiladiyl(2-ethyl, 4-[3',5'-di-iso-propylphenyl]indenyl)$_2$zirconium dimethyl;
dimethylsiladiyl(2-n-propyl, 4-[3',5'-di-iso-propylphenyl]indenyl)$_2$zirconium dimethyl dimethylsiladiyl(2-iso-propyl, 4-[3',5'-di-iso-propylphenyl]indenyl)$_2$zirconium dimethyl;
dimethylsiladiyl(2-n-butyl, 4-[3',5'-di-iso-propylphenyl]indenyl)$_2$zirconium dimethyl;
dimethylsiladiyl(2-isobutyl, 4-[3',5'-di-iso-propylphenyl]indenyl)$_2$zirconium dimethyl;
dimethylsiladiyl(2-sec-butyl, 4-[3',5'-di-iso-propylphenyl]indenyl)$_2$zirconium dimethyl;
dimethylsiladiyl(2-tert-butyl, 4-[3',5'-di-iso-propylphenyl]indenyl)$_2$zirconium dimethyl;
dimethylsiladiyl(2-ethyl, 4-[3',5'-di-iso-propylphenyl]indenyl)$_2$hafnium dimethyl;
dimethylsiladiyl(2-n-propyl, 4-[3',5'-di-iso-propylphenyl]indenyl)$_2$hafnium dimethyl;
dimethylsiladiyl(2-iso-propyl, 4-[3',5'-di-iso-propylphenyl]indenyl)$_2$hafnium dimethyl;
dimethylsiladiyl(2-n-butyl, 4-[3',5'-di-iso-propylphenyl]indenyl)$_2$hafnium dimethyl;
dimethylsiladiyl(2-iso-butyl, 4-[3',5'-di-iso-propylphenyl]indenyl)$_2$zirconium dimethyl;
dimethylsiladiyl(2-sec-butyl, 4-[3',5'-di-iso-propylphenyl]indenyl)$_2$zirconium dimethyl;
dimethylsiladiyl(2-tert-butyl, 4-[3',5'-di-iso-propylphenyl]indenyl)$_2$zirconium dimethyl;
9-silafluorendiyl(2-ethyl, 4-[3',5'-di-iso-propylphenyl]indenyl)$_2$zirconium dimethyl;
9-silafluorendiyl(2-n-propyl, 4-[3',5'-di-iso-propylphenyl]indenyl)$_2$zirconium dimethyl;
9-silafluorendiyl(2-iso-propyl, 4-[3',5'-di-iso-propylphenyl]indenyl)$_2$zirconium dimethyl;
9-silafluorendiyl(2-n-butyl, 4-[3',5'-di-iso-propylphenyl]indenyl)$_2$zirconium dimethyl;
9-silafluorendiyl(2-iso-butyl, 4-[3',5'-di-iso-propylphenyl]indenyl)$_2$zirconium dimethyl;
9-silafluorendiyl(2-sec-butyl, 4-[3',5'-di-iso-propylphenyl]indenyl)$_2$zirconium dimethyl;
9-silafluorendiyl(2-tert-butyl, 4-[3',5'-di-iso-propylphenyl]indenyl)$_2$zirconium dimethyl;
9-silafluorendiyl(2-ethyl, 4-[3',5'-di-iso-propylphenyl]indenyl)$_2$hafnium dimethyl;
9-silafluorendiyl(2-n-propyl, 4-[3',5'-di-iso-propylphenyl]indenyl)$_2$hafnium dimethyl;
9-silafluorendiyl(2-iso-propyl, 4-[3',5'-di-iso-propylphenyl]indenyl)$_2$hafnium dimethyl;
9-silafluorendiyl(2-n-butyl, 4-[3',5'-di-iso-propylphenyl]indenyl)$_2$hafnium dimethyl;
9-silafluorendiyl(2-iso-butyl, 4-[3',5'-di-iso-propylphenyl]indenyl)$_2$hafnium dimethyl;
9-silafluorendiyl(2-sec-butyl, 4-[3',5'-di-iso-propylphenyl]indenyl)$_2$hafnium dimethyl;
9-silafluorendiyl(2-tert-butyl, 4-[3',5'-di-iso-propylphenyl]indenyl)$_2$hafnium dimethyl;
dimethylsiladiyl(2-methyl, 4-[3',5'-di-phenylphenyl]indenyl)$_2$zirconium dichloride;
dimethylsiladiyl(2-ethyl, 4-[3',5'-di-phenylphenyl]indenyl)$_2$zirconium dichloride;
dimethylsiladiyl(2-n-propyl, 4-[3',5'-di-phenylphenyl]indenyl)$_2$zirconium dichloride;
dimethylsiladiyl(2-iso-propyl, 4-[3',5'-di-phenylphenyl]indenyl)$_2$zirconium dichloride;
dimethylsiladiyl(2-n-butyl, 4-[3',5'-di-phenylphenyl]indenyl)$_2$zirconium dichloride;

dimethylsiladiyl(2-iso-butyl, 4-[3',5'-di-phenylphenyl]indenyl)₂zirconium dichloride;
dimethylsiladiyl(2-sec-butyl, 4-[3',5'-di-phenylphenyl]indenyl)₂zirconium dichloride;
dimethylsiladiyl(2-tert-butyl, 4-[3',5'-di-phenylphenyl]indenyl)₂zirconium dichloride;
dimethylsiladiyl(2-methyl, 4-[3',5'-di-phenylphenyl]indenyl)₂hafnium dichloride;
dimethylsiladiyl(2-ethyl, 4-[3',5'-di-phenylphenyl]indenyl)₂hafnium dichloride;
dimethylsiladiyl(2-n-propyl, 4-[3',5'-di-phenylphenyl]indenyl)₂hafnium dichloride;
dimethylsiladiyl(2-iso-propyl, 4-[3',5'-di-phenylphenyl]indenyl)₂hafnium dichloride;
dimethylsiladiyl(2-n-butyl, 4-[3',5'-di-phenylphenyl]indenyl)₂hafnium dichloride;
dimethylsiladiyl(2-iso-butyl, 4-[3',5'-di-phenylphenyl]indenyl)₂hafnium dichloride;
dimethylsiladiyl(2-sec-butyl, 4-[3',5'-di-phenylphenyl]indenyl)₂hafnium dichloride;
dimethylsiladiyl(2-tert-butyl, 4-[3',5'-di-phenylphenyl]indenyl)₂hafnium dichloride;
9-silafluorendiyl(2-methyl, 4-[3',5'-di-phenylphenyl]indenyl)₂zirconium dichloride;
9-silafluorendiyl(2-ethyl, 4-[3',5'-di-phenylphenyl]indenyl)₂zirconium dichloride;
9-silafluorendiyl(2-n-propyl, 4-[3',5'-di-phenylphenyl]indenyl)₂zirconium dichloride;
9-silafluorendiyl(2-iso-propyl, 4-[3',5'-di-phenylphenyl]indenyl)₂zirconium dichloride;
9-silafluorendiyl(2-n-butyl, 4-[3',5'-di-phenylphenyl]indenyl)₂zirconium dichloride;
9-silafluorendiyl(2-iso-butyl, 4-[3',5'-di-phenylphenyl]indenyl)₂zirconium dichloride;
9-silafluorendiyl(2-sec-butyl, 4-[3',5'-di-phenylphenyl]indenyl)₂zirconium dichloride;
9-silafluorendiyl(2-tert-butyl, 4-[3',5'-di-phenylphenyl]indenyl)₂zirconium dichloride;
9-silafluorendiyl(2-methyl, 4-[3',5'-di-phenylphenyl]indenyl)₂hafnium dichloride;
9-silafluorendiyl(2-ethyl, 4-[3',5'-di-phenylphenyl]indenyl)₂hafnium dichloride;
9-silafluorendiyl(2-n-propyl, 4-[3',5'-di-phenylphenyl]indenyl)₂hafnium dichloride;
9-silafluorendiyl(2-iso-propyl, 4-[3',5'-di-phenylphenyl]indenyl)₂hafnium dichloride;
9-silafluorendiyl(2-n-butyl, 4-[3',5'-di-phenylphenyl]indenyl)₂hafnium dichloride;
9-silafluorendiyl(2-iso-butyl, 4-[3',5'-di-phenylphenyl]indenyl)₂hafnium dichloride;
9-silafluorendiyl(2-sec-butyl, 4-[3',5'-di-phenylphenyl]indenyl)₂hafnium dichloride;
9-silafluorendiyl(2-tert-butyl, 4-[3',5'-di-phenylphenyl]indenyl)₂hafnium dichloride;
dimethylsiladiyl(2-methyl, 4-[3',5'-di-phenylphenyl]indenyl)₂zirconium dimethyl;
dimethylsiladiyl(2-ethyl, 4-[3',5'-di-phenylphenyl]indenyl)₂zirconium dimethyl;
dimethylsiladiyl(2-n-propyl, 4-[3',5'-di-phenylphenyl]indenyl)₂zirconium dimethyl;
dimethylsiladiyl(2-iso-propyl, 4-[3',5'-di-phenylphenyl]indenyl)₂zirconium dimethyl;
dimethylsiladiyl(2-n-butyl, 4-[3',5'-di-phenylphenyl]indenyl)₂zirconium dimethyl;
dimethylsiladiyl(2-iso-butyl, 4-[3',5'-di-phenylphenyl]indenyl)₂zirconium dimethyl;
dimethylsiladiyl(2-sec-butyl, 4-[3',5'-di-phenylphenyl]indenyl)₂zirconium dimethyl;
dimethylsiladiyl(2-tert-butyl, 4-[3',5'-di-phenylphenyl]indenyl)₂zirconium dimethyl;
dimethylsiladiyl(2-methyl, 4-[3',5'-di-phenylphenyl]indenyl)₂hafnium dimethyl;
dimethylsiladiyl(2-ethyl, 4-[3',5'-di-phenylphenyl]indenyl)₂hafnium dimethyl;
dimethylsiladiyl(2-n-propyl, 4-[3',5'-di-phenylphenyl]indenyl)₂hafnium dimethyl;
dimethylsiladiyl(2-iso-propyl, 4-[3',5'-di-phenylphenyl]indenyl)₂hafnium dimethyl;
dimethylsiladiyl(2-n-butyl, 4-[3',5'-di-phenylphenyl]indenyl)₂hafnium dimethyl;
dimethylsiladiyl(2-iso-butyl, 4-[3',5'-di-phenylphenyl]indenyl)₂hafnium dimethyl;
dimethylsiladiyl(2-sec-butyl, 4-[3',5'-di-phenylphenyl]indenyl)₂hafnium dimethyl;
dimethylsiladiyl(2-tert-butyl, 4-[3',5'-di-phenylphenyl]indenyl)₂hafnium dimethyl;
9-silafluorendiyl(2-methyl, 4-[3',5'-di-phenylphenyl]indenyl)₂zirconium dimethyl;
9-silafluorendiyl(2-ethyl, 4-[3',5'-di-phenylphenyl]indenyl)₂zirconium dimethyl;
9-silafluorendiyl(2-n-propyl, 4-[3',5'-di-phenylphenyl]indenyl)₂zirconium dimethyl;
9-silafluorendiyl(2-iso-propyl, 4-[3',5'-di-phenylphenyl]indenyl)₂zirconium dimethyl;
9-silafluorendiyl(2-n-butyl, 4-[3',5'-di-phenylphenyl]indenyl)₂zirconium dimethyl;
9-silafluorendiyl(2-iso-butyl, 4-[3',5'-di-phenylphenyl]indenyl)₂zirconium dimethyl;
9-silafluorendiyl(2-sec-butyl, 4-[3',5'-di-phenylphenyl]indenyl)₂zirconium dimethyl;
9-silafluorendiyl(2-tert-butyl, 4-[3',5'-di-phenylphenyl]indenyl)₂zirconium dimethyl;
9-silafluorendiyl(2-methyl, 4-[3',5'-di-phenylphenyl]indenyl)₂hafnium dimethyl;
9-silafluorendiyl(2-ethyl, 4-[3',5'-di-phenylphenyl]indenyl)₂hafnium dichloride;
9-silafluorendiyl(2-n-propyl, 4-[3',5'-di-phenylphenyl]indenyl)₂hafnium dimethyl;
9-silafluorendiyl(2-iso-propyl, 4-[3',5'-di-phenylphenyl]indenyl)₂hafnium dimethyl;
9-silafluorendiyl(2-n-butyl, 4-[3',5'-di-phenylphenyl]indenyl)₂hafnium dimethyl;
9-silafluorendiyl(2-iso-butyl, 4-[3',5'-di-phenylphenyl]indenyl)₂hafnium dimethyl;
9-silafluorendiyl(2-sec-butyl, 4-[3',5'-di-phenylphenyl]indenyl)₂hafnium dimethyl;
9-silafluorendiyl(2-tert-butyl, 4-[3',5'-di-phenylphenyl]indenyl)₂hafnium dimethyl;
dimethylamidoborane(2-methyl, 4-[3',5'-di-tbutylphenyl]indenyl)₂zirconium dichloride;
dimethylamidoborane(2-ethyl, 4-[3',5'-di-tbutylphenyl]indenyl)₂zirconium dichloride;
dimethylamidoborane(2-n-propyl, 4-[3',5'-di-tbutylphenyl]indenyl)₂zirconium dichloride;
dimethylamidoborane(2-iso-propyl, 4-[3',5'-di-tbutylphenyl]indenyl)₂zirconium dichloride;
dimethylamidoborane(2-n-butyl, 4-[3',5'-di-tbutylphenyl]indenyl)₂zirconium dichloride;
dimethylamidoborane(2-iso-butyl, 4-[3',5'-di-tbutylphenyl]indenyl)₂zirconium dichloride;
dimethylamidoborane(2-sec-butyl, 4-[3',5'-di-tbutylphenyl]indenyl)₂zirconium dichloride;

dimethylamidoborane(2-tert-butyl, 4-[3',5'-di-tbutylphenyl]indenyl)₂zirconium dichloride;
dimethylamidoborane(2-ethyl, 4-[3',5'-bis-trifluoromethylphenyl]indenyl)₂zirconium dichloride;
dimethylamidoborane(2-n-propyl, 4-[3',5'-bis-trifluoromethylphenyl]indenyl)₂zirconium dichloride;
dimethylamidoborane(2-iso-propyl, 4-[3',5'-bis-trifluoromethylphenyl]indenyl)₂zirconium dichloride;
dimethylamidoborane(2-n-butyl, 4-[3',5'-bis-trifluoromethylphenyl]indenyl)₂zirconium dichloride;
dimethylamidoborane(2-iso-butyl, 4-[3',5'-bis-trifluoromethylphenyl]indenyl)₂zirconium dichloride;
dimethylamidoborane(2-sec-butyl, 4-[3',5'-bis-trifluoromethylphenyl]indenyl)₂zirconium dichloride;
dimethylamidoborane(2-tert-butyl, 4-[3',5'-bis-trifluoromethylphenyl]indenyl)₂zirconium dichloride;
dimethylamidoborane(2-ethyl, 4-[3',5'-di-iso-propylphenyl]indenyl)₂zirconium dichloride;
dimethylamidoborane(2-n-propyl, 4-[3',5'-di-iso-propylphenyl]indenyl)₂zirconium dichloride
dimethylamidoborane(2-iso-propyl, 4-[3',5'-di-iso-propylphenyl]indenyl)₂zirconium dichloride;
dimethylamidoborane(2-n-butyl, 4-[3',5'-di-iso-propylphenyl]indenyl)₂zirconium dichloride;
dimethylamidoborane(2-iso-butyl, 4-[3',5'-di-iso-propylphenyl]indenyl)₂zirconium dichloride;
dimethylamidoborane(2-sec-butyl, 4-[3',5'-di-iso-propylphenyl]indenyl)₂zirconium dichloride;
dimethylamidoborane(2-tert-butyl, 4-[3',5'-di-iso-propylphenyl]indenyl)₂zirconium dichloride;
dimethylamidoborane(2-methyl, 4-[3',5'-di-phenylphenyl]indenyl)₂zirconium dichloride;
dimethylamidoborane(2-ethyl, 4-[3',5'-di-phenylphenyl]indenyl)₂zirconium dichloride;
dimethylamidoborane(2-n-propyl, 4-[3',5'-di-phenylphenyl]indenyl)₂zirconium dichloride;
dimethylamidoborane(2-iso-propyl, 4-[3',5'-di-phenylphenyl]indenyl)₂zirconium dichloride;
dimethylamidoborane(2-n-butyl, 4-[3',5'-di-phenylphenyl]indenyl)₂zirconium dichloride;
dimethylamidoborane(2-iso-butyl, 4-[3',5'-di-phenylphenyl]indenyl)₂zirconium dichloride;
dimethylamidoborane(2-sec-butyl, 4-[3',5'-di-phenylphenyl]indenyl)₂zirconium dichloride;
dimethylamidoborane(2-tert-butyl, 4-[3',5'-di-phenylphenyl]indenyl)₂zirconium dichloride;
dimethylamidoborane(2-methyl, 4-[3',5'-di-tbutylphenyl]indenyl)₂ zirconium dimethyl;
dimethylamidoborane(2-ethyl, 4-[3',5'-di-tbutylphenyl]indenyl)₂zirconium dimethyl;
dimethylamidoborane(2-n-propyl, 4-[3',5'-di-tbutylphenyl]indenyl)₂zirconium dimethyl;
dimethylamidoborane(2-iso-propyl, 4-[3',5'-di-tbutylphenyl]indenyl)₂zirconium dimethyl;
dimethylamidoborane(2-n-butyl, 4-[3',5'-di-tbutylphenyl]indenyl)₂zirconium dimethyl;
dimethylamidoborane(2-iso-butyl, 4-[3',5'-di-tbutylphenyl]indenyl)₂zirconium dimethyl;
dimethylamidoborane(2-sec-butyl, 4-[3',5'-di-tbutylphenyl]indenyl)₂zirconium dimethyl;
dimethylamidoborane(2-tert-butyl, 4-[3',5'-di-tbutylphenyl]indenyl)₂zirconium dimethyl;
dimethylamidoborane(2-ethyl, 4-[3',5'-bis-trifluoromethylphenyl]indenyl)₂zirconium dimethyl;
dimethylamidoborane(2-n-propyl, 4-[3',5'-bis-trifluoromethylphenyl]indenyl)₂zirconium dimethyl;
dimethylamidoborane(2-iso-propyl, 4-[3',5'-bis-trifluoromethylphenyl]indenyl)₂zirconium dimethyl;
dimethylamidoborane(2-n-butyl, 4-[3',5'-bis-trifluoromethylphenyl]indenyl)₂zirconium dimethyl;
dimethylamidoborane(2-iso-butyl, 4-[3',5'-bis-trifluoromethylphenyl]indenyl)₂zirconium dimethyl;
dimethylamidoborane(2-sec-butyl, 4-[3',5'-bis-trifluoromethylphenyl]indenyl)₂zirconium dimethyl;
dimethylamidoborane(2-tert-butyl, 4-[3',5'-bis-trifluoromethylphenyl]indenyl)₂zirconium dimethyl;
dimethylamidoborane(2-ethyl, 4-[3',5'-di-iso-propylphenyl]indenyl)₂zirconium dimethyl;
dimethylamidoborane(2-n-propyl, 4-[3',5'-di-iso-propylphenyl]indenyl)₂zirconium dimethyl dimethylamidoborane (2-iso-propyl, 4-[3',5'-di-iso-propylphenyl]indenyl)₂zirconium dimethyl;
dimethylamidoborane(2-n-butyl, 4-[3',5'-di-iso-propylphenyl]indenyl)₂zirconium dimethyl;
dimethylamidoborane(2-iso-butyl, 4-[3',5'-di-iso-propylphenyl]indenyl)₂zirconium dimethyl;
dimethylamidoborane(2-sec-butyl, 4-[3',5'-di-iso-propylphenyl]indenyl)₂zirconium dimethyl;
dimethylamidoborane(2-tert-butyl, 4-[3',5'-di-iso-propylphenyl]indenyl)₂zirconium dimethyl;
dimethylamidoborane(2-methyl, 4-[3',5'-di-phenylphenyl]indenyl)₂zirconium dimethyl;
dimethylamidoborane(2-ethyl, 4-[3',5'-di-phenylphenyl]indenyl)₂zirconium dimethyl;
dimethylamidoborane(2-n-propyl, 4-[3',5'-di-phenylphenyl]indenyl)₂zirconium dimethyl;
dimethylamidoborane(2-iso-propyl, 4-[3',5'-di-phenylphenyl]indenyl)₂zirconium dimethyl;
dimethylamidoborane(2-n-butyl, 4-[3',5'-di-phenylphenyl]indenyl)₂zirconium dimethyl;
dimethylamidoborane(2-iso-butyl, 4-[3',5'-di-phenylphenyl]indenyl)₂zirconium dimethyl;
dimethylamidoborane(2-sec-butyl, 4-[3',5'-di-phenylphenyl]indenyl)₂zirconium dimethyl;
dimethylamidoborane(2-tert-butyl, 4-[3',5'-di-phenylphenyl]indenyl)₂zirconium dimethyl;
diisopropylamidoborane(2-methyl, 4-[3',5'-di-tbutylphenyl]indenyl)₂zirconium dichloride;
diisopropylamidoborane(2-ethyl, 4-[3',5'-di-tbutylphenyl]indenyl)₂zirconium dichloride;
diisopropylamidoborane(2-n-propyl, 4-[3',5'-di-tbutylphenyl]indenyl)₂zirconium dichloride;
diisopropylamidoborane(2-iso-propyl, 4-[3',5'-di-tbutylphenyl]indenyl)₂zirconium dichloride;
diisopropylamidoborane(2-n-butyl, 4-[3',5'-di-tbutylphenyl]indenyl)₂zirconium dichloride;
diisopropylamidoborane(2-iso-butyl, 4-[3',5'-di-tbutylphenyl]indenyl)₂zirconium dichloride;
diisopropylamidoborane(2-sec-butyl, 4-[31,5'-di-tbutylphenyl]indenyl)₂zirconium dichloride;
diisopropylamidoborane(2-tert-butyl, 4-[3',5'-di-tbutylphenyl]indenyl)₂zirconium dichloride;
diisopropylamidoborane(2-ethyl, 4-[3',5'-bis-trifluoromethylphenyl]indenyl)₂zirconium dichloride;
diisopropylamidoborane(2-n-propyl, 4-[3',5'-bis-trifluoromethylphenyl]indenyl)₂zirconium dichloride;
diisopropylamidoborane(2-iso-propyl, 4-[3',5'-bis-trifluoromethylphenyl]indenyl)₂zirconium dichloride;
diisopropylamidoborane(2-n-butyl, 4-[3',5'-bis-trifluoromethylphenyl]indenyl)₂zirconium dichloride;
diisopropylamidoborane(2-iso-butyl, 4-[3',5'-bis-trifluoromethylphenyl]indenyl)₂zirconium dichloride;

diisopropylamidoborane(2-sec-butyl, 4-[3',5'-bis-trifluoromethylphenyl]indenyl)$_2$zirconium dichloride;
diisopropylamidoborane(2-tert-butyl, 4-[3',5'-bis-trifluoromethylphenyl]indenyl)$_2$zirconium dichloride;
diisopropylamidoborane(2-ethyl, 4-[3',5'-di-iso-propylphenyl]indenyl)$_2$zirconium dichloride;
diisopropylamidoborane(2-n-propyl, 4-[3',5'-di-iso-propylphenyl]indenyl)$_2$zirconium dichloride
diisopropylamidoborane(2-iso-propyl, 4-[3',5'-di-iso-propylphenyl]indenyl)$_2$zirconium dichloride;
diisopropylamidoborane(2-n-butyl, 4-[3',5'-di-iso-propylphenyl]indenyl)$_2$zirconium dichloride;
diisopropylamidoborane(2-iso-butyl, 4-[3',5'-di-iso-propylphenyl]indenyl)$_2$zirconium dichloride;
diisopropylamidoborane(2-sec-butyl, 4-[3',5'-di-iso-propylphenyl]indenyl)$_2$zirconium dichloride;
diisopropylamidoborane(2-tert-butyl, 4-[3',5'-di-iso-propylphenyl]indenyl)$_2$zirconium dichloride;
diisopropylamidoborane(2-methyl, 4-[3',5'-di-phenylphenyl]indenyl)$_2$zirconium dichloride;
diisopropylamidoborane(2-ethyl, 4-[3',5'-di-phenylphenyl]indenyl)$_2$zirconium dichloride;
diisopropylamidoborane(2-n-propyl, 4-[3',5'-di-phenylphenyl]indenyl)$_2$zirconium dichloride;
diisopropylamidoborane(2-iso-propyl, 4-[3',5'-di-phenylphenyl]indenyl)$_2$zirconium dichloride;
diisopropylamidoborane(2-n-butyl, 4-[3',5'-di-phenylphenyl]indenyl)$_2$zirconium dichloride;
diisopropylamidoborane(2-iso-butyl, 4-[3',5'-di-phenylphenyl]indenyl)$_2$zirconium dichloride;
diisopropylamidoborane(2-sec-butyl, 4-[3',5'-di-phenylphenyl]indenyl)$_2$zirconium dichloride;
diisopropylamidoborane(2-tert-butyl, 4-[3',5'-di-phenylphenyl]indenyl)$_2$zirconium dichloride;
diisopropylamidoborane(2-methyl, 4-[3',5'-di-tbutylphenyl]indenyl)$_2$zirconium dimethyl;
diisopropylamidoborane(2-ethyl, 4-[3',5'-di-tbutylphenyl]indenyl)$_2$zirconium dimethyl;
diisopropylamidoborane(2-n-propyl, 4-[3',5'-di-tbutylphenyl]indenyl)$_2$zirconium dimethyl;
diisopropylamidoborane(2-iso-propyl, 4-[3',5'-di-tbutylphenyl]indenyl)$_2$zirconium dimethyl;
diisopropylamidoborane(2-n-butyl, 4-[3',5'-di-tbutylphenyl]indenyl)$_2$zirconium dimethyl;
diisopropylamidoborane(2-iso-butyl, 4-[3',5'-di-tbutylphenyl]indenyl)$_2$zirconium dimethyl;
diisopropylamidoborane(2-sec-butyl, 4-[3',5'-di-tbutylphenyl]indenyl)$_2$zirconium dimethyl;
diisopropylamidoborane(2-tert-butyl, 4-[3',5'-di-tbutylphenyl]indenyl)$_2$zirconium dimethyl;
diisopropylamidoborane(2-ethyl, 4-[3',5'-bis-trifluoromethylphenyl]indenyl)$_2$zirconium dimethyl;
diisopropylamidoborane(2-n-propyl, 4-[3',5'-bis-trifluoromethylphenyl]indenyl)$_2$zirconium dimethyl;
diisopropylamidoborane(2-iso-propyl, 4-[3',5'-bis-trifluoromethylphenyl]indenyl)$_2$zirconium dimethyl;
diisopropylamidoborane(2-n-butyl, 4-[3',5'-bis-trifluoromethylphenyl]indenyl)$_2$zirconium dimethyl;
diisopropylamidoborane(2-iso-butyl, 4-[3',5'-bis-trifluoromethylphenyl]indenyl)$_2$zirconium dimethyl;
diisopropylamidoborane(2-sec-butyl, 4-[3',5'-bis-trifluoromethylphenyl]indenyl)$_2$zirconium dimethyl;
diisopropylamidoborane(2-tert-butyl, 4-[3',5'-bis-trifluoromethylphenyl]indenyl)$_2$zirconium dimethyl;
diisopropylamidoborane(2-ethyl, 4-[3',5'-di-iso-propylphenyl]indenyl)$_2$zirconium dimethyl;
diisopropylamidoborane(2-n-propyl, 4-[3',5'-di-iso-propylphenyl]indenyl)$_2$zirconium dimethyl
diisopropylamidoborane(2-iso-propyl, 4-[3',5'-di-iso-propylphenyl]indenyl)$_2$zirconium dimethyl;
diisopropylamidoborane(2-n-butyl, 4-[3',5'-di-iso-propylphenyl]indenyl)$_2$zirconium dimethyl;
diisopropylamidoborane(2-iso-butyl, 4-[3',5'-di-iso-propylphenyl]indenyl)$_2$zirconium dimethyl;
diisopropylamidoborane(2-sec-butyl, 4-[3',5'-di-iso-propylphenyl]indenyl)$_2$zirconium dimethyl;
diisopropylamidoborane(2-tert-butyl, 4-[3',5'-di-iso-propylphenyl]indenyl)$_2$zirconium dimethyl;
diisopropylamidoborane(2-methyl, 4-[3',5'-di-phenylphenyl]indenyl)$_2$zirconium dimethyl;
diisopropylamidoborane(2-ethyl, 4-[3',5'-di-phenylphenyl]indenyl)$_2$zirconium dimethyl;
diisopropylamidoborane(2-n-propyl, 4-[3',5'-di-phenylphenyl]indenyl)$_2$zirconium dimethyl;
diisopropylamidoborane(2-iso-propyl, 4-[3',5'-di-phenylphenyl]indenyl)$_2$zirconium dimethyl;
diisopropylamidoborane(2-n-butyl, 4-[3',5'-di-phenylphenyl]indenyl)$_2$zirconium dimethyl;
diisopropylamidoborane(2-iso-butyl, 4-[3',5'-di-phenylphenyl]indenyl)$_2$zirconium dimethyl;
diisopropylamidoborane(2-sec-butyl, 4-[3',5'-di-phenylphenyl]indenyl)$_2$zirconium dimethyl;
diisopropylamidoborane(2-tert-butyl, 4-[3',5'-di-phenylphenyl]indenyl)$_2$zirconium dimethyl;
bis(trimethylsilyl)amidoborane(2-methyl, 4-[3',5'-di-tbutylphenyl]indenyl)$_2$zirconium dichloride;
bis(trimethylsilyl)amidoborane(2-ethyl, 4-[3',5'-di-tbutylphenyl]indenyl)$_2$zirconium dichloride;
bis(trimethylsilyl)amidoborane(2-n-propyl, 4-[3',5'-di-tbutylphenyl]indenyl)$_2$zirconium dichloride;
bis(trimethylsilyl)amidoborane(2-iso-propyl, 4-[3',5'-di-tbutylphenyl]indenyl)$_2$zirconium dichloride;
bis(trimethylsilyl)amidoborane(2-n-butyl, 4-[3',5'-di-tbutylphenyl]indenyl)$_2$zirconium dichloride;
bis(trimethylsilyl)amidoborane(2-iso-butyl, 4-[3',5'-di-tbutylphenyl]indenyl)$_2$zirconium dichloride;
bis(trimethylsilyl)amidoborane(2-sec-butyl, 4-[3',5'-di-tbutylphenyl]indenyl)$_2$zirconium dichloride;
bis(trimethylsilyl)amidoborane(2-tert-butyl, 4-[3',5'-di-tbutylphenyl]indenyl)$_2$zirconium dichloride;
bis(trimethylsilyl)amidoborane(2-ethyl, 4-[3',5'-bis-trifluoromethylphenyl]indenyl)$_2$zirconium dichloride;
bis(trimethylsilyl)amidoborane(2-n-propyl, 4-[3',5'-bis-trifluoromethylphenyl]indenyl)$_2$zirconium dichloride;
bis(trimethylsilyl)amidoborane(2-iso-propyl, 4-[3',5'-bis-trifluoromethylphenyl]indenyl)$_2$zirconium dichloride;
bis(trimethylsilyl)amidoborane(2-n-butyl, 4-[3',5'-bis-trifluoromethylphenyl]indenyl)$_2$zirconium dichloride;
bis(trimethylsilyl)amidoborane(2-iso-butyl, 4-[3',5'-bis-trifluoromethylphenyl]indenyl)$_2$zirconium dichloride;
bis(trimethylsilyl)amidoborane(2-sec-butyl, 4-[3',5'-bis-trifluoromethylphenyl]indenyl)$_2$zirconium dichloride;
bis(trimethylsilyl)amidoborane(2-tert-butyl, 4-[3',5'-bis-trifluoromethylphenyl]indenyl)$_2$zirconium dichloride;
bis(trimethylsilyl)amidoborane(2-ethyl, 4-[3',5'-di-iso-propylphenyl]indenyl)$_2$zirconium dichloride;
bis(trimethylsilyl)amidoborane(2-n-propyl, 4-[3',5'-di-iso-propylphenyl]indenyl)$_2$zirconium dichloride
bis(trimethylsilyl)amidoborane(2-iso-propyl, 4-[3',5'-di-iso-propylphenyl]indenyl)$_2$zirconium dichloride;
bis(trimethylsilyl)amidoborane(2-n-butyl, 4-[3',5'-di-iso-propylphenyl]indenyl)$_2$zirconium dichloride;

bis(trimethylsilyl)amidoborane(2-iso-butyl, 4-[3',5'-di-isopropylphenyl]indenyl)₂zirconium dichloride;
bis(trimethylsilyl)amidoborane(2-sec-butyl, 4-[3',5'-di-isopropylphenyl]indenyl)₂zirconium dichloride;
bis(trimethylsilyl)amidoborane(2-tert-butyl, 4-[3',5'-di-isopropylphenyl]indenyl)₂zirconium dichloride;
bis(trimethylsilyl)amidoborane(2-methyl, 4-[3',5'-di-phenylphenyl]indenyl)₂zirconium dichloride;
bis(trimethylsilyl)amidoborane(2-ethyl, 4-[3',5'-di-phenylphenyl]indenyl)₂zirconium dichloride;
bis(trimethylsilyl)amidoborane(2-n-propyl, 4-[3',5'-di-phenylphenyl]indenyl)₂zirconium dichloride;
bis(trimethylsilyl)amidoborane(2-iso-propyl, 4-[3',5'-diphenylphenyl]indenyl)₂zirconium dichloride;
bis(trimethylsilyl)amidoborane(2-n-butyl, 4-[3',5'-di-phenylphenyl]indenyl)₂zirconium dichloride;
bis(trimethylsilyl)amidoborane(2-iso-butyl, 4-[3',5'-di-phenylphenyl]indenyl)₂zirconium dichloride;
bis(trimethylsilyl)amidoborane(2-sec-butyl, 4-[3',5'-di-phenylphenyl]indenyl)₂zirconium dichloride;
bis(trimethylsilyl)amidoborane(2-tert-butyl, 4-[3',5'-di-phenylphenyl]indenyl)₂zirconium dichloride;
bis(trimethylsilyl)amidoborane(2-methyl, 4-[3',5'-di-tbutylphenyl]indenyl)₂zirconium dimethyl;
bis(trimethylsilyl)amidoborane(2-ethyl, 4-[3',5'-di-tbutylphenyl]indenyl)₂zirconium dimethyl;
bis(trimethylsilyl)amidoborane(2-n-propyl, 4-[3',5'-di-tbutylphenyl]indenyl)₂zirconium dimethyl;
bis(trimethylsilyl)amidoborane(2-iso-propyl, 4-[3',5'-di-tbutylphenyl]indenyl)₂zirconium dimethyl;
bis(trimethylsilyl)amidoborane(2-n-butyl, 4-[3',5'-di-tbutylphenyl]indenyl)₂zirconium dimethyl;
bis(trimethylsilyl)amidoborane(2-iso-butyl, 4-[3',5'-di-tbutylphenyl]indenyl)₂zirconium dimethyl;
bis(trimethylsilyl)amidoborane(2-sec-butyl, 4-[3',5'-di-tbutylphenyl]indenyl)₂zirconium dimethyl;
bis(trimethylsilyl)amidoborane(2-tert-butyl, 4-[3',5'-di-tbutylphenyl]indenyl)₂zirconium dimethyl;
bis(trimethylsilyl)amidoborane(2-ethyl, 4-[3',5'-bis-trifluoromethylphenyl]indenyl)₂zirconium dimethyl;
bis(trimethylsilyl)amidoborane(2-n-propyl, 4-[3',5'-bis-trifluoromethylphenyl]indenyl)₂zirconium dimethyl;
bis(trimethylsilyl)amidoborane(2-iso-propyl, 4-[3',5'-bis-trifluoromethylphenyl]indenyl)₂zirconium dimethyl;
bis(trimethylsilyl)amidoborane(2-n-butyl, 4-[3',5'-bis-trifluoromethylphenyl]indenyl)₂zirconium dimethyl;
bis(trimethylsilyl)amidoborane(2-iso-butyl, 4-[3',5'-bis-trifluoromethylphenyl]indenyl)₂zirconium dimethyl;
bis(trimethylsilyl)amidoborane(2-sec-butyl, 4-[3',5'-bis-trifluoromethylphenyl]indenyl)₂zirconium dimethyl;
bis(trimethylsilyl)amidoborane(2-tert-butyl, 4-[3',5'-bis-trifluoromethylphenyl]indenyl)₂zirconium dimethyl;
bis(trimethylsilyl)amidoborane(2-ethyl, 4-[3',5'-di-iso-propylphenyl]indenyl)₂zirconium dimethyl;
bis(trimethylsilyl)amidoborane(2-n-propyl, 4-[3',5'-di-isopropylphenyl]indenyl)₂zirconium dimethyl
bis(trimethylsilyl)amidoborane(2-iso-propyl, 4-[3',5'-di-isopropylphenyl]indenyl)₂zirconium dimethyl;
bis(trimethylsilyl)amidoborane(2-n-butyl, 4-[3',5'-di-isopropylphenyl]indenyl)₂zirconium dimethyl;
bis(trimethylsilyl)amidoborane(2-iso-butyl, 4-[3',5'-di-isopropylphenyl]indenyl)₂zirconium dimethyl;
bis(trimethylsilyl)amidoborane(2-sec-butyl, 4-[3',5'-di-isopropylphenyl]indenyl)₂zirconium dimethyl;
bis(trimethylsilyl)amidoborane(2-tert-butyl, 4-[3',5'-di-isopropylphenyl]indenyl)₂zirconium dimethyl;
bis(trimethylsilyl)amidoborane(2-methyl, 4-[3',5'-di-phenylphenyl]indenyl)₂zirconium dimethyl;
bis(trimethylsilyl)amidoborane(2-ethyl, 4-[3',5'-di-phenylphenyl]indenyl)₂zirconium dimethyl;
bis(trimethylsilyl)amidoborane(2-n-propyl, 4-[3',5'-di-phenylphenyl]indenyl)₂zirconium dimethyl;
bis(trimethylsilyl)amidoborane(2-iso-propyl, 4-[3',5'-di-phenylphenyl]indenyl)₂zirconium dimethyl;
bis(trimethylsilyl)amidoborane(2-n-butyl, 4-[3',5'-di-phenylphenyl]indenyl)₂zirconium dimethyl;
bis(trimethylsilyl)amidoborane(2-iso-butyl, 4-[3',5'-di-phenylphenyl]indenyl)₂zirconium dimethyl;
bis(trimethylsilyl)amidoborane(2-sec-butyl, 4-[3',5'-di-phenylphenyl]indenyl)₂zirconium dimethyl; and
bis(trimethylsilyl)amidoborane(2-tert-butyl, 4-[3',5'-di-phenylphenyl]indenyl)₂zirconium dimethyl.

Group 15 containing metal compounds which may be utilized as a catalyst include for example, those disclosed in EP 0 893 454 A1, U.S. Pat. No. 5,889,128 and the references cited in U.S. Pat. No. 5,889,128 which are all herein incorporated by reference. U.S. application Ser. No. 09/312,878, filed May 17, 1999, discloses a gas or slurry phase polymerization process using a supported bisamide catalyst, which is also incorporated herein by reference. For additional information of Group 15 containing metal compounds, please see Mitsui Chemicals, Inc. in EP 0 893 454 A1 which discloses transition metal amides combined with activators to polymerize olefins.

It is further contemplated that bis-amide based pre-catalysts may be used. Exemplary compounds include those described in international patent publications WO 96/23010, WO 97/48735 and Gibson, et al., *Chem. Comm.*, pp. 849-850 (1998), which disclose diimine-based ligands for Group-8-10 compounds that undergo ionic activation and polymerize olefins. Polymerization catalyst systems from Group-5-10 metals, in which the active center is highly oxidized and stabilized by low-coordination-number, polyanionic, ligand systems, are described in U.S. Pat. No. 5,502,124 and its divisional U.S. Pat. No. 5,504,049. See also the Group-5 organometallic catalyst compounds of U.S. Pat. No. 5,851,945 and the tridentate-ligand-containing, Group-5-10, organometallic catalysts of U.S. Pat. No. 6,294,495. Group-11 catalyst precursor compounds, activatable with ionizing cocatalysts, useful for olefin and vinylic polar molecules are described in WO 99/30822.

Other useful catalysts and pre-catalysts include Group 5 and 6 metal imido complexes as described, for example, in EP-A2-0 816 384 and U.S. Pat. No. 5,851,945, which is incorporated herein by reference. In addition, metallocene catalysts may include bridged bis(arylamido) Group 4 compounds described by D. H. McConville, et al., in Organometallics 1195, 14, 5478-5480, which is herein incorporated by reference. In addition, bridged bis(amido) catalyst compounds are described in WO 96/27439, which is herein incorporated by reference. Other useful catalysts are described as bis(hydroxy aromatic nitrogen ligands) in U.S. Pat. No. 5,852,146, which is incorporated herein by reference. Also, catalysts containing one or more Group 15 atoms include those described in WO 98/46651, which is herein incorporated by reference.

U.S. Pat. No. 5,318,935 describes bridged and unbridged, bisamido catalyst compounds of Group-4 metals capable of α-olefins polymerization. Bridged bis(arylamido) Group-4 compounds for olefin polymerization are described by D. H. McConville, et al., in *Organometallics* 1995, 14, 5478-5480. This reference presents synthetic methods and compound characterizations. Further work appearing in D. H. McConville, et al, *Macromolecules* 1996, 29, 5241-5243, describes bridged bis(arylamido) Group-4 compounds that are polymerization catalysts for 1-hexene. Additional invention-suitable transition metal compounds include those described in WO 96/40805. Cationic Group-3- or Lanthanide-metal olefin polymerization complexes are disclosed in U.S. application Ser. No. 09/408,050, filed 29 Sep. 1999, which is directed to a monoanionic bidentate ligand and two monoanionic ligands that stabilize catalyst precursors.

Other suitable catalyst-precursor compounds suitable for use herein preferably contain abstractable ligands or can be alkylated to contain abstractable ligands. See, for example, V. C. Gibson, et al; "The Search for New-Generation Olefin Polymerization Catalysts: Life Beyond Metallocenes", *Angew. Chem. Int. Ed.*, 38, 428-447 (1999). The catalyst or pre-catalyst may also include phenoxide ligands such as those disclosed in EP 0 874 005 A1, which in incorporated by reference herein.

In another embodiment, various transition metal catalysts, referred to herein as "conventional-type transition metal catalysts" may be used in the practice of this invention. Conventional-type transition metal catalysts may include Ziegler-Natta catalysts, vanadium catalysts, and Phillips-type catalysts, among others. Examples of Ziegler-Natta catalysts include those described in *Ziegler-Natta Catalysts and Polymerizations*, John Boor, Academic Press, New York, 1979. Examples of conventional-type transition metal catalysts are also discussed in U.S. Pat. Nos. 4,115,639, 4,077,904, 4,482,687, 4,564,605, 4,721,763, 4,879,359 and 4,960,741, all of which are herein fully incorporated by reference. Preferably, conventional-type transition metal catalyst compounds that may be used in the present invention include transition metal compounds from Groups 3 to 17, preferably 4 to 12, more preferably 4 to 6 of the Periodic Table of Elements.

Preferred conventional-type transition metal catalysts may be represented by the formula: $MR_x$, where M is a metal from Groups 3 to 17, preferably Group 4 to 6, more preferably Group 4, most preferably titanium; R is a halogen or a hydrocarbyloxy group; and x is the oxidation state of the metal M. Non-limiting examples of R include alkoxy, phenoxy, bromide, chloride and fluoride. Non-limiting examples of conventional-type transition metal catalysts where M is titanium include $TiCl_4$, $TiBr_4$, $Ti(OC_2H_5)_3Cl$, $Ti(OC_2H_5)Cl_3$, $Ti(OC_4H_9)_3Cl$, $Ti(OC_3H_7)_2Cl_2$, $Ti(OC_2H_5)_2Br_2$, $TiCl_3 \cdot 1/3AlCl_3$ and $Ti(OC_{12}H_{25})Cl_3$.

Conventional-type transition metal catalyst compounds based on magnesium/titanium electron-donor complexes that are useful in the invention are described in, for example, U.S. Pat. Nos. 4,302,565 and 4,302,566, which are herein fully incorporate by reference. The $MgTiCl_6$ (ethyl acetate)$_4$ derivative is particularly preferred.

British Patent Application 2,105,355 and U.S. Pat. No. 5,317,036, herein incorporated by reference, describes various conventional-type vanadium catalyst compounds. Non-limiting examples of conventional-type vanadium catalyst compounds include vanadyl trihalide, alkoxy halides and alkoxides such as $VOCl_3$, $VOCl_2(OBu)$ where Bu=butyl and $VO(OC_2H_5)_3$; vanadium tetra-halide and vanadium alkoxy halides such as $VCl_4$ and $VCl_3(OBu)$; vanadium and vanadyl acetyl acetonates and chloroacetyl acetonates such as $V(AcAc)_3$ and $VOCl_2(AcAc)$ where (AcAc) is an acetyl acetonate. Preferred conventional-type vanadium catalyst compounds include $VOCl_3$, $VCl_4$ and $VOCl_2$—OR where R is a hydrocarbon radical, preferably a $C_1$ to $C_{10}$ aliphatic or aromatic hydrocarbon radical such as ethyl, phenyl, isopropyl, butyl, propyl, n-butyl, iso-butyl, tertiary-butyl, hexyl, cyclohexyl, naphthyl, and the like, and vanadium acetyl acetonates.

Conventional-type chromium catalyst compounds, referred to herein as Phillips-type catalysts, suitable for use in the present invention include $CrO_3$, chromocene, silyl chromate, chromyl chloride ($CrO_2Cl_2$), chromium-2-ethyl-hexanoate, chromium acetylacetonate ($Cr(AcAc)_3$), and the like. Non-limiting examples are disclosed in U.S. Pat. Nos. 3,709,853, 3,709,954, 3,231,550, 3,242,099 and 4,077,904, which are herein fully incorporated by reference.

Still other conventional-type transition metal catalyst compounds and catalyst systems suitable for use in the present invention are disclosed in U.S. Pat. Nos. 4,124,532, 4,302,565, 4,302,566, 4,376,062, 4,379,758, 5,066,737, 5,763,723, 5,849,655, 5,852,144, 5,854,164 and 5,869,585 and published EP-A2 0 416 815 A2 and EP-A1 0 420 436, and in published application WO 03/040201 A1, which are all herein incorporated by reference.

Other catalysts may include cationic catalysts such as $AlCl_3$, and other cobalt, iron, nickel and palladium catalysts; see for example U.S. Pat. Nos. 3,487,112, 4,472,559, 4,182,814 and 4,689,437, all of which are incorporated herein by reference.

It is also contemplated that catalysts can be combined for use in the present invention. For example, see U.S. Pat. Nos. 4,937,299, 4,935,474, 5,281,679, 5,359,015, 5,470,811, and 5,719,241 all of which are herein fully incorporated herein reference. In addition, one or more of the catalyst compounds described above or catalyst systems may be used in combination with one or more conventional catalyst compounds or catalyst systems. Non-limiting examples of mixed catalysts and catalyst systems are described in U.S. Pat. Nos. 4,159,965, 4,325,837, 4,701,432, 5,124,418, 5,077,255, 5,183,867, 5,391,660, 5,395,810, 5,691,264, 5,723,399 and 5,767,031 and PCT Publication WO 96/23010 published Aug. 1, 1996, all of which are herein fully incorporated by reference.

Activators and Activation Methods for Catalyst Compounds

Catalyst and pre-catalyst compounds as described above, may be activated in various ways to yield compounds having a vacant coordination site that will coordinate, insert, and polymerize olefin(s). For the purposes of this patent specification and appended claims, the terms "cocatalyst" and "activator" are used herein interchangeably and are defined to be any compound which can activate any one of the pre-catalyst and/or catalyst compounds described above into a catalytically active catalyst compound, and/or catalytically active ionic compound.

Activators may include alumoxanes, aluminum alkyls, ionizing activators, which may be neutral or ionic, and cocatalysts. Preferred activators include alumoxane compounds, modified alumoxane compounds, and ionizing anion precursor compounds that abstract one reactive, σ-bound, metal ligand, making the metal complex cationic and providing a charge-balancing noncoordinating or weakly coordinating anion.

When a support is present, the support is preferably combined with an activator to produce a catalyst support. Accordingly, the catalyst support preferably comprises a support bound activator. When the support comprises silica, a silica bound activator may be formed. Combination of the catalyst support (i.e., support+activator) with a catalyst precursor forms a catalyst system.

Preferred olefin oligomerization and/or polymerization catalyst systems comprising the catalyst support disclosed herein may contain a formal anionic ligand, such as hydride or hydrocarbyl, with an adjacent (cis) coordination site accessible to an unsaturated monomer. Coordination of an unsaturated monomer to the cis coordination site allows a migratory insertion reaction to form a metal alkyl. Repetition of this process causes chain growth.

Accordingly, the catalyst or catalyst systems are preferably prepared by combining at least two components. In one preferred method, the pre-catalyst (referred to herein as the first component) is preferably a cyclopentadienyl derivative of a Group 4 metal compound containing at least one ligand which will combine with the activator (referred to herein as the second component), or at least a portion thereof such as a cation portion thereof. The second component may be an ion-exchange compound comprising a cation which preferably will irreversibly react with at least one ligand contained in said Group 4 metal compound (first component) and a non-coordinating anion which is preferably a single coordination complex comprising a plurality of lipophilic radicals covalently coordinated to and shielding a central formally charge-bearing metal and/or a metalloid atom or an anion comprising a plurality of boron atoms such as polyhedral boranes, carboranes and metallacarboranes.

Suitable anions for the second component may be any stable and bulky anionic complex, preferably having the following molecular attributes: 1) the anion should have a molecular diameter greater than 4 angstroms; 2) the anion should form stable ammonium salts; 3) the negative charge on the anion should be delocalized over the framework of the anion or be localized within the core of the anion; 4) the anion should be a relatively poor nucleophile; and 5) the anion should not be a powerful reducing to oxidizing agent. Anions meeting these criteria include polynuclear boranes, carboranes, metallacarboranes, polyoxoanions and other various anionic coordination complexes.

The cation portion of the second component may comprise Bronsted acids such as protons or protonated Lewis bases, and/or Lewis acids such as ferricinum, tropylium, triphenylcarbenium and/or silver cations.

In another preferred embodiment, the activator is a Lewis-acid complex which will react with at least one ligand of the pre-catalyst, thereby forming an ionic species described in formulae 4-6 with the ligand abstracted from the first component now bound to the second component. Alumoxanes and especially methylalumoxane, the product formed from the reaction of trimethylaluminum in an aliphatic or aromatic hydrocarbon with stoichiometric quantities of water, are particularly preferred Lewis-acid second components. Modified alumoxanes are also preferred. Alumoxanes and methods for preparation are illustrated by, for example, U.S. Pat. Nos. 4,542,199; 4,544,762; 5,015,749; and 5,041,585. A technique for preparing modified alumoxanes has been disclosed in U.S. Pat. No. 5,041,584, in EPA 0 516 476, and in EPA 0 561 476, which are incorporated by reference herein.

Upon combination of the pre-catalyst and the activator, the activator preferably reacts with one of the ligands of the pre-catalyst, thereby generating an anion pair consisting of a Group 4 metal cation and the aforementioned anion, which anion is compatible with and non-coordinating towards the Group 4 metal cation formed from the pre-catalyst. The anion of the activator preferably is capable of stabilizing the Group 4 metal cation's ability to function as a catalyst and is preferably sufficiently labile to permit displacement by an olefin, diolefin or an acetylenically unsaturated monomer during polymerization. See for example, U.S. Pat. Nos. 4,808,561; 4,897,455; 5,057,475; U.S. patent application Ser. No. 459, 921 (published as PCT International publication WO 91/09882), Canadian Patent 1,268,753, U.S. Pat. No. 5,240, 894 and WO 94 03506, all directed to supported catalysts and the methods to produce the same, all of which are herein incorporated by reference.

Activation of a catalyst can be achieved by removal of formal anionic or neutral ligands of higher binding affinity than the unsaturated monomer. This removal process, referred to as abstraction, may have a kinetic rate that is first-order or non-first order with respect to the activator. Accordingly, activators that remove formal anionic ligands are termed ionizing activators. Activators that remove formal neutral ligands are termed non-ionizing activators. Activators are preferably strong Lewis-acids, which may play either the role of ionizing or non-ionizing activator.

Activation may be a one step or multi step process. One step in this process may include coordinating a hydride or hydrocarbyl group to a metal complex. A separate activation step is removal of formal anionic or neutral ligands of higher binding affinity than the unsaturated monomer. These activation steps may occur in series or in parallel. These steps may also occur in the presence of olefin, and/or prior to exposure to olefin. More than one sequence of activation steps may be possible to achieve activation.

The activator may also act to coordinate a hydride or hydrocarbyl group to a catalyst. Activation may be effected by substitution of catalyst functional groups with a hydride, hydrocarbyl or substituted hydrocarbyl group. This substitution may be effected with appropriate hydride or alkyl reagents of group 1, 2, 12, and/or 13 elements. To achieve activation, it may be necessary to also remove formal anionic or neutral ligands of higher binding affinity than the particular unsaturated monomer being used.

The activator may also act to coordinate a hydride or hydrocarbyl group to the catalyst. If the catalyst does not contain formal anionic ligands, then a hydride, hydrocarbyl or substituted hydrocarbyl may be coordinated to a metal using electrophilic proton or alkyl transfer reagents represented by $H^+(LB)_nA^-$, $(R^4)^+(LB)_nA^-$. $R^4$ is a hydrocarbyl or a substituted hydrocarbyl; LB is a Lewis-base, n=0, 1 or 2. Non-limiting examples of preferred Lewis-bases include diethyl ether, dimethyl ether, ethanol, methanol, water, acetonitrile, and/or N,N-dimethylaniline. $A^-$ is an anion, preferably a substituted hydrocarbon, a functional group, or a non-coordinating anion. Non-limiting examples of $A^-$ include halides, carboxylates, phosphates, sulfates, sulfonates, borates, aluminates, alkoxides, thioalkoxides, anionic substituted hydrocarbons, and/or anionic metal complexes.

Aluminoxane and Aluminum Alkyl Activators

In one embodiment, alumoxanes activators are utilized as an activator in the catalyst composition of the invention. Alumoxanes are generally oligomeric compounds containing —Al($R^1$)—O— sub-units, where $R^1$ is an alkyl group. Examples of alumoxanes include methylalumoxane (MAO), modified methylalumoxane (MMAO), ethylalumoxane and isobutylalumoxane. Alkylalumoxanes and modified alkylalumoxanes are suitable as catalyst activators, particularly when the abstractable ligand is a halide, alkoxide or amide. Mixtures of different alumoxanes and modified alumoxanes may also be used.

The activator compounds comprising Lewis-acid activators and in particular alumoxanes are represented by the following general formulae:

$$(R^3-Al-O)_p \tag{11}$$

$$R^4(R^5-Al-O)_p-AlR^6_2 \tag{12}$$

$$(M')^{m+}Q'_m \tag{13}$$

An alumoxane is generally a mixture of both the linear and cyclic compounds. In the general alumoxane formula, $R^3$, $R^4$, $R^5$ and $R^6$ are, independently a $C_1$-$C_{30}$ alkyl radical, for example, methyl, ethyl, propyl, butyl, pentyl, hexyl, heptyl, octyl, nonyl, decyl, and "p" is an integer from 1 to about 50. Most preferably, $R^3$, $R^4$, $R^5$ and $R^6$ are each methyl and "p" is a least 4. When an alkyl aluminum halide or alkoxide is employed in the preparation of the alumoxane, one or more $R^3$ groups may be halide or alkoxide. M' is a metal or metalloid, and Q' is a partially or fully fluorinated hydrocarbyl.

It is recognized that alumoxane is not a discrete material. A typical alumoxane will contain free trisubstituted or trialkyl aluminum, bound trisubstituted or trialkyl aluminum, and alumoxane molecules of varying degree of oligomerization. Those methylalumoxanes most preferred contain lower levels of trimethylaluminum. Lower levels of trimethylaluminum can be achieved by reaction of the trimethylaluminum with a Lewis base or by vacuum distillation of the trimethylaluminum or by other similar means. It is also recognized that after reaction with the transition metal compound, some alumoxane molecules are in the anionic form as represented by the anion in equations 4-6, thus for our purposes are considered "non-coordinating" anions. For further descriptions, see U.S. Pat. Nos. 4,665,208, 4,952,540, 5,041,584, 5,091,352, 5,206,199, 5,204,419, 4,874,734, 4,924,018, 4,908,463, 4,968,827, 5,329,032, 5,248,801, 5,235,081, 5,157,137,5,103,031 and EP 0561 476 A1, EP 0279586 B1, EP 0516476 A, EP 0 594 218 A1 and WO 94/10180.

When the activator is an alumoxane (modified or unmodified), some embodiments select the maximum amount of activator at a 5000-fold molar excess Al/M over the catalyst precursor (per metal catalytic site). The preferred minimum activator-to-catalyst-precursor molar ratio is 1:1.

Alumoxanes may be produced by the hydrolysis of the respective trialkylaluminum compound. MMAO may be produced by the hydrolysis of trimethylaluminum and a higher trialkylaluminum such as triisobutylaluminum. MMAO's are generally more soluble in aliphatic solvents and more stable during storage. There are a variety of methods for preparing alumoxane and modified alumoxanes, non-limiting examples of which are described in U.S. Pat. Nos. 4,665,208, 4,952, 540, 5,091,352, 5,206,199, 5,204,419, 4,874,734, 4,924,018, 4,908,463, 4,968,827, 5,308,815, 5,329,032, 5,248,801, 5,235,081, 5,157,137, 5,103,031, 5,391,793, 5,391,529, 5,693,838, 5,731,253, 5,731,451, 5,744,656, 5,847,177, 5,854,166, 5,856,256 and 5,939,346 and European publications EP-A-0 561 476, EP-B1-0 279 586, EP-A-0 594-218 and EP-B1-0 586 665, and PCT publications WO 94/10180 and WO 99/15534, all of which are herein fully incorporated by reference.

Modified methyl alumoxane (MMAO) cocatalyst type 3A (commercially available from Akzo Chemicals, Inc. under the trade name Modified Methylalumoxane type 3A, covered under patent number U.S. Pat. No. 5,041,584) may also be suitable for use herein. Aluminum alkyl or organoaluminum compounds which may be utilized as activators (or scavengers) may also include trimethylaluminum, triethylaluminum, triisobutylaluminum, tri-n-hexylaluminum, tri-n-octylaluminum and the like.

Ionizing Activators

It is within the scope of this invention to use an ionizing or stoichiometric activator, neutral or ionic, such as tri(n-butyl) ammonium tetrakis (pentafluorophenyl)boron, a trisperfluorophenyl boron metalloid precursor or a trisperfluoronaphtyl boron metalloid precursor, polyhalogenated heteroborane anions (WO 98/43983), boric acid (U.S. Pat. No. 5,942,459) or combination thereof. It is also within the scope of this invention to use neutral or ionic activators alone or in combination with alumoxane or modified alumoxane activators.

Examples of neutral stoichiometric activators include trisubstituted boron, tellurium, aluminum, gallium and indium or mixtures thereof. The three substituent groups are each independently selected from alkyls, alkenyls, halogen, substituted alkyls, aryls, arylhalides, alkoxy and halides. Preferably, the three groups are independently selected from halogen, mono or multicyclic (including halosubstituted)aryls, alkyls, and alkenyl compounds and mixtures thereof, preferred are alkenyl groups having 1 to 20 carbon atoms, alkyl groups having 1 to 20 carbon atoms, alkoxy groups having 1 to 20 carbon atoms and aryl groups having 3 to 20 carbon atoms (including substituted aryls). More preferably, the three groups are alkyls having 1 to 4 carbon groups, phenyl, napthyl or mixtures thereof. Even more preferably, the three groups are halogenated, preferably fluorinated, aryl groups. Most preferably, the neutral stoichiometric activator is trisperfluorophenyl boron or trisperfluoronapthyl boron.

Ionic stoichiometric activator compounds may contain an active proton, or some other cation associated with, but not coordinated to, or only loosely coordinated to, the remaining ion of the ionizing compound. Such compounds and the like are described in European publications EP-A-0 570 982, EP-A-0 520 732, EP-A-0 495 375, EP-B1-0 500 944, EP-A-0 277 003 and EP-A-0 277 004, and U.S. Pat. Nos. 5,153,157, 5,198,401, 5,066,741, 5,206,197, 5,241,025, 5,384,299 and 5,502,124 and U.S. patent application Ser. No. 08/285,380, filed Aug. 3, 1994, all of which are herein fully incorporated by reference.

Ionic catalysts can be preparedly reacting a transition metal compound with some neutral Lewis acids, such as $B(C_6F_6)_3$, which upon reaction with the hydrolyzable ligand (X) of the transition metal compound forms an anion, such as $([B(C_6F_5)_3(X)]^-)$, which stabilizes the cationic transition metal species generated by the reaction. The catalysts can be, and preferably are, prepared with activator components which are ionic compounds or compositions. However preparation of activators utilizing neutral compounds is also contemplated by this invention.

Compounds useful as an activator component in the preparation of the ionic catalyst systems used in the process of this invention preferably comprise a cation, which is preferably a Bronsted acid capable of donating a proton, and a compatible non-coordinating anion which anion is relatively large (bulky), capable of stabilizing the active catalyst species (the Group 4 cation) which is formed when the two compounds are combined and said anion will be sufficiently labile to be displaced by olefinic diolefinic and acetylenically unsaturated substrates or other neutral Lewis bases such as ethers, nitrites and the like. For example, compatible non-coordinating anions as disclosed in EPA 277,003 and EPA 277,004 published 1988: 1) anionic coordination complexes comprising a plurality of lipophilic radicals covalently coordinated to and shielding a central charge-bearing metal or metalloid core, and 2) anions comprising a plurality of boron atoms such as carboranes, metallacarboranes and boranes may be suitable for use herein.

In a preferred embodiment, the stoichiometric activators include a cation and an anion component, and may be represented by the following formula:

(14)

wherein L is an neutral Lewis base;
H is hydrogen;
$(L-H)^+$ is a Bronsted acid $A^{d-}$ is a non-coordinating anion having the charge d−
d is an integer from 1 to 3.

The cation component, $(L-H)_d^+$ may include Bronsted acids such as protons or protonated Lewis bases or reducible Lewis acids capable of protonating or abstracting a moiety, such as an alkyl or aryl, from the bulky ligand metallocene containing transition metal catalyst precursor, resulting in a cationic transition metal species.

The activating cation $(L-H)_d^+$ may be a Bronsted acid, capable of donating a proton to the transition metal catalytic precursor resulting in a transition metal cation, including ammoniums, oxoniums, phosphoniums, silyliums, and mixtures thereof, preferably ammoniums of methylamine, aniline, dimethylamine, diethylamine, N-methylaniline, diphenylamine, trimethylamine, triethylamine, N,N-dimethylaniline, methyldiphenylamine, pyridine, p-bromo N,N-dimethylaniline, p-nitro-N,N-dimethylaniline, phosphoniums from triethylphosphine, triphenylphosphine, and diphenylphosphine, oxomiuns from ethers such as dimethyl ether diethyl ether, tetrahydrofuran and dioxane, sulfoniums from thioethers, such as diethyl thioethers and tetrahydrothiophene, and mixtures thereof. The activating cation $(L-H)_d^+$ may also be a moiety such as silver, tropylium, carbeniums, ferroceniums and mixtures, preferably carboniums and ferroceniums. Most preferably $(L-H)_d^+$ is triphenyl carbonium.

The anion component $A^{d-}$ include those having the formula $[M^{k+}Q_n]^{d-}$ wherein k is an integer from 1 to 3; n is an integer from 2-6; n-k=d; M is an element selected from Group 13 of the Periodic Table of the Elements, preferably boron or aluminum, and Q is independently a hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q having up to 20 carbon atoms with the proviso that in not more than 1 occurrence is Q a halide. Preferably, each Q is a fluorinated hydrocarbyl group having 1 to 20 carbon atoms, more preferably each Q is a fluorinated aryl group, and most preferably each Q is a pentafluoryl aryl group. Examples of suitable $A^{d-}$ also include diboron compounds as disclosed in U.S. Pat. No. 5,447,895, which is fully incorporated herein by reference.

Illustrative, but not limiting examples of boron compounds which may be used as an activating cocatalyst include tri-substituted ammonium salts such as:
trimethylammonium tetraphenylborate, triethylammonium tetraphenylborate, tripropylammonium tetraphenylborate, tri(n-butyl)ammonium tetraphenylborate, tri(t-butyl)ammonium tetraphenylborate, N,N-dimethylanilinium tetraphenylborate, N,N-diethylanilinium tetraphenylborate, N,N-dimethyl-(2,4,6-trimethylanilinium)tetraphenylborate, tropillium tetraphenylborate, triphenylcarbenium tetraphenylborate, triphenylphosphonium tetraphenylborate triethylsilylium tetraphenylborate, benzene(diazonium) tetraphenylborate, trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium) tetrakis(pentafluorophenyl)borate, tropillium tetrakis (pentafluorophenyl)borate, triphenylcarbenium tetrakis (pentafluorophenyl)borate, triphenylphosphonium tetrakis (pentafluorophenyl)borate, triethylsilylium tetrakis (pentafluorophenyl)borate, benzene(diazonium) tetrakis (pentafluorophenyl)borate, trimethylammonium tetrakis-(2,3,4,6-tetrafluorophenyl)borate, triethylammonium tetrakis-(2,3,4,6-tetrafluorophenyl)borate, tripropylammonium tetrakis-(2,3,4,6-tetrafluorophenyl)borate, tri(n-butyl)ammonium tetrakis-(2,3,4,6-tetrafluoro-phenyl)borate, dimethyl(t-butyl)ammonium tetrakis-(2,3,4,6-tetrafluorophenyl)borate, N,N-dimethylanilinium tetrakis-(2,3,4,6-tetrafluorophenyl)borate, N,N-diethylanilinium tetrakis-(2,3,4,6-tetrafluorophenyl)borate, N,N-dimethyl-(2,4,6-trimethylanilinium)tetrakis-(2,3,4,6-tetrafluorophenyl)borate, tropillium tetrakis-(2,3,4,6-tetrafluorophenyl)borate, triphenylcarbenium tetrakis-(2,3,4,6-tetrafluorophenyl)borate, triphenylphosphonium tetrakis-(2,3,4,6-tetrafluorophenyl)borate, triethylsilylium tetrakis-(2,3,4,6-tetrafluorophenyl)borate, benzene(diazonium)tetrakis-(2,3,4,6-tetrafluorophenyl)borate, trimethylammonium tetrakis(perfluoronapthyl)borate, triethylammonium tetrakis(perfluoronapthyl)borate, tripropylammonium tetrakis(perfluoronapthyl)borate, tri(n-butyl)ammonium tetrakis(perfluoronapthyl)borate, tri(t-butyl)ammonium tetrakis(perfluoronapthyl)borate, N,N-dimethylanilinium tetrakis(perfluoronapthyl)borate, N,N-diethylanilinium tetrakis(perfluoronapthyl)borate, N,N-dimethyl-(2,4,6-trimethylanilinium) tetrakis(perfluoronapthyl)borate, tropillium tetrakis(perfluoronapthyl)borate, triphenylcarbenium tetrakis(perfluoronapthyl)borate, triphenylphosphonium tetrakis (perfluoronapthyl)borate, triethylsilylium tetrakis (perfluoronapthyl)borate, benzene(diazonium)tetrakis (perfluoronapthyl)borate, trimethylammonium tetrakis (perfluorobiphenyl)borate, triethylammonium tetrakis (perfluorobiphenyl)borate, tripropylammonium tetrakis (perfluorobiphenyl)borate, tri(n-butyl)ammonium tetrakis (perfluorobiphenyl)borate, tri(t-butyl)ammonium tetrakis (perfluorobiphenyl)borate, N,N-dimethylanilinium tetrakis(perfluorobiphenyl)borate, N,N-diethylanilinium tetrakis(perfluorobiphenyl)borate, N,N-dimethyl-(2,4,6-trimethylanilinium) tetrakis(perfluorobiphenyl)borate, tropillium tetrakis(perfluorobiphenyl)borate, triphenylcarbenium tetrakis(perfluorobiphenyl)borate, triphenylphosphonium tetrakis(perfluorobiphenyl)borate, triethylsilylium tetrakis(perfluorobiphenyl)borate, benzene (diazonium) tetrakis(perfluorobiphenyl)borate, trimethylammonium tetrakis(3,5-bis(trifluoromethyl)phenyl)borate, triethylammonium tetrakis(3,5-bis(trifluoromethyl)phenyl)borate, tripropylammonium tetrakis(3,5-bis (trifluoromethyl)phenyl)borate, tri(n-butyl)ammonium tetrakis(3,5-bis(trifluoromethyl)phenyl)borate, tri(t-butyl) ammonium tetrakis(3,5-bis(trifluoromethyl)phenyl)borate, N,N-dimethylanilinium tetrakis(3,5-bis(trifluoromethyl)phenyl)borate, N,N-diethylanilinium tetrakis(3,5-bis(trifluoromethyl)phenyl)borate, N,N-dimethyl-(2,4,6-trimethylanilinium) tetrakis(3,5-bis(trifluoromethyl) phenyl)borate, tropillium tetrakis(3,5-bis(trifluoromethyl) phenyl)borate, triphenylcarbenium tetrakis(3,5-bis (trifluoromethyl)phenyl)borate, triphenylphosphonium tetrakis(3,5-bis(trifluoromethyl)phenyl)borate, triethylsilylium tetrakis(3,5-bis(trifluoromethyl)phenyl)borate, benzene(diazonium)tetrakis(3,5-bis(trifluoromethyl)phenyl)borate, and dialkyl ammonium salts such as: di-(i-propyl)ammonium tetrakis(pentafluorophenyl)borate, and dicyclohexylammonium tetrakis(pentafluorophenyl)borate; and additional tri-substituted phosphonium salts such as tri(o-tolyl)phosphonium tetrakis(pentafluorophenyl) borate, tri(2,6-dimethylphenyl)phosphonium tetrakis(pentafluorophenyl)borate, and combinations comprising at least one of the foregoing.

Most preferably, the ionic stoichiometric activator $(L-H)_d^+ (A^{d-})$ is N,N-dimethylanilinium tetra(perfluorophenyl)borate, N,N-dimethylanilinium tetrakis(perfluoronapthyl)borate, N,N-dimethylanilinium tetrakis(perfluorobiphenyl)borate, N,N-dimethylanilinium tetrakis(3,5-bis (trifluoromethyl)phenyl)borate, triphenylcarbenium tetrakis (perfluoronapthyl)borate, triphenylcarbenium tetrakis (perfluorobiphenyl)borate, triphenylcarbenium tetrakis(3,5-bis(trifluoromethyl)phenyl)borate, or triphenylcarbenium tetra(perfluorophenyl)borate.

In one embodiment, an activation method using ionizing ionic compounds not containing an active proton but capable of producing a bulky ligand metallocene catalyst cation and their non-coordinating anion are also contemplated, and are described in EP-A-0 426 637, EP-A-0 573 403 and U.S. Pat. No. 5,387,568, which are all herein incorporated by reference.

The term "non-coordinating anion" (NCA) means an anion which either does not coordinate to said cation or which is only weakly coordinated to said cation thereby remaining sufficiently labile to be displaced by a neutral Lewis base. "Compatible" non-coordinating anions are those which are not degraded to neutrality when the initially formed complex decomposes. Further, the anion will not transfer an anionic substituent or fragment to the cation so as to cause it to form a neutral four coordinate metallocene compound and a neutral by-product from the anion. Non-coordinating anions useful in accordance with this invention are those that are compatible, stabilize the metallocene cation in the sense of balancing its ionic charge at +1, yet retain sufficient lability to permit displacement by an ethylenically or acetylenically unsaturated monomer during polymerization. These types of cocatalysts sometimes use tri-isobutyl aluminum or tri-octyl aluminum as a scavenger.

Invention process also can employ cocatalyst compounds or activator compounds that are initially neutral Lewis acids but form a cationic metal complex and a noncoordinating anion, or a zwitterionic complex upon reaction with the invention compounds. For example, tris(pentafluorophenyl) boron or aluminum act to abstract a hydrocarbyl or hydride ligand to yield an invention cationic metal complex and stabilizing noncoordinating anion, see EP-A-0 427 697 and EP-A-0 520 732 for illustrations of analogous Group-4 metallocene compounds. Also, see the methods and compounds of EP-A-0 495 375. For formation of zwitterionic complexes using analogous Group 4 compounds, see U.S. Pat. Nos. 5,624,878; 5,486,632; and 5,527,929.

When the cations of noncoordinating anion precursors are Bronsted acids such as protons or protonated Lewis bases (excluding water), or reducible Lewis acids such as ferrocenium or silver cations, or alkali or alkaline earth metal cations such as those of sodium, magnesium or lithium, the catalyst-precursor-to-activator molar ratio may be any ratio. Combinations of the described activator compounds may also be used for activation. For example, tris(perfluorophenyl) boron can be used with methylalumoxane.

Conventional-Type Cocatalysts (Activators)

Transition metal catalyst compounds may also be activated with one or more cocatalysts represented by the formula:

$$M^3M^4{}_vX^2{}_cR^2{}_{b-c} \quad (15)$$

wherein $M^3$ is a metal from Group 1 to 3 and 12 to 13 of the Periodic Table of Elements; $M^4$ is a metal of Group 1 of the Periodic Table of Elements; v is a number from 0 to 1; each $X^2$ is any halogen; c is a number from 0 to 3; each $R^2$ is a monovalent hydrocarbon radical or hydrogen; b is a number from 1 to 4; and wherein b minus c is at least 1. Other conventional-type organometallic cocatalyst compounds for the above conventional-type transition metal catalysts have the formula $M^3R^2{}_k$, where $M^3$ is a Group IA, IIA, IIB or IIIA metal, such as lithium, sodium, beryllium, barium, boron, aluminum, zinc, cadmium, and gallium; k equals 1, 2 or 3 depending upon the valency of $M^3$ which valency in turn normally depends upon the particular Group to which $M^3$ belongs; and each $R^2$ may be any monovalent hydrocarbon radical.

Non-limiting examples of organometallic cocatalyst compounds useful with conventional-type catalyst compounds include methyllithium, butyllithium, dihexylmercury, butylmagnesium, diethylcadmium, benzylpotassium, diethylzinc, tri-n-butylaluminum, diisobutyl ethylboron, diethylcadmium, di-n-butylzinc and tri-n-amylboron, and, in particular, the aluminum alkyls, such as tri-hexyl-aluminum, triethylaluminum, trimethylaluminum, and tri-isobutylaluminum. Other suitable cocatalyst compounds include mono-organohalides and hydrides of Group 2 metals, and mono- or di-organohalides and hydrides of Group 3 and 13 metals. Non-limiting examples of such conventional-type cocatalyst compounds include di-isobutylaluminum bromide, isobutylboron dichloride, methyl magnesium chloride, ethylberyllium chloride, ethylcalcium bromide, di-isobutylaluminum hydride, methylcadmium hydride, diethylboron hydride, hexylberyllium hydride, dipropylboron hydride, octylmagnesium hydride, butylzinc hydride, dichloroboron hydride, di-bromo-aluminum hydride and bromocadmium hydride. A more complete discussion of conventional-type organometallic cocatalyst compounds may be found in U.S. Pat. Nos. 3,221,002 and 5,093,415, which are herein fully incorporated by reference.

Additional Activators

Other activators include those described in PCT publication WO 98/07515 such as tris(2,2',2"-nonafluorobiphenyl) fluoroaluminate, which publication is fully incorporated herein by reference. Combinations of activators are also contemplated by the invention, for example, alumoxanes and ionizing activators in combinations, see for example, EP-B1 0 573 120, PCT publications WO 94/07928 and WO 95/14044 and U.S. Pat. Nos. 5,153,157 and 5,453,410 all of which are herein fully incorporated by reference.

Other suitable activators are disclosed in WO 98/09996, incorporated herein by reference, which describes activating bulky ligand metallocene catalyst compounds with perchlorates, periodates and iodates including their hydrates. WO 98/30602 and WO 98/30603, incorporated by reference, describe the use of lithium (2,2'-bisphenyl-ditrimethylsilicate).4THF as an activator for a bulky ligand metallocene catalyst compound. WO 99/18135, incorporated herein by reference, describes the use of organo-boron-aluminum acitvators. EP-B 1-0 781 299 describes using a silylium salt in combination with a non-coordinating compatible anion. Also, methods of activation such as using radiation (see EP-B 1-0 615 981 herein incorporated by reference), electrochemical oxidation, and the like are also contemplated as activating methods for the purposes of rendering the neutral bulky ligand metallocene catalyst compound or precursor to a bulky ligand metallocene cation capable of polymerizing olefins. Other activators or methods for activating a bulky ligand metallocene catalyst compound are described in for example, U.S. Pat. Nos. 5,849,852, 5,859,653 and 5,869,723 and WO 98/32775, WO 99/42467 (dioctadecylmethylammonium-bis (tris(pentafluorophenyl)borane) benzimidazolide), which are herein incorporated by reference.

Suitable ion forming, activating cocatalyst comprises a salt of a cationic oxidizing agent and a noncoordinating, compatible anion represented by the formula:

$$(OX^{e+})_d(A^{d-})_e \tag{16}$$

wherein $OX^{e+}$ is a cationic oxidizing agent having a charge of e+; e is an integer from 1 to 3; and $A^-$ and d are as previously defined. Examples of cationic oxidizing agents include: ferrocenium, hydrocarbyl-substituted ferrocenium, $Ag^+$, or $Pb^{+2}$. Preferred embodiments of $A^{d-}$ are those anions previously defined with respect to the Bronsted acid containing activators, especially tetrakis(pentafluorophenyl)borate.

It within the scope of this invention that catalyst compounds can be combined one or more activators or activation methods described above. For example, a combination of activators have been described in U.S. Pat. Nos. 5,153,157 and 5,453,410, European publication EP-B1 0 573 120, and PCT publications WO 94/07928 and WO 95/14044. These documents all discuss the use of an alumoxane and an ionizing activator with a bulky ligand metallocene catalyst compound.

Supports

When present, the support material is preferably porous, more preferably a porous solid having a chemically significant amount of hydroxyl functionality. A porous material, as used herein, adsorbs at least about 1 gram of a small molecule such as argon, nitrogen, n-hexane, cyclohexane, or benzene per 100 grams of the material. A working definition of a support having a chemically significant amount of hydroxyl functionality preferably includes a support having a sufficient amount of hydroxyls so as to allow for association of an amount of catalyst to the support that is sufficient to polymerize an olefin under polymerization conditions.

Preferred support materials include inorganic oxides comprising Group 2, 3, 4, 5, 13 or 14 metal oxides. Particularly preferred supports include silica, fumed silica, modified alumina (WO 99/60033), silica-alumina, and mixtures comprising silica.

Accordingly, inorganic oxides, preferably including silica, that retain hydroxyl groups after dehydration and/or deactivation treatment methods may be suitable in accordance with the present invention. Various forms of silica including powders, particles, gels, extrudates, and/or beads may be used.

Preferred metal oxide compositions may additionally contain oxides of other metals, such as those of Al, K, Mg, Na, Ti and Zr. Metal oxides used herein are preferably treated by thermal and/or chemical means to remove water and free oxygen. Treatments may include applying vacuum in a heated oven, being heated in a fluidized bed and/or being contacted (chemically treated) with one or more dehydrating, deactivating, and/or capping agents such as organosilanes, siloxanes, alkyl aluminum compounds, and the like. The level of treatment should be such that as much retained moisture and oxygen as is possible is removed, but that a chemically significant amount of hydroxyl functionality is retained by the support.

Silica may be combined with other support materials including magnesia, titania, zirconia, magnesium chloride (U.S. Pat. No. 5,965,477), montmorillonite (European Patent EP-B 10 511 665), phyllosilicate, zeolites, talc, clays (U.S. Pat. No. 6,034,187) and the like. Additional support materials may include porous acrylic polymers described in EP 0 767 184 B 1, which is incorporated herein by reference. Other support materials include nanocomposites as described in PCT WO 99/47598, aerogels as described in WO 99/48605, spherulites as described in U.S. Pat. No. 5,972,510 and polymeric beads as described in WO 99/50311, which are all herein incorporated by reference.

Also, the support may comprise a frangible, spray dried agglomerate catalyst supports of silica gel, which possess a controlled morphology of microspheroidal shape, rough scabrous appearance, and interstitial void spaces which penetrate the agglomerate surface and are of substantially uniform size and distribution, as described in WO 97/48743. Such agglomerates may possess a 1-250 micron particle size, 1-1000 m²/g surface area, and an Attrition Quality Index (AQI) of at least 10. Agglomerates may be are derived from a mixture of dry milled inorganic oxide particles, e.g., silica gel and optionally but preferably wet milled inorganic oxide particles, e.g., silica gel particles (which preferably contain a colloidal content of less than 1 micron particle), slurried in water for spray drying.

The support may also comprise bodies made by preparing a mixture of particles of bound clay with one or more ingredients including silica as an inorganic binder. Preferably the particles are formed by spray drying and porosity is introduced into the bodies during their assembly, and results primarily from spaces between the starting particles. See for example U.S. Pat. Nos. 5,395,808 5,569,634; 5,403,799; and 5,403,809; and EP 92/490 226.

The support may also comprise undehydrated silica as disclosed in U.S. Pat. No. 5,238,892. Further, the support may include clay, clay minerals, ion exchanging layered compounds, diatomaceous earth, silicates and zeolites, subjected to chemical treatment, which utilizes ion exchangeability to substitute interlaminar exchangeable ions of the clay with other large bulky ions to obtain a layered substance having the interlaminar distance enlarged. Preferably, the bulky ions play the role of pillars, supporting the layered structure, (and are therefore referred to herein as pillars). Preferred guest compounds include cationic inorganic compounds derived from titanium tetrachloride, zirconium tetrachloride, and $SiO_2$. See for example U.S. Pat. No. 5,308,811.

Other forms of the support may comprise a clay mineral modified with a compound capable of introducing a cation into the layer interspaces of the clay mineral. Suitable cations which are inserted into the clay include those having a proton, namely, Bronsted acids such trimethylammonium, as well as carbonium ions, oxonium ions, and sulfonium ions. Representative anions include chlorine ion, bromide ion, and iodide ion. See for example U.S. Pat. No. 5,830,820.

Dried solid compositions comprising clay particles and inorganic metal oxide particles substantially segregated from the clay particles may also be used. Preferably, the metal oxide particles are sol particles which tend to fuse upon sintering. Consequently, by segregating the sol particles with smectite-type clay particles, fusion of the sol particles is reduced under sintering conditions thereby preventing a loss of surface area. The preferred metal oxide is colloidal silica having an average particle size between 40 and 800 angstroms (0.004 and 0.08 microns), preferably 40 and 80 angstroms. The ratio of the metal oxide to clay is preferably between about 1:1 to 20:1, preferably 4:1 to 10:1. The end product is preferably described as a sol particle-clay composite in which the clay platelets inhibit aggregation of the sol particles. Such products are preferably made up entirely of irregular sol-clay networks in which the clay platelets are placed between the sol particles. Accordingly, a composite with very high surface area, and ability to retain such high surface area at elevated temperatures results. See for example U.S. Pat. No. 4,981,825.

Still other suitable supports include fibrous clays and precalcined oxides prepared by forming a fluid suspension of the clay with the precalcined oxide particles, agitating the suspension to form a co-dispersion, and shaping and drying the co-dispersion. Suitable fibrous clays include aluminosilicates, magnesium silicates, and aluminomagnesium silicates. Examples of suitable fibrous clays are attapulgite, playgorskite, sepiolite, haloysite, endellite, chrysotile asbestos, and imogolite. Suitable oxides include silica. The ratio of fibrous clay to precalcined oxide may vary from 20:1 to 1:5 by weight. See for example U.S. Pat. No. 4,375,406. The support may also comprise agglomerate composite particles of an inorganic oxide, preferably silica, and an ion exchanging layered compound such as clay, as described in U.S. Pat. No. 6,559,090.

It is preferred that the support material have a surface area, as determined by nitrogen porosimetry using the B.E.T. method, in the range of from about 10 to about 1000 m$^2$/g. Within this range, a surface area of less than or equal to about 700 can be employed, with less than or equal to about 500 preferred, and less than or equal to about 400 more preferred. Also preferred within this range is a surface area of greater than or equal to about 50, with greater than or equal to about 100 more preferred, and greater than or equal to about 300 especially preferred.

The pore volume of the support, as determined by nitrogen adsorption, is preferably in the range of from about 0.1 to about 4.0 cc/g. Within this range, a pore volume of less than or equal to about 3.5 can be employed, with less than or equal to about 3 preferred. Also preferred within this range is a pore volume of greater than or equal to about 0.5, with greater than or equal to about 0.8 more preferred.

The average particle size of the support is preferably in the range of from about 0.1 to about 500 micrometers. Within this range, an average particle size of less than or equal to about 200 can be employed, with less than or equal to about 100 preferred. Also preferred within this range is an average particle size of greater than or equal to about 1, with greater than or equal to about 5 more preferred.

It is preferred that the inorganic solid having hydroxyl groups on the surface thereof to be used in the present invention does not contain water such as crystal water or adsorbed water. Accordingly, the support material may be subjected to a heat treatment and/or chemical treatment to reduce the water content or the hydroxyl content of the support material. However, the presence of water in the support materials does not preclude the use of the support materials in the present invention.

Any water contained in the inorganic solid can be removed therefrom by heating, preferably in a nitrogen atmosphere or under reduced pressure, at 250° C. or more for 1 hour or more.

In a preferred embodiment, the support may be calcined by heating in an inert atmosphere at a temperature, and for a period of time sufficient to reduce the number of hydroxyl groups. Such treatment may be under vacuum in a heated oven, in a heated fluidized bed or the like. The level of treatment should be such that as much retained moisture and oxygen as is possible is removed, but that a chemically significant amount of hydroxyl functionality is retained. Thus calcining at up to a point prior to decomposition of the support material, for several hours is permissible. If higher loading of supported anionic activator is desired, lower calcining temperatures for lesser times may be suitable. Where the metal oxide is silica, loadings to achieve from less than or equal to about 0.1 mmol to about 3.0 mmol activator/g SiO$_2$ are typically suitable and can be achieved, for example, by varying the temperature of calcining from about 200° C. to about 800° C. See, for example, Zhuralev, et al, Langmuir 1987, vol. 3, 316 where correlation between calcining temperature and times and hydroxyl contents of silicas of varying surface areas is described.

The calcining temperature of the support is preferably about 200° C. to about 1000° C. Within this range, a calcining temperature of less than or equal to about 800° C. can be employed, with less than or equal to about 500° C. preferred. Also preferred within this range is a calcining temperature of greater than or equal to about 300° C., with greater than or equal to about 400° C. more preferred. The support may be calcined in an inert atmosphere, in a reducing atmosphere, and/or in an oxidizing atmosphere.

For a support comprising silica, the calcining time can be about 0.5 hours to about 24 hours, depending on the temperature program used to calcine, the atmosphere in which the support is calcined, and the composition of the support itself. Within this range, a calcining time of less than or equal to about 12 hours can be employed, with less than or equal to about 10 hours preferred, and less than or equal to about 8 hours more preferred. Also preferred within this range is a calcining time of greater than or equal to about 2 hours, with greater than or equal to about 4 hours more preferred, and greater than or equal to about 6 hours especially preferred.

The support may also be calcined in the presence of a fluoride-containing compound such as a fluoride salt, as described in U.S. Pat. No. 6,524,988, which is incorporated by reference herein.

Tailoring of hydroxyl groups available as attachment sites on the support can be accomplished by the treatment of the support with a chemical dehydrating and/or deactivation agent, also referred to herein as a capping agent. This chemical treatment is preferably done after calcination. Preferably, a capping agent suitable for use herein is not substantially involved in forming the covalently bound activator. Without wishing to be bound by theory, it is believed that the capping agent replaces or otherwise inactivates the hydrogen on the SiOH functional group by bonding to the oxygen, forming an otherwise inert cap on the silanol group of the substrate (i.e., a cap, which is not involved in polymerization).

After thermal and/or chemical treatment to reduce the number of available hydroxyl groups on the support, the support materials preferably have a hydroxyl content from about 0.001 millimoles per gram (mmol/g) to about 10 mmol/g. Within this range, a hydroxyl content of less than or equal to about 5 can be employed, with less than or equal to about 2 preferred. Also preferred within this range is a hydroxyl content of greater than or equal to about 0.05, with greater than or equal to about 0.1 more preferred.

Preferred silica supports include those with:

a pore size of 1 to 500 Å, preferably 10 to 100 Å, more preferably 25 to 50 Å; and/or an average particle size of 5 to 500 micrometers, preferably 5 to 200 micrometers, more preferably 1 to 100 micrometers; and/or a surface area of 10 to 1000 m$^2$/g, preferably 50 to 500 m$^2$/g, more preferably 100 to 400 m$^2$/g; and/or a pore volume of 0.1 to 4 cc/g, preferably 0.5 to 3.5 cc/g, more preferably 0.8 to 3 cc/g, and/or 0.001 to 10 mmol/g hydroxyl groups, preferably 0.05 to 5 mmol/g, more preferably 0.1 to 2 mmol/g; and/or a pKa of greater than or equal to about 11.

Preferred silica supports include those with a pore size of 1 to 500 Å, an average particle size of 5 to 500 micrometers, a surface area of 10 to 1000 m 2/g, a pore volume of 0.1 to 4 cc/g, 0.001 to 10 mmol/g hydroxyl groups, and a pKa of greater than or equal to 11.

Preferred silica supports include those with a pore size of 10 to 200 Å, an average particle size of 5 to 200 micrometers, a surface area of 50 to 500 m$^2$/g, a pore volume of 0.5 to 3.5 cc/g, 0.05 to 5 mmol/g hydroxyl groups, and a pKa of greater than or equal to 11.

Types of silica suitable for use herein include hydrophilic fumed silica, precipitated silica, colloidal silica, and the like. The silica particles may be powders, granular, spherical, agglomerated, fumed or in other forms. Commercially available silicas that are useful in this invention include those available from Grace Davison (division of W.R. Grace & Co.) under the trade names SYLOID®, SYLOX® DARACLAR®, SYLODENT, TriSyl® SYLOJET®, in particular designations including SD 3216.30, SP-9-10046, Davison Syloid 245, Davison 948 and Davison 952, and the like; Ludox®-HS, -HS40, -HS30, -HS, -TM, -SM, -AM, -AS, -LS, -CL, -CL-X, -SK, -TMA, and the like.

From Degussa AG under the designations: Acematt® HK 125, HK 400, HK 450, HK 460, OK 412, OK 412 LC, OK 500, OK 520, OK 607, TS 100, and the like;

Aerosil 130, 150, 150 V, 200, 200 Pharma, 200 VV Pharma, 300, 380, 90, OX 50, R 104, R 106, R 202, R 711, R 711 VV60, R 7200, R 805, R 805 VV6, R 812, R 812 S, R 812 S VV60, R 812 VV60, R 816, R 816 VV60, R 8200, R 972, R 974, TT 600, and the like; Aerocat®, Aerolyst 350®, Cofill 11, 11-GR, and the like;

Coupsil® 6109, 8113, 8113 GR, and the like;

DYNASYLAN® BH-O, BHN, and the like;

E 39H, EJK 3017, H 10126, H 1044, H 1201; H 1235, and the like;

Sident® 10, 22 S, 8, and the like;

Silicon tetrachloride;

Sipernat® 22 LS, 22 S, 2200, 310, 320, 320 DS, 325 C, 35, 350, 360, 383 DS, 50, 50 S, 500 LS, 570, 700, C 600, C 630, D 10, D 11, D 13, D17, and the like;

Ultrasil® 360, 7000 GR, 7005, 880, VN 2, VN 2 GR, VN 3, VN 3 GR, and the like;

VP Coupsil® 6411, 6508, 8108, and the like;

VP SI 203, VP Si 208, and the like;

From Crossfield under the designation ES 70×, and the like, among others.

Preferred fumed silica is available under the trade name Cabosil TS500, TS530, TS610, TS700, TS720, LM90, LM130, LM 150, M5, M7d, PTG, MS55, H5, HS-5, EH5, available from Cabot Corporation. Preferably, fumed silica has particles 7 to 30 nanometers in size, and may be treated with dimethylsilyldichloride and the like such that a majority of the surface hydroxyl groups are capped.

The support may also include other reactive functional groups including primary alkyl amines, secondary alkyl amines, and the like, preferably where the groups are structurally incorporated in a polymeric chain and capable of an acid-base reaction with a Lewis acid. See, for example, the functional group containing polymers of U.S. Pat. No. 5,288,677.

Capping agents suitable for use herein preferably comprise a single ligand reactive with the silanol groups (e.g., $(CH_3)_3$ SiCl), alkyl aluminum compounds of the general formula $R_3Al$, wherein R is a hydrocarbon radical, phenylsilane $((C_6H_5)_n SiH_{(4-n)}$, n=1, 2, or 3), hexamethyldisilazane $((Me_3Si)_2NH)$, tetramethyldisilazane $((Me_2HSi)_2NH)$, and combinations comprising at least one of the foregoing. Difunctional coupling agents (e.g., $(CH_3)_2$ $SiCl_2$) may be employed to cap hydrogen-bonded pairs of silanol groups, which are present under the less severe calcining conditions. See, e.g., "Investigation of Quantitative SiOH Determination by the Siliane Treatment of Disperse Silica", Gotski, et al, Journ. of Colloid and Interface Science, Vol. 126, No. 2, December 1988, for discussion of the effect of silane coupling agents for silica polymeric fillers that will also be effective for modification of silanol groups on the catalyst supports disclosed herein.

EXAMPLES

Time-Resolved Luminescence Spectrometer

The experimental setup utilized a home-built spectrometer. An Argon-Ion laser (Coherence INNOVA 400) was used as the excitation source. This light source was attenuated by several irises to reduce the excitation power at the sample to about 1 mW. The laser beam was switched for several milliseconds using a Q-Switch (Inrad Laser Q-Switch 2 12-080), driven by a high voltage (~2 kV) pulse generator (Quantum Tech. Inc., HVP-525-LP). The On/Off contrast of the q-switch was 40. The analytes were mounted inside a liquid helium cryostat (Janis 7CNDT) utilized in nitrogen gas flow mode. Under these conditions, samples are cooled to ~80° K to prevent noise due to boiling nitrogen. The photon multiplier tube (PMT) detector (Model 814, Photon Technology International with Hamamatsu R928) was mounted on a monochromator (Model 101, Photon Technology International). The luminescence is passed through a low-pass filter (LP400). Monochromator resolution was 2 to 4 nm. A digitizing oscilloscope (Model TDS724D, SONY/Tektronix) recorded the transient signal voltage output from the PMT. Approximately 100 transients, each with a length of 1000 points, are accumulated on each wavelength step of the luminescence spectrum. The experiments were also repeated to improve signal-to-noise.

A program was written to control the experiment using Igor Pro software (Wavemetrics). The 2-D-Lifetime-Wavelength analysis was accomplished using the inverse Laplace transformation to calculate luminescence emission lifetimes. The analyzed data are plotted in a 2D Life Time with Profile layout as described above.

Materials and Sample Preparation.

Metallocene (I), 1,1'-bis(4-triethylsilylphenyl)methylene-(cyclopentadienyl)(2,7-di-tertiary-butyl-9-fluorenyl) hafnium dimethyl, was purchased and used as received.

In all samples, purified cyclohexane or toluene were used as solvents. Co-catalyst methylaluminoxane (MAO; 30 wt % in toluene) was used as received. Tris(pentafluorophenyl) borane (FAB) was re-crystallized from pentaneFAB, and dimethylaniliniumperfluorotetraphenylborate (DMAHD4) were sealed under nitrogen prior to use.

All time resolved luminescence spectra (TR-LS) samples were prepared inside a nitrogen atmosphere dry box purged with dry nitrogen. Solutions had metallocene or catalyst concentration of 1.0 millimolar unless otherwise noted.

After-preparation, each sample was transferred into an oven dried 5 mm Pyrex NMR tube (Wilmad Glass). Typical volume of sample is 30 to 100 microliters. A closed valve was attached to the top of each tube (Tip-Off Manifold, Wilmad Glass) and the assembly transported to a vacuum line outside the dry box where each sample was frozen in liquid nitrogen and set under vacuum to flame seal the tube.

Results and Analysis

Time-Resolved Luminescence Spectrum—Catalyst Reference

Figure 3:
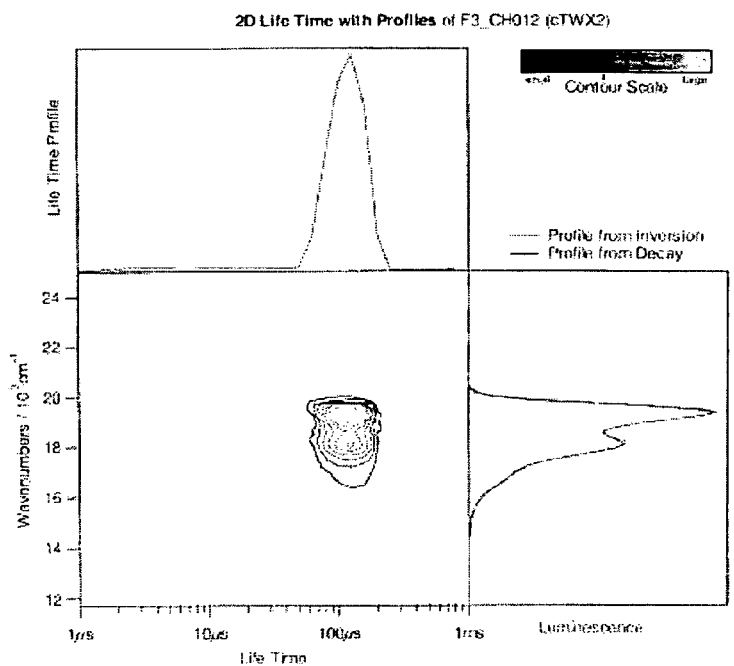
FIG. 3 depicts a time resolved luminescence spectrum of Metallocene (I) in cyclohexane at 80° K.

The two-dimensional plot for the reference Metallocene (I) in cyclohexane is shown in FIG. 3. A single emission energy and lifetime (19,400 cm$^{-1}$, and 140 microseconds at 80° K) is observed for the reference (without activator) Metallocene (I).

Al/Hf-100:1, the highly overlapping emission maxima for both energy and time of the 2D-luminescence spectrum (FIG. 7) suggests that the activation is substantial but still not complete. For Al/Hf 200, the 2D emission spectrum is consistent with more complete activation (FIG. 8). A similar experiment with 1 mM Metallocene (I) in cyclohexane activated with 30 w % MAO in toluene and MAO in excess of 200 (FIG. 9), shows the same activation behavior as in toluene.

Emission energy and lifetime data for each sample are organized in Table 1.

TABLE 1

Time Resolved Luminescence Spectra Recorded with Metallocene (I).

| | Pre-Catalyst | | | Unactivated Emission Reference | | Activated Emission Sample | |
|---|---|---|---|---|---|---|---|
| FIG. | (conc.) | Activator | Solvent | Energy[a] | Lifetime[b] | Energy[a] | Lifetime[b] |
| 3 | (I) (1 mmol) | | c-hexane | 19.4 | 0.16 | | |
| 4 | (I) (1 mmol) | FAB | c-hexane | | | 17.3 | 0.05 |
| 5 | | FAB | c-hexane | 22.7 | 240 | | |
| 6 | (I) (1 mmol) | DMAHD4 | c-hexane | | | 17.4 | 0.055 |
| 7 | (I) (5 mmol) | MAO (1:100) | toluene | 17.5 | 0.09 | 16.1 | 0.06 |
| 8 | (I) (5 mmol) | MAO (1:200) | toluene | | | 16.0 | 0.06 |
| 9 | (I) (1 mmol) | MAO (1:200) | c-hexane | | | 16.0 | 0.05 |

Figure 4:
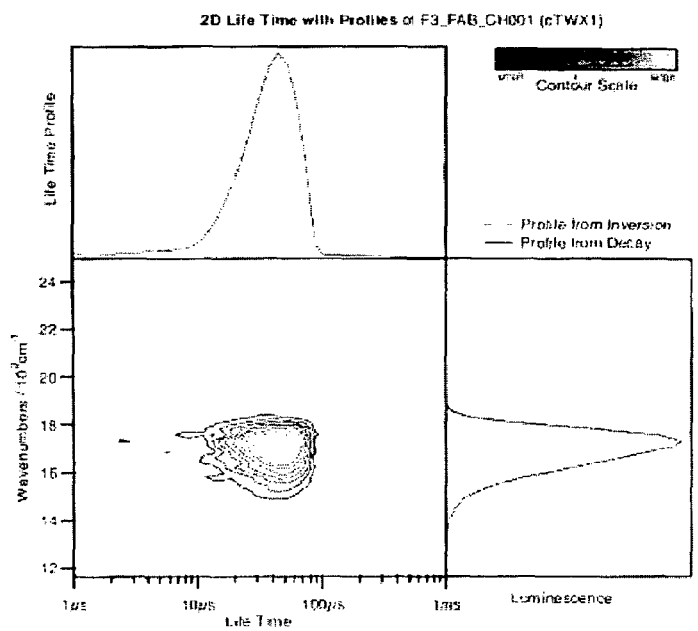
FIG. 4 depicts a time resolved luminescence spectrum of Metallocene (I) activated with tris(pentafluorophenyl)borane in cyclohexane at 80° K.
Figure 5:
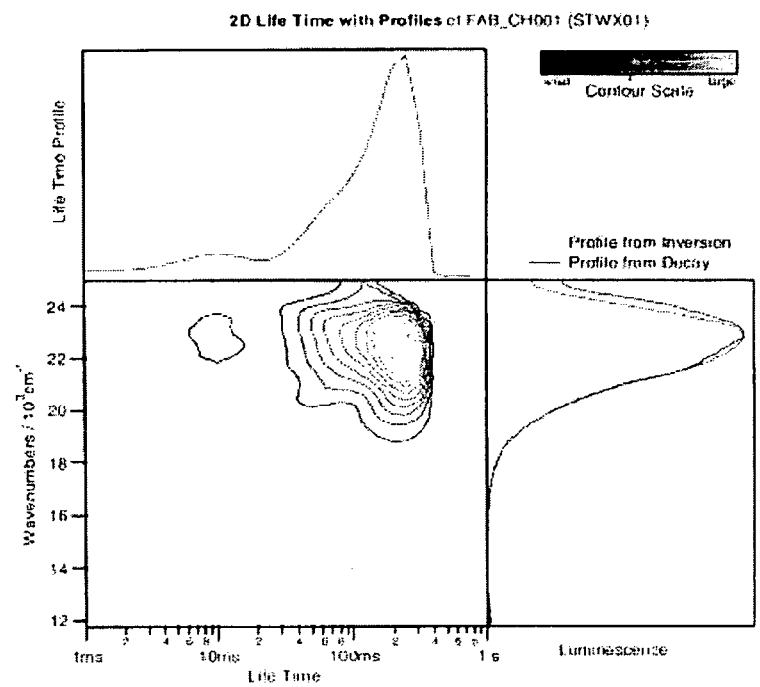
FIG. 5 depicts a time resolved luminescence spectrum of tris(pentafluorophenyl)borane in cyclohexane at 80° K.

[a]All energies 10$^3$ cm$^{-1}$
[b]Lifetime in 10$^{-3}$ seconds
c-hexane + cyclohexane Time-Resolved Luminescence Spectrum—Sample Spectrum Metallocene (I) was then activated with one equivalent of FAB in cyclohexane. The expected product is formally [Metallocene (I)]$^+$[MeFAB]$^-$. The two-dimensional plot for this reaction product is shown in FIG. 4. Both the red shifted emission spectrum and the single emission time are consistent with a single reaction product and quantitative consumption of the Metallocene (I) starting material. It could be possible that the emission spectrum from FAB or [MeFAB]$^-$ interferes with the product spectrum. FIG. 5 shows the time resolved emission spectrum for FAB in cyclohexane. Accordingly, the emission energy and lifetime observed do not interfere with the spectrum associated with metallocenium cation emission.

Metallocene (I) Activation with DMAHD4

Figure 6:
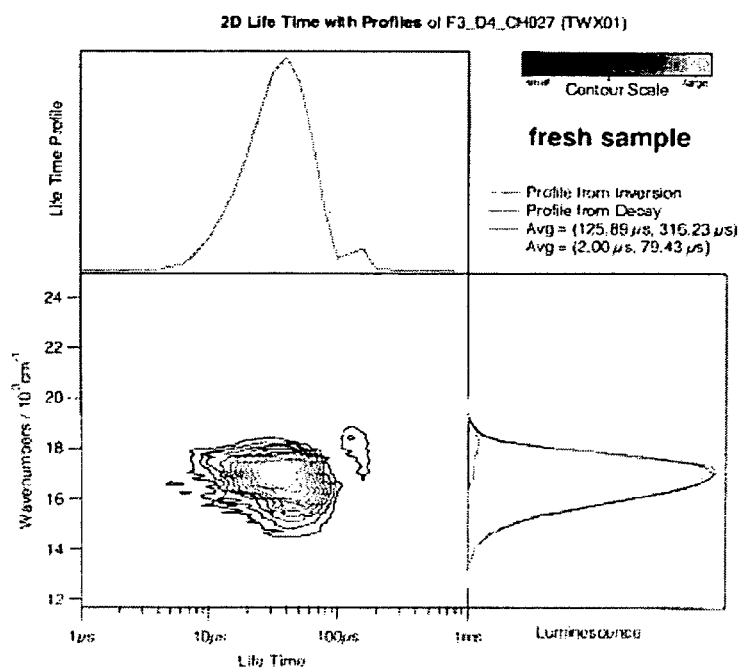
FIG. 6 depicts a time resolved luminescence spectrum of Metallocene (I) activated with DMAHD4 in cyclohexane at 80° K.

Metallocene (I) was also activated with DMAHD4 by preparing a 5 millimolar (mM) solution of Metallocene (I) in cyclohexane. The Metallocene (I) solution was then flushed onto dry DMAHD4 powder, wherein DMAHD4 was used in a slight excess of about 10 mol %. This slurry was mixed to produce a cloudy orange solution. The solution was than transferred into a NMR tube and frozen in liquid nitrogen within less than 5 minutes after mixing. FIG. 6 shows the spectrum of this sample. The active catalyst luminescence is the dominant emission. The signal from unactivated Metallocene (I) is less than 10% of the whole luminescence intensity. Accordingly, the method may be used to determine a degree or amount of activation.

Metallocene (I) Activation with MAO

Figure 7:
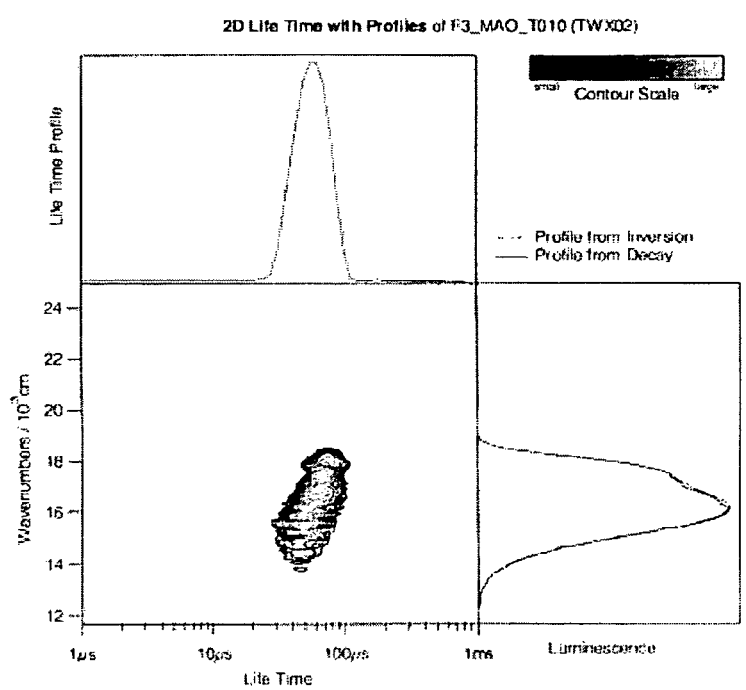
FIG. 7 depicts a time resolved luminescence spectrum of Metallocene (I) activated with MAO (1:100) in toluene at 80° K.
Figure 8:
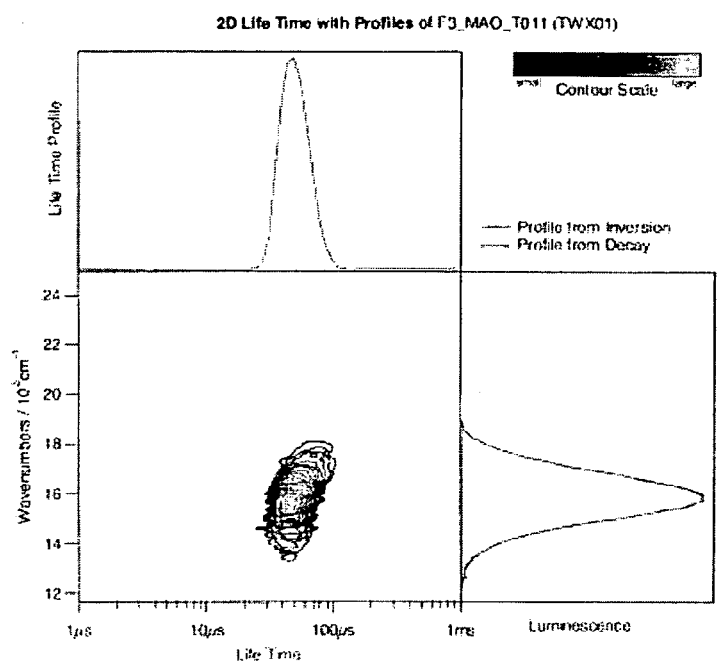
FIG. 8 depicts a time resolved luminescence spectrum of Metallocene (I) activated with MAO (1:200) in toluene at 80° K.

Activation of Metallocene (I) with MAO at 5 mM in toluene were based on estimated Al/Hf stoichiometry of 100:1 and 200:1, and are shown in FIGS. 7 and 8 respectively. FIG. 9 shows activation of F3 at 200:1 at 1 mM in cyclohexane. For As the data shows, the energy difference value (reference—sample) for these samples is greater than or equal to about 1000 cm$^{-1}$ and the lifetime difference value is greater than or equal to about 0.1 msec. Accordingly, the pre-catalyst of these examples may be adjudged as activated according to the instant invention. As such, a value of TR-LS for metallocene catalyst characterization is illustrated in these non-limiting examples.

Accordingly, emission lifetime data can be used in conjunction with the emission energy to provide a better understanding of metallocene activation/deactivation. This understanding may then be applied to the study of activation under different conditions including time, temperature, concentration, and solvents.

Determination of Activation Using the Activation Index "Ω"

An activated catalyst may also be described by an essentially non-zero value of Ω, as described herein. Samples were prepared and analyzed as outlined above. Representative data for the activation index Ω are shown in Table 2, Activation Index values for some metallocenes.

Metallocene (II) is bis(phenyl)methylene(cyclopentadienyl)(fluorenyl) hafnium dichloride.

Metallocene (III) is dimethylsilyl bis(2-methylindenyl)zirconium dichloride.

Metallocene (IV) is dimethylsilylbis(indenyl)hafnium dimethyl.

Metallocene (V) is dimethylsilylbis(tetrahydroindenyl) hafnium dichloride.

Metallocene (VI) is dimethylsilylbis(tetrahydroindenyl) hafnium difluoride.

Metallocene (VII) is dimethylsilyl bis(2-methyl-5-phenylindenyl)zirconium dichloride.

Metallocene (VIII) is dimethylsilyl bis(2-methyl-5-phenylindenyl)zirconium dimethyl.

Metallocene (IX) is bis(methyl, butyl-cyclopentadienyl)zirconium difluoride.

Metallocene (X) is bis(methyl, butyl-cyclopentadienyl)zirconium dichloride.

Metallocene (XI) is dimethylsilyl bis(2-methyl-5-phenylindenyl)zirconium dimethyl.

TABLE 2

Activation Index Values "Ω" for Some Metallocenes

| Metallocene | Activator/ Support | Reference Emission Energy $E_{max}$ ($cm^{-1}$) | Reference Lifetime $T_{max}$ (msec) | Sample Emission Energy $E_{max}$ ($cm^{-1}$) | Sample Lifetime $T_{max}$ (msec) | Activation Index Omega |
|---|---|---|---|---|---|---|
| (II) | -n/a- | 19,100 | 0.3 | — | — | — |
| (II) | MAO | — | — | 17,600 | 0.1 | 0.02451 |
| (III) | -n/a- | 18,200 | 0.8 | — | — | — |
| (III) | MAO | — | — | 15,600 | 0.2 | 0.05820 |
| (IV) | -n/a- | 20,400 | 0.3 | — | — | — |
| (IV) | silica-SBA | — | — | 18,000 | 0.05 | 0.06263 |
| (IV) | silica | — | — | 17,800 | 0.04 | 0.07794 |
| (V)SCl$_2$ | -n/a- | 21,600 | 2.2 | — | — | — |
| (V)SCl$_2$ | MAO | — | — | 17,200 | 0.5 | 0.10012 |
| (VI)SF$_2$ | -n/a- | 21,600 | 2.2 | — | — | — |
| (VI)SF$_2$ | MAO | — | — | 17,100 | 0.4 | 0.12101 |
| (VII) | -n/a- | 18,600 | 2.6 | — | — | — |
| (VII) | MAO | — | — | 16,100 | 0.4 | 0.11696 |
| (VIII) | -n/a- | 18,600 | 2.6 | — | — | — |
| (VIII) | MAO | — | — | 15,600 | 0.35 | 0.13952 |
| (IX) | -n/a- | 21,700 | 0.84 | — | — | — |
| (IX) | MAO | — | — | 19,800 | 0.08 | 0.11790 |
| (X) | -n/a- | 21,700 | 0.84 | — | — | — |
| (X) | MAO | — | — | 19,700 | 0.08 | 0.11873 |
| (XI) | -n/a- | 18,500 | 3.2 | — | — | — |
| (XI) | (XI)/FAB | — | — | 16,600 | 0.35 | 0.15895 |
| (XI) | Silica-SBA | 18,000 | 2 | 15,500 | 0.17 | 0.17663 |

MAO represents methylalumoxane.
FAB represents tris(pentafluorophenyl)borane.
SAB signifies a support bound activator.

The above samples were confirmed active based on lab scale polymerization of olefins. Accordingly, the time resolved luminescence method, in general, and the activation index in particular, can be used as a quick, inexpensive, and highly sensitive screening tool for catalyst discovery, optimization, and quality control of catalyst production and product manufacture.

Accordingly, disclosed herein is:

1 A. A method for determining the presence of an activated catalyst site in a catalyst system comprising a catalyst precursor and an activator, wherein the catalyst system is capable of providing a luminescence, the method comprising:

a) performing a time resolved luminescence analysis on a reference analyte comprising the catalyst precursor that is not in combination with the activator, to produce a plurality of reference output values, each being associated with a time resolved emission intensity at an emission energy;

b) performing a time resolved luminescence analysis on a sample analyte comprising the catalyst precursor in combination with the activator, to produce a plurality of sample output values, each being associated with a time resolved emission intensity at an emission energy;

c) determining a reference emission energy and a reference lifetime each associated with a maximum emission intensity in the reference output values;

d) determining a sample emission energy and a sample lifetime each associated with a maximum emission intensity in the sample output values;

e) subtracting the sample emission energy from the reference emission energy to produce an energy difference value;

f) subtracting the sample lifetime from the reference lifetime to produce a lifetime difference value;

g) determining if the energy difference value, the lifetime difference value, or both, are an essentially non-zero value to determine if the sample comprises an activated catalyst site.

2A. The method of claim 1A, further comprising determining if the energy difference value, the lifetime difference value, or both are positive numbers to determine if the sample comprises an activated catalyst site.

3A. The method of 1A to 2A, further comprising determining if the energy difference value, the lifetime difference value, or both are negative numbers to determine if the sample comprises an activated catalyst site.

4A. The method of 1A to 3A, wherein performing the time resolved luminescence analysis on an analyte comprises:

a) irradiating the analyte with one or more wavelengths of electromagnetic energy; and b) measuring the time dependence and intensity of an emitted radiation at one or more emission energies.

5A. The method of 1A to 4A, wherein the analyte is maintained at or below 25° C. while performing the time resolved luminescence analysis.

6A. The method of 1A to 5A, wherein the analyte is irradiated with electromagnetic energy having a wavelength of about 7000 Å to about 10 Å.

7A. The method of 1A to 6A, wherein the time resolved luminescence analysis on the reference analyte and the time resolved luminescence analysis on the sample analyte are obtained in similar solvents, at similar temperatures, at similar analyte concentrations, at similar impurity concentrations, under similar external conditions, or a combination comprising at least one of the forgoing.

8A. The method of 1A to 7A, wherein the determination of an energy difference value of greater than or equal to about 500 cm$^{-1}$, or less than or equal to about (−500 cm$^{-1}$) represents an activated catalyst site being present in the catalytic system.

9A. The method of 1A to 8A, wherein the determination of an energy difference value of greater than or equal to about 1000 cm$^{-1}$, or less than or equal to about (−1000 cm$^{-1}$) represents an activated catalyst site being present in the catalytic system.

10A. The method of 1A to 9A, wherein the determination of an energy difference value of greater than or equal to about 1500 cm$^{-1}$, or less than or equal to about (−1500 cm$^{-1}$) represents an activated catalyst site being present in the catalytic system.

11A. The method of 1A to 10A, wherein the determination of a lifetime difference value of greater than or equal to about 0.05 milliseconds represents an activated catalyst site being present in the catalyst system.

12A. The method of 1A to 11A, wherein the determination of a lifetime difference value of greater than or equal to about 0.1 milliseconds represents an activated catalyst site being present in the catalytic system.

13A. The method of 1A to 12A, wherein the determination of a lifetime difference value of greater than or equal to about 0.15 milliseconds represents an activated catalyst site being present in the catalyst system.

14A. The method of 1A to 13A, wherein the determination of an energy difference value of greater than or equal to about 500 cm$^{-1}$ and a lifetime difference value of greater than or equal to about 0.05 milliseconds represents an activated catalyst site being present in the catalyst system.

15A. The method of 1A to 14A, wherein the determination of an energy difference value of greater than or equal to about 1000 cm$^{-1}$ and a lifetime difference value of greater than or equal to about 0.10 milliseconds represents an activated catalyst site being present in the catalyst system.

16A. The method of 1A to 15A, wherein the determination of an energy difference value of greater than or equal to about 1500 cm$^{-1}$ and a lifetime difference value of greater than or equal to about 0.15 milliseconds represents an activated catalyst site being present in the catalyst system.

17A. The method of 1A to 16A, wherein the sample emission energy, the sample lifetime, the reference emission energy, the reference lifetime, or a combination comprising at least one of the foregoing, are each determined from one or more output values which are greater than or equal to about 2.5 times the signal to noise ratio of the analysis.

18A. A method for determining the number of activated catalytic sites in a catalyst system comprising the method of 1A to 17A, wherein the method further comprises:
determining a plurality of sample emission energies and a plurality of sample lifetimes each individually associated with a particular maximum emission intensity in the sample output values;
subtracting each sample emission energy from the reference emission energy to produce a plurality of energy difference values;
subtracting each sample lifetime from the reference lifetime to produce a plurality of lifetime difference values; and
determining if one or more of the plurality of energy difference values, the plurality of lifetime difference values, or a plurality of both, comprise an essentially non-zero value, wherein each non-zero energy difference value, each non-zero sample lifetime difference values, or both represent an active catalyst site in the catalyst system, to determine the number of active catalyst sites in the catalyst system.

19A. A method for determining the presence of a partially activated catalyst site in a catalyst system, comprising the methods of 1A to 18A, wherein the method further comprises:
determining a plurality of sample emission energies and a plurality of sample lifetimes each individually associated with a particular maximum emission intensity in the sample output values;
subtracting each sample emission energy from the reference emission energy to produce a plurality of energy difference values;
subtracting each sample lifetime from the reference lifetime to produce a plurality of lifetime difference values; and
determining if the plurality of energy difference values, the plurality of lifetime values, or both comprise an essentially zero value,
determining if the plurality of energy difference values, the plurality of lifetime values, or both comprise an essentially non-zero value, to determine the presence of a partially activated catalyst site in the catalyst system.

20A. A method for quantitatively determining the concentration of an activated catalyst site in a sample comprising a catalyst system, the method comprising the steps of the method of 1A to 19A, wherein the method further comprises:
determining a total emission intensity value "I" from the sum of a plurality of sample output values which correlate to an essentially non-zero energy value;
determining the concentration of an active catalyst site in the catalyst system present in the sample according to the equation c=(a*b)/I, wherein I is the total emission intensity value, a is the extinction coefficient of the activated catalyst site in the catalyst system, b is a measure of the optical path length of the sample, and c is equal to a concentration of the active catalyst site in the sample comprising the catalyst system.

21A. The method of 1A to 20A, wherein the catalyst system comprises a porous support.

22A. The method of 1A to 21A, wherein one or more essentially identical samples are prepared using different procedures.

23A. The method of 1A to 22A, wherein the catalyst precursor comprises an anionic catalyst precursor.

24A. The method of 1A to 23A, wherein the catalyst precursor comprises a cationic catalyst precursor.

25A. The method of 1A to 24A, wherein the catalyst precursor comprises a free radical catalyst precursor.

26A. The method of 1A to 25A, wherein the catalyst precursor comprises a coordination catalyst precursor.

27A. The method of 1A to 26A, wherein the catalyst precursor comprises a condensation catalyst precursor.

28A. The method of 1A to 27A, wherein the catalyst precursor comprises a zeolite comprising a heteroatom.

29A. The method of 1A to 28A, wherein the catalyst precursor comprises a SHOP catalyst precursor.

30A. The method of 1A to 29A, wherein the catalyst precursor comprises an oligomerization catalyst precursor.

31A. The method of 1A to 30A, wherein the catalyst precursor comprises a metallocene catalyst precursor.

32A. A method for determining the presence of an activated catalyst site in a catalyst system comprising a catalyst precursor and an activator, wherein the catalyst system is capable of providing a luminescence, the method comprising:
a) performing a time resolved luminescence analysis on a reference analyte comprising the catalyst precursor that is not in combination with the activator, to produce a plurality of reference output values, each being associated with a time resolved emission intensity at an emission energy;
b) performing a time resolved luminescence analysis on a sample analyte comprising the catalyst precursor in combination with the activator, to produce a plurality of sample output values, each being associated with a time resolved emission intensity at an emission energy;
c) determining a reference emission energy and a corresponding reference lifetime associated with a maximum emission intensity in the reference output values;
d) determining a sample emission energy and a corresponding sample lifetime associated with a maximum emission intensity in the sample output values;
e) determining the activation index $\Omega$ for the sample emission energy and the corresponding sample lifetime, wherein the activation index is determined according to the equation:

$$\Omega = \left( \frac{\log(T_{max}^{unactivated}) - \log(T_{max}^{activated})}{\log(T_{max}^{unactivated})} \right)^2 + \left( \frac{E_{max}^{unactivated} - E_{max}^{activated}}{E_{max}^{unactivated}} \right)^2$$

wherein $T_{max}^{unactivated}$ represents the reference lifetime;

$T_{max}^{activated}$ represents the sample lifetime;

$E_{max}^{unactivated}$ represents the reference emission energy $E_{max}^{activated}$ represents the sample emission energy
f) determining if the activation index for the sample energy and the corresponding sample lifetime is an essentially non-zero value to determine if the sample comprises an activated catalyst site.

33A. The method of 32A, wherein performing the time resolved luminescence analysis on an analyte comprises:
a) irradiating the analyte with one or more wavelengths of electromagnetic energy; and
b) measuring the time dependence and intensity of an emitted radiation at one or more emission energies.

34A. The method of 32A to 33A, wherein the analyte is maintained at or below 25° C. while performing the time resolved luminescence analysis.

35A. The method of 32A to 34A, wherein the analyte is irradiated with electromagnetic energy having a wavelength of about 7000 Å to about 10 Å.

36A. The method of 32A to 35A, wherein the time resolved luminescence analysis on the reference analyte and the time resolved luminescence analysis on the sample analyte are obtained in similar solvents, at similar temperatures, at similar analyte concentrations, at similar impurity concentrations, under similar external conditions, or a combination comprising at least one of the forgoing.

37A. The method of 32A to 36A, wherein determination of an activation of greater than or equal to about 0.001 represents an activated catalyst site being present in the catalytic system.

38A. The method of 32A to 37A, wherein determination of an activation of greater than or equal to about 0.01 represents an activated catalyst site being present in the catalytic system.

39A. The method of 32A to 38A, wherein determination of an activation of greater than or equal to about 0.1 represents an activated catalyst site being present in the catalytic system.

40A. The method of 32A to 39A, wherein the sample emission energy, the sample lifetime, the reference emission energy, the reference lifetime, or a combination comprising at least one of the foregoing, are each determined from one or more output values which are greater than or equal to about 2.5 times the signal to noise ratio of the analysis.

41A. A method for determining the number of activated catalytic sites in a catalyst system comprising the method of 32A to 40A, wherein the method further comprises:
determining a plurality of sample emission energies and a plurality of sample lifetimes each individually associated with a particular maximum emission intensity in the sample output values;
determining the activation index $\Omega$ for each of the sample emission energies and their corresponding sample lifetimes wherein each essentially non-zero activation index $\Omega$ represent an active catalyst site in the catalyst system, to determine the number of active catalyst sites in the catalyst system.

42A. A method for determining the presence of a partially activated catalyst site in a catalyst system, comprising the method of 32A to 41A, wherein the method further comprises:
determining a plurality of sample emission energies and a plurality of sample lifetimes each individually associated with a particular maximum emission intensity in the sample output values;
determining the activation index $\Omega$ for each of the sample emission energies and their corresponding sample lifetimes wherein each essentially non-zero activation index $\Omega$ represent an active catalyst site in the catalyst system, and wherein each essentially zero activation index value represents a partially activated catalyst site in the catalyst system, to determine the presence of a partially activated catalyst site in the catalyst system.

43A. A method for quantitatively determining the concentration of an activated catalyst site in a sample comprising a catalyst system, the method comprising the steps of the method of 32A to 42A, wherein the method further comprises:
determining a total emission intensity value "I" from the sum of a plurality of sample output values which correlate to an essentially non-zero activation index;

determining the concentration of an active catalyst site in the catalyst system present in the sample according to the equation c=(a*b)/I, wherein I is the total emission intensity value, a is the extinction coefficient of the activated catalyst site in the catalyst system, b is a measure of the optical path length of the sample, and c is equal to a concentration of the active catalyst site in the sample comprising the catalyst system.

44A. The method of 32A to 43A, wherein the catalyst system comprises a porous support.

45A. The method of 32A to 44A, wherein one or more essentially identical samples are prepared using different procedures.

46A. The method of 32A to 45A, wherein the catalyst precursor comprises an anionic catalyst precursor.

47A. The method of 32A to 46A, wherein the catalyst precursor comprises a cationic catalyst precursor.

48A. The method of 32A to 47A, wherein the catalyst precursor comprises a free radical catalyst precursor.

49A. The method of 32A to 48A, wherein the catalyst precursor comprises a coordination catalyst precursor.

50A. The method of 32A to 49A, wherein the catalyst precursor comprises a condensation catalyst precursor.

51A. The method of 32A to 50A, wherein the catalyst precursor comprises a zeolite comprising a heteroatom.

52A. The method of 32A to 51A, wherein the catalyst precursor comprises a SHOP catalyst precursor.

53A. The method of 32A to 52A, wherein the catalyst precursor comprises an oligomerization catalyst precursor.

54A. The method of 32A to 53A, wherein the catalyst precursor comprises a metallocene catalyst precursor.

Various tradenames used herein are indicated by a ™ symbol, indicating that the names may be protected by certain trademark rights. Some such names may also be registered trademarks in various jurisdictions.

All patents, test procedures, and other documents cited herein, including priority documents, are fully incorporated by reference to the extent such disclosure is not inconsistent with this invention and for all jurisdictions in which incorporation is permitted.

While the illustrative embodiments of the invention have been described with particularity, it will be understood that various other modifications will be parent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains.

When numerical lower limits and numerical upper limits are listed herein, ranges from any lower limit to any upper limit are contemplated.

The invention claimed is:

1. A method for determining the presence of an activated catalyst site in a catalyst system comprising a catalyst precursor and an activator, wherein the catalyst system is capable of providing a luminescence, the method comprising:
   a) performing a time resolved luminescence analysis on a reference analyte comprising the catalyst precursor that is not in combination with the activator, to produce a plurality of reference output values, each being associated with a time resolved emission intensity at an emission energy;
   b) performing a time resolved luminescence analysis on a sample analyte comprising the catalyst precursor in combination with the activator, to produce a plurality of sample output values, each being associated with a time resolved emission intensity at an emission energy;
   c) determining a reference emission energy and a reference lifetime each associated with a maximum emission intensity in the reference output values;
   d) determining a sample emission energy and a sample lifetime each associated with a maximum emission intensity in the sample output values;
   e) subtracting the sample emission energy from the reference emission energy to produce an energy difference value;
   f) subtracting the sample lifetime from the reference lifetime to produce a lifetime difference value;
   g) determining if the energy difference value, the lifetime difference value, or both, are an essentially non-zero value to determine if the sample comprises an activated catalyst site,
   h) determining a total emission intensity value "I" from the sum of a plurality of sample output values which correlate to an essentially non-zero energy value; and
   i) determining the concentration of an active catalyst site in the catalyst system present in the sample according to the equation c=(a*b)/I, wherein I is the total emission intensity value, a is the extinction coefficient of the activated catalyst site in the catalyst system, b is a measure of the optical path length of the sample, and c is equal to a concentration of the active catalyst site in the sample comprising the catalyst system.

2. The method of claim 1, further comprising determining if the energy difference value, the lifetime difference value, or both are positive numbers to determine if the sample comprises an activated catalyst site.

3. The method of claim 1, further comprising determining if the energy difference value, the lifetime difference value, or both are negative numbers to determine if the sample comprises an activated catalyst site.

4. The method of claim 1, wherein performing the time resolved luminescence analysis on an analyte comprises:
   a) irradiating the analyte with one or more wavelengths of electromagnetic energy; and
   b) measuring the time dependence and intensity of an emitted radiation at one or more emission energies.

5. The method of claim 4, wherein the analyte is maintained at or below 25° C. while performing the time resolved luminescence analysis.

6. The method of claim 1, wherein the time resolved luminescence analysis on the reference analyte and the time resolved luminescence analysis on the sample analyte are obtained in similar solvents, at similar temperatures, at similar analyte concentrations, at similar impurity concentrations, under similar external conditions, or a combination comprising at least one of the forgoing.

7. The method of claim 1, wherein the determination of an energy difference value of greater than or equal to about 500 $cm^{-1}$, or less than or equal to about ($-500cm^{-1}$) represents an activated catalyst site being present in the catalytic system.

8. The method of claim 1, wherein the determination of a lifetime difference value of greater than or equal to about 0.05 milliseconds represents an activated catalyst site being present in the catalytic system.

9. The method of claim 1, wherein the sample emission energy, the sample lifetime, the reference emission energy, the reference lifetime, or a combination comprising at least one of the foregoing, are each determined from one or more output values which are greater than or equal to about 2.5 times the signal to noise ratio of the analysis.

10. A method for determining the number of activated catalytic sites in a catalyst system comprising the method of claim 1, wherein the method further comprises:
   determining a plurality of sample emission energies and a plurality of sample lifetimes each individually associated with a particular maximum emission intensity in the sample output values;
   subtracting each sample emission energy from the reference emission energy to produce a plurality of energy difference values;
   subtracting each sample lifetime from the reference lifetime to produce a plurality of lifetime difference values; and
   determining if one or more of the plurality of energy difference values, the plurality of lifetime difference values, or a plurality of both, comprise an essentially non-zero value, wherein each non-zero energy difference value, each non-zero sample lifetime difference values, or both represent an active catalyst site in the catalyst system, to determine the number of active catalyst sites in the catalyst system.

11. A method for determining the presence of a partially activated catalyst site in a catalyst system, comprising the method of claim 1, wherein the method further comprises:
   determining a plurality of sample emission energies and a plurality of sample lifetimes each individually associated with a particular maximum emission intensity in the sample output values;
   subtracting each sample emission energy from the reference emission energy to produce a plurality of energy difference values;
   subtracting each sample lifetime from the reference lifetime to produce a plurality of lifetime difference values; and
   determining if the plurality of energy difference values, the plurality of lifetime values, or both comprise an essentially zero value,
   determining if the plurality of energy difference values, the plurality of lifetime values, or both comprise an essentially non-zero value, to determine the presence of a partially activated catalyst site in the catalyst system.

12. The method of claim 1, wherein one or more essentially identical samples are prepared using different procedures.

* * * * *